US006989245B2

(12) United States Patent
Huang

(10) Patent No.: US 6,989,245 B2
(45) Date of Patent: Jan. 24, 2006

(54) SCREENING, DIAGNOSTIC AND THERAPEUTIC METHODS RELATING TO RIZ

(75) Inventor: Shi Huang, San Diego, CA (US)

(73) Assignee: The Burnham Institute, La Jolla, CA (US)

( * ) Notice: Subject to any disclaimer, the term of this patent is extended or adjusted under 35 U.S.C. 154(b) by 319 days.

(21) Appl. No.: 10/142,650

(22) Filed: May 9, 2002

(65) Prior Publication Data

US 2003/0092095 A1 May 15, 2003

Related U.S. Application Data

(60) Provisional application No. 60/290,481, filed on May 11, 2001.

(51) Int. Cl.
*C12Q 1/48* (2006.01)
*C12N 9/10* (2006.01)
*C07K 7/00* (2006.01)

(52) U.S. Cl. ............................ 435/15; 435/193; 530/327
(58) Field of Classification Search ................... 435/15, 435/193; 530/327
See application file for complete search history.

(56) References Cited

U.S. PATENT DOCUMENTS

| 5,811,304 | A | * | 9/1998 | Huang | 435/325 |
| 6,069,231 | A | * | 5/2000 | Huang | 530/327 |
| 6,323,335 | B1 | * | 11/2001 | Huang | 536/23.5 |
| 6,555,329 | B2 | | 4/2003 | Jenuwein et al. | |
| 6,586,579 | B1 | * | 7/2003 | Huang | 536/23.1 |
| 2002/0039776 | A1 | | 4/2002 | Jenuwein et al. | 435/193 |
| 2002/0115215 | A1 | * | 8/2002 | Wolffe et al. | 435/455 |

OTHER PUBLICATIONS

Buyse et al., "The retinoblastoma protein binds to RIZ, a zinc–finger protein that shares an epitope with the adenovirus E1A protein", *Proc. Natl. Acad. Sci.* 92:4667–4471 (1995).
Steele–Perkins et al., "Tumor formation and invactivation of RIZ1, and RB–binding member of a nuclear protein–methyltransferase superfamily", *Genes & Development* 15:2250–2262 (2001).
Abbondanza et al., "The retinoblastoma–interacting zinc–finger protein RIZ is a downstream effector of estrogen action," *Proc. Natl. Acad. Sci. USA* 97(7) :3130–3135 (2000).
Agadir et al., "Resistance of HBL100 human breast epithelial cells to vitamin D action," *Carcinogenesis* 20:577–582 (1999).
Allegra, "Methtrexate and 5–Fluorouracil following Tamoxifen and Premarin in advanced breast cancer," *Semin. Oncol.* 10:23–28 (1983).

Anzick et al., "AIB1, a steroid receptor coactivator amplified in breast and ovarian cancer," *Science* 277:965–968 (1997).
Bannister et al., "Selective recognition of methylated lysine 9 on histone H3 by the HP1 chromo domain," *Nature* 410:120–124 (2001).
Bhattacharjee et al., "Histone H1 phosphorylation by Cdk2 selectively modulates mouse mammary tumor virus transcription through chromatin remodeling," *Mol. Cell. Biol.* 21:5417–5425 (2001).
Buyse et al., "The retinoblastoma protein binds to RIZ, a zinc–finger protein that shares an epitope with the adenovirus E1A protein," *Proc. Natl. Acad. Sci. USA* 92:4467–4471 (1995).
Chadwick et al., "Candidate tumor suppressor RIZ is frequently involved in colorectal carcinogenesis," *Proc. Natl. Acad. Sci. USA* 97(6) : 2662–2667 (2000).
Dou and Gorovsky, "Phosphorylation of linker histone H1 regulates gene expression in vivo by creating a charge patch," *Mol. Cell.* 6:225–231 (2000).
Du et al., "Hypermethylation in human cancers of the *RIZ1* tumor suppressor gene, a member of a histone/protein methyltransferase superfamily," *Cancer Research* 61:8094–8099 (2001).
Elledge et al., "Estrogen receptor (ER) and progesterone receptor (PgR), by ligand–binding assay compared to tamoxifen in metastatic breast cancer: A Southwest oncology group study," *Int. J. Cancer* 89:111–117 (2000).
Evans et al., "The interactive web–based histology atlas system," *Oncogene* 19:989–991 (2000).
Gazzerro et al., "Differentiation of myeloid cell lines correlates with a selective expression of RIZ protein," *Mol. Med.* 7:552–560 (2001).
Gossler et al., "Transgenesis by means of blastocyst–derived embryonic stem cell lines, " *Proc. Natl. Acad. Sci. USA* 83:9065–9069 (1986).

(Continued)

*Primary Examiner*—Jean C. Witz
*Assistant Examiner*—Susan Hanley
(74) *Attorney, Agent, or Firm*—McDermott Will & Emery LLP

(57) ABSTRACT

The invention provides a method of screening for a compound that modulates RIZ histone methyltransferase (HMT) activity, by contacting a RIZ or RIZ fragment having HMT activity with one or more candidate compounds, and determining histone methyltransferase activity of the contacted RIZ or RIZ fragment. Also provided is a method of screening for a compound that modulates progesterone receptor (PR) activity, by providing a RIZ1 modulatory compound, and determining the ability of the RIZ1 modulatory compound to modulate PR activity. Further provided is a method of identifying an individual with an estrogen receptor positive (ER+) tumor having a reduced likelihood of responding to endocrine therapy. The method involves determining the RIZ1 status of the tumor, wherein an abnormal RIZ1 status identifies the individual as an individual with a reduced likelihood of responding to endocrine therapy.

9 Claims, 7 Drawing Sheets

OTHER PUBLICATIONS

Goulding et al., "A new immunohistochemical antibody for the assessment of estrogen receptor status on routine formalin–fixed tissue samples," *Human Pathology* 26(3):291–294 (1995).

Harvey et al., "Estrogen receptor status by immunohitchemistry is superior to the ligand–binding assay for predicting response to adjuvant endocrine therapy in breast cancer," *J. Clinical Oncology* 17(5) : 1474–1481 (1999).

He et al., "RIZ1, but not the alternative RIZ2 product of the same gene, is underexpressed in breast cancer, and forced RIZ1 expression causes G2–M cell cycle arrest and/or apoptosis," *Cancer Research* 58:4238–4244 (1998).

Hennighausen and Robinson, "Think globally, act locally: The making of a mouse mammary gland," *Genes & Development* 12:449–455 (1998).

Huang et al., "The PR domain of the Rb–binding zinc finger protein RIZ1 is a protein binding interface and is related to the SET domain functioning in chromatin–mediated gene expression," *J. Biol. Chem.* 273:15933–15939 (1988).

Jiang et al., "Adenovirus Expressing *RIZ1* in tumor suppressor gene therapy of microsatellite–unstable colorectal cancers," *Cancer Research* 61:1796–1798 (2001).

Jiang et al., "Decreased RIZ1 expression but not RIZ2 in hepatoma and suppression of hepatoma tumorigenicity by RIZ1" *Intl. J. Cancer* 83:541–546 (1999).

Jiang and Huang, "The *yin–yang* of PR–domain family genes in tumorigenesis," *Histol. Histopathol.* 15:109–117 (2000).

Jordan, "Historical perspective on hormonal therapy of advanced breast cancer,"*Clinical Therapeutics* 24: A3–A16 (Supplement A) (2002).

Kurebayashi et al., "Expression levels of Estrogen Receptor–α, estrogen Receptor–β, coactivators, and corepressors in breast cancer," *Clin. Cancer Res.* 6:512–518 (2000).

Lachner et al., "Methylation of histone H3 lysine 9 creates a binding site for HP1 proteins," *Nature* 410:116–120 (2001).

Leake, "Detection of the oestrogen receptor (ER) : immunohistochemical versus cytosol measurements," *European J. of Cancer* 36:S13–S23 (2000).

Lee et al, "A retinoic acid response element that overlaps an estrogen response element mediates multihormonal sensitivity in transcriptional activation of the lactoferrin gene," *Mol. Cell. Biol.* 15:4194–4207 (1995).

Liu et al., "The retinblastoma interacting zinc finger gene RIZ produces a PR domain–lacking product through an internal promoter," *J. Biol. Chem.* 272(5) : 2984–2991 (1997).

Lubahn et al., "Alteration of reproductive function but not prenatal sexual development after insertional disruption of the mouse estrogen receptor gene," *Proc.Natl. Acad Sci. USA* 90:1162–11166 (1993).

Lydon et al., "Mice lacking progesterone receptor exhibit pleiotropic reproductive abnormalities," *Genes & Development* 9:2266–2278 (1995).

Mansour et al., "Disruption of the proto–oncogene *int*–2 in mouse embryo–derived stem cells: a general strategy for targeting mutations to non–selectable genes," *Nature* 336:348–352 (1988).

McKay and Cidlowski, "Cross–talk between nuclear factor–☐B and the steroid hormone receptors: Mechanism of mutual antagonism," *Endocrinol.* 12:45–56 (1998).

Medici et al., "Identification of a DNA binding protein cooperating with estrogen receptor as RIZ (retinoblastoma interacting zinc finger protein), " *Biochem. and Biophys. Research Commun.* 264:983–989 (199).

Murphy et al., "Altered expression of estrogen receptor coregulators during human breast tumorigenesis," *Cancer Res.* 60:6266–62712 (2000).

Nakayama et al., "Role of histone H3 lysine 9 methylation in epigenetic control of heterochromatin assembly," *Science* 292:110–113 (2001).

Nishioka et al., "Set9, a novel histone H3 methyltransferase that facilitates transcription by precluding histone tail modifications required for heterochromatin formation," *Genes & Dev.* 16:479–489 (2002).

Noma et al., "Transitions in distinct histone H3 methylation patterns at the heterochromatin domain boundaries," *Science* 293:1150–1155 (2001).

Ohe et al., "Human Spleen Histone H1. Isolation and amino acid sequence of a main variant, H1b," *J. Biochem.* (*Tokyo*) 100:359–368 (1986).

Osborne et al., "The value of estrogena and progesterone receptors in the treatment of breast cancer," *Cancer* 46:2884–2888 (1980).

Piao et al., "Frequent frameshift mutations of *RIZ* in sporadic gastrointestinal and endometrial carcinomas with microsatellite instability," *Cancer Res.* 60:4701–4704 (2000).

Rea et al., "Regulation of chromatin structure by site–specific histone H3 methyltransferases," *Nature* 406:593–599 (2000).

Sakurada et al., "*RIZ*, the retinoblastoma protein interacting zinc finger gene is mutated in genetically unstable cancers of the pancreas, stomach, and colorectum," *Genes, Chromosomes & Cancer* 30:207–211 (2001).

Shapiro et al., "Identification and cloning of the *G3B* cDNA encoding a 3' segment of a protein binding to GATA–3," *Gene* 163:329–330 (1995).

Soriano et al., "Targeted disruption of the c–src Proto–Oncogene leads to osteopetrosis in mice," *Cell* 64:693–702 (1991).

Steele–Perkins et al., "Tumor formation and inactivation of RIZ1, an Rb–binding member of a nuclear protein–methyltransferase superfamily," *Genes & Development* 15:2250–2262 (2001).

Strahl et al., "Methylation of histone H4 at arginine 3 occurs in vivo and is mediated by the nuclear receptor coactivator PRMT1," *Curr. Biol.* 11:996–1000 (2001).

Tachibana et al., "SET domain–containing protein, G9a, is a novel lysine–preferring mammalian histone methyltransferase with hyperactivity and specific selectivity to lysines 9 and 27 of histone H3," *J. Biol. Chem.* 276:25309–25317 (2001).

Thenot et al., "Estrogen receptor cofactors expression in breast and endometrial human cancer cells," *Mol. Cell. Endocrinol.* 156:85–93 (1999).

Tibbetts et al., "Mutual and intercompartmental regulation of estrogen receptor and progesterone receptor expression in the mouse uterus," *Biol. Reprod.* 59:1143–1152 (1998).

Wang et al., "Regulation of somatic growth by the p160 coactivator p/CIP, " *Proc. Natl. Acad. Sci. USA* 97:13549–13554 (2000).

Wang et al., "Purification and functional characterization of a histone H3–lysine 4–specific methyltransferase," *Molecular Cell* 8:1207–1217 (2001).

Xie et al., "Transcriptional repression mediated by the PR Domain Zinc Finger Gene *RIZ*, " *J. Biol. Chem.* 272:26360–26366 (1997).

Xu et al., "Partial hormone resistance in mice with disruption of the steroid receptor coactivator-1 (SRC-1) Gene," *Science* 279:1922–1925 (1998).

Xu et al., "The steroid receptor coactivator SRC-3 (p/CIP/RAC3/AIB1/ACTR/TRAM-1) is required for normal growth, puberty, female reproductive function, and mammary gland development," *Proc. Natl. Acad. Sci. USA* 97:6379–6384 (2000).

Zhang et al., "Retinoid X receptor is an auxillary protein for thyroid hormone and retinoic acid receptors," *Nature* 355:441–446 (1992).

Zhang et al., "Regulation of α-Fetoprotein gene expression by antagonism between AP-1 and the glucocorticoid receptor at their overlapping binding site," *J. Biol. Chem.* 266:8248–8254 (1991).

GenBank Accession No. AAC50820.

GenBank Accession No. AAA74468.

\* cited by examiner-

SCREENING, DIAGNOSTIC AND THERAPEUTIC METHODS RELATING TO RIZ

This application claims the benefit of U.S. Provisional Application Ser. No. 60/290,481, filed May 11, 2001, which is incorporated herein by reference in its entirety.

This invention was made with United States Government support under grant numbers CA76146 and CA60988 awarded by the National Institutes of Health. The U.S. Government has certain rights in this invention.

BACKGROUND OF THE INVENTION

1. Field of the Invention

This invention relates generally to the fields of cancer biology and endocrinology and, more specifically, to biological activities of RIZ polypeptides.

2. Background Information

Post-translational addition of methyl groups to the amino-terminal tails of histone proteins is catalyzed by a family of proteins known as histone methyltransferases (HMTs). Histone site-specific methylation is associated with a variety of fundamental cellular processes, including transcriptional regulation, epigenetic silencing and heterochromatin formation. Loss of HMT function is expected to directly contribute to the de-differentiation and genomic instability that are characteristic of cancer.

Further implicating HMTs in cancer, it has been shown that a deficiency in dietary methionine or folate causes cancer. Dietary methionine and folate in turn regulate the cellular levels of S-adenosylmethionine (SAM), which is used as a methyl group donor by methyltransferases.) Additionally, several independent lines of investigation have revealed that alterations in the methionine metabolic pathway, which can lead to a deficiency in SAM and/or an increase in the methyltransferase inhibitor S-adenosylhomocysteine (SAH), are associated with cancer.

Thus, there exists a need to identify proteins with histone methyltransferase activity, determine their substrates and regulators, and identify compounds that modulate their activity. In particular, there exists a need to identify histone methyltransferase activity within proteins already recognized to play critical roles in regulating cell proliferation. Compounds that modulate the HMT activity of such proteins are expected to be useful as therapeutics to regulate cell growth.

The steroid hormone progesterone is a critical component of the female reproductive cycle and is required to maintain pregnancy. The molecular target of progesterone is the intracellular progesterone receptor. Upon binding to progesterone, the progesterone receptor translocates to the nucleus where it binds as a transcription factor to DNA transcriptional elements present in progesterone-regulated genes.

Ligands to the progesterone receptor play an important role in female reproductive medicine and cancers. For example, progesterone and its synthetic analogs are useful in birth control formulations, in treating endometriosis and in maintaining pregnancy. Antagonists to progesterone are useful in treating chronic disorders such as certain forms of hormone dependent cancer of the breast, ovaries and endometrium (the lining of the uterus) and in treating uterine fibroids. Progesterone antagonists are also useful in combination with other drugs for terminanting early stage pregnancies.

Compounds that modulate progesterone receptor activity are thus expected to be useful in reproductive applications and for treating malignant disorders. However, suitable high-throughput assays for identifying such compounds are currently lacking, in part due to a lack of understanding of physiologically relevant interactions of the progesterone receptor with cellular molecules. Thus, there exists a need for improved methods to screen for compounds that modulate progesterone receptor activity.

The steroid hormone estrogen directly and indirectly promotes the proliferation of tissues expressing estrogen receptors. Endocrine therapy to reduce the proliferative effects of estrogens, including therapy with selective estrogen receptor modulators (SERMs) such as tamoxifen, is currently the preferred first-line therapy in patients with estrogen receptor positive (ER+) tumors. However, a significant portion of patients with ER+ tumors do not respond to endocrine therapy. In these patients, alternative therapies are warranted in order to improve the odds of survival. Currently, there is no satisfactory method of predicting which ER+ tumors will respond to endocrine therapy.

Thus, there exists a need to identify molecules that correlate with loss of estrogen responsiveness in ER+ tumors, in order to more accurately determine which individuals are more or less likely to respond to endocrine therapy. Using such a correlation, an individualized course of treatment with an improved likelihood of success can be chosen.

The present invention satisfies these needs, and provides related advantages as well.

SUMMARY OF THE INVENTION

The invention provides a method of screening for a compound that modulates RIZ histone methyltransferase activity. The method involves contacting a RIZ or RIZ fragment having histone methyltransferase activity with one or more candidate compounds, and determining histone methyltransferase activity of the contacted RIZ or RIZ fragment. A compound that modulates RIZ histone methyltransferase activity is identified.

The invention also provides a method of screening for a compound that modulates progesterone receptor activity. The method involves providing a RIZ1 modulatory compound, and determining the ability of the RIZ1 modulatory compound to modulate progesterone receptor activity. A compound that modulates progesterone receptor activity is thereby identified.

Also provided is a method of identifying an individual with an estrogen receptor positive (ER+) tumor having a reduced likelihood of responding to endocrine therapy. The method involves determining the RIZ1 status of the tumor, wherein an abnormal RIZ1 status identifies the individual as an individual with a reduced likelihood of responding to endocrine therapy.

DETAILED DESCRIPTION OF THE INVENTION

Figure 1:
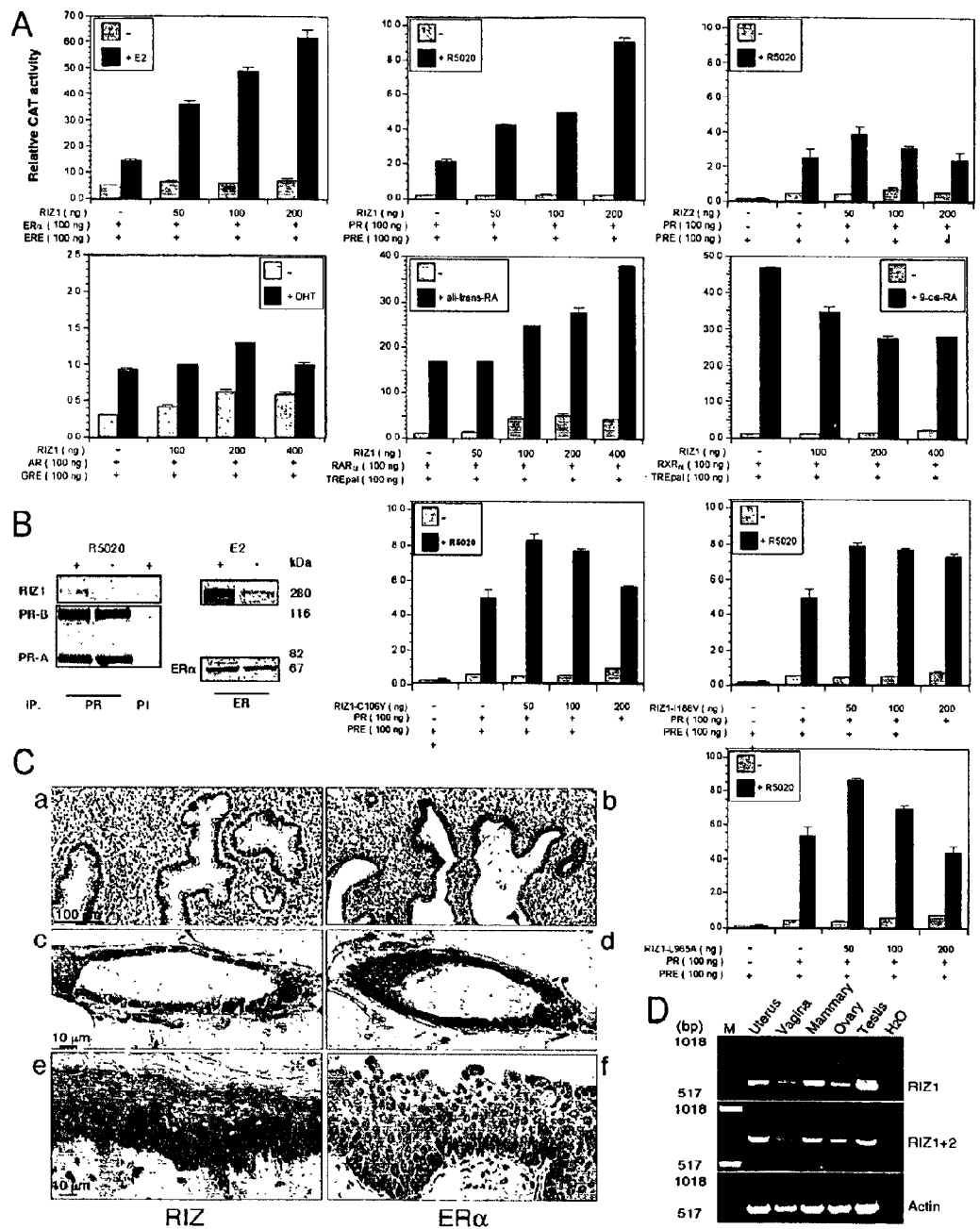
FIG. 1A shows the effect of RIZ1 on hormone responsive promoters. The indicated amounts of RIZ1 and various nuclear hormone receptor expression vectors were cotransfected with a reporter construct containing the appropriate hormone receptor response element into CV-1 cells. Cells were treated with or without the indicated hormone for 24 h and assayed for CAT activity. Data shown represent the means±SEM of three independent experiments.
FIG. 1B shows that RIZ1 forms hormone-dependent protein complexes in vivo with ERα and progesterone receptor proteins. T47-D (for progesterone receptor) and MCF-7 (for ER) cells were infected with adenovirus expressing RIZ1. Cell extracts treated with or without hormones were prepared and immunoprecipitated (IP) with preimmune serum or monoclonal antibodies against progesterone receptor (PR) (detecting both PR-B and PR-A) or ERα, as indicated. The immunoprecipitated products were analyzed by immunoblot analysis using RIZ1, progesterone receptor or ERα monoclonal antibodies (2D7, 1A6, and sc-8005, respectively).
FIG. 1C shows immunohistochemistry analysis of RIZ expression in target organs of female sex steroid hormones. Tissues from 7-week old virgin wild-type mice were analyzed for expression of RIZ and ERAα. The sections show RIZ and ERα immunostaining in uterus (panels a and b), breast (c and d), and vaginal epithelium (e and f). Scale bar in a, c, and e also applies to b, d, and f respectively.
FIG. 1D shows RT-PCR analysis of RIZ1 expression in target organs of female sex steroid hormones. Total RNAs isolated from the indicated tissues of mice were used for RT-PCR analysis.

The retinoblatoma-protein-interacting zinc finger gene, or "RIZ" gene, was originally isolated in a functional screen for proteins that bind to the Rb tumor suppressor (Buyse et al., *Proc. Natl. Acad. Sci. USA* 92:4467–4471 (1995)). Two products of the RIZ gene are produced, owing to alternative promoter usage. RIZ2 is identical to RIZ1 except that it lacks the N-terminal 200 (rat) or 201 (human) amino acids (Liu et al., *J. Biol. Chem.* 272:2984–2991 (1997)).

RIZ1 is considered to be a tumor suppressor gene, as indicated by the following lines of evidence. The RIZ gene maps to chromosome 1p36, one of the most commonly deleted regions in human cancers. Gene silencing of RIZ1, but not RIZ2, is common in many types of human tumors— including breast cancer, liver cancer, colon cancer, neuroblastoma, melanoma, lung cancer and osteosarcoma (Chadwick et al., *Proc. Natl. Acad. Sci. USA* 97:2662–2667 (2000); He et al., *Cancer Res.* 58:4238–4244 (1998); Jiang et al., *Int. J. Cancer* 83:541–547 (1999))—and is associated with promoter DNA methylation (Du et al., *Cancer Res.* 22:8094–8099 (2001)). RIZ1 missense mutations (Steele-Perkins et al., *Genes Dev.* 15:2250–2262 (2001)) and frameshift mutations (Chadwick et al., supra (2000); Piao et al., *Cancer Res.* 60:4701–47–4 (2000); Sakurada et al., *Genes, Chroms. Cancer* 30:207–211 (2001)) are common in human tumors. RIZ1 expression induces cell-cycle arrest, apoptosis induction and suppression of xenograft tumors (Chadwick et al., supra 2000; He et al., supra (1998); Jiang et al., supra (1999); Jiang and Huang, *Cancer Res.* 61:1796–1798 (2001)). Finally, mouse gene knock-out models show that inactivation of RIZ1, while retaining normal RIZ2, causes tumor susceptibility (Steele-Perkins et al., supra (2001)). These studies suggest an important function for the N-terminus of RIZ1 in its tumor suppressor activity.

The N-terminus of RIZ1 contains a domain of about 130 residues called the "PR-domain," between about residues 30–160 of RIZ1. The PR-domain was initially identified as a region that showed homology between RIZ1 and the transcriptional repressor PRDI-BF1. This domain was later found to be structurally related to the SET-domain (Huang et al., *J. Biol. Chem.* 273:15933–15940 (1988)), which was recently shown to be a catalytic motif of lysine histone methyltransferases (HMTs) (Rea et al., *Nature* 406:593–599 (2000)). Despite the sequence similarity between PR and SET, the PR and SET domains are clearly distinct. First, identities among PR-domains or among SET domains are usually about 40%, whereas identities between PR and SET domains are typically only about 20–30%. Second, SET domains are primarily found at the carboxyl termini of proteins, whereas PR-domains are mostly located at the amino termini. Prior to the instant disclosure, no enzymatic activity of a PR-domain had been described. Furthermore, histone methyltransferase activity of the PR-domain of RIZ1, or of other domains within RIZ, had not been described.

As disclosed herein, both RIZ1 and RIZ2 proteins have histone methyltransferase activity. Despite its actions as a tumor suppression, RIZ1 also acts as an estrogen receptor (ER) and progesterone receptor coactivator involved in regulating the normal proliferation and differentiation of estrogen- and progesterone-responsive tissues (see Example I). Because of the dual role of RIZ as a growth suppressor and growth promoter, compounds that modulate RIZ histone methyltransferase activity are expected to be useful in applications in which it desirable to positively or negatively modulate cell growth, including treatment of hyperproliferative disorders (e.g. neoplasia, hyperplasia, inflammatory conditions and the like) and treatment of hypoproliferative disorders (e.g. various disorders of hematopoiesis, wound healing and the like).

The invention thus provides a method of screening for a compound that modulates RIZ histone methyltransferase activity. The method is practiced by contacting a RIZ or RIZ fragment having histone methyltransferase activity with one or more candidate compounds, and assaying histone methyltransferase activity of the contacted RIZ or RIZ fragment. A compound that modulates RIZ histone methyltransferase activity of the RIZ or RIZ fragment is thereby identified.

As disclosed herein, HMT activity is present both in the PR-domain specific to RIZ1, and also in the C-terminal PR-binding domain (or PBD) common to RIZ1 and RIZ2. Accordingly, either RIZ1 or RIZ2, or fragments thereof that retain HMT activity, can be used in the invention methods.

The RIZ gene from several species has been cloned and characterized (Buyse et al., *Proc. Natl. Acad. Sci. USA* 92:4467–4471 (1995); Liu et al., supra (1997)). Accordingly, a RIZ polypeptide from any species can be used in the invention screening methods. The human RIZ gene encodes the RIZ1 amino acid sequence set forth as SEQ ID NO:1 (GenBank Accession No. AAC50820; gi:9955379) and the RIZ2 amino acid sequence set forth as SEQ ID NO:2. The rat RIZ gene encodes the RIZ1 amino acid sequence set forth in SEQ ID NO:3 (GenBank Accession No. AAA74468; gi:949996) and the RIZ2 amino acid sequence set forth as SEQ ID NO:4. The mouse RIZ gene has been partially sequenced (U.S. Pat. No. 5,811,304).

Human and rat RIZ1 and RIZ2 polypeptides are highly homologous over their entire lengths (see, for example, U.S. Pat. Nos. 6,323,335; 6,069,231; and 5,811,304). Because of this high degree of identity across two mammalian species, it is expected that other naturally occurring mammalian RIZ polypeptides, such as RIZ polypeptides from non-human primates, mouse, rabbit, bovine, porcine, ovine, canine or feline species, as well as naturally occurring RIZ polypeptides from other vertebrates, including fish, birds, reptiles and amphibians (e.g. *Xenopus*) will also exhibit a high degree of identity across their lengths with human and rat RIZ.

Using knowledge of the human or rat or RIZ-encoding nucleic acid sequences and polypeptides, those skilled in the art can readily clone RIZ-encoding genes from other species using conventional cDNA or expression library screening methods, or using the polymerase chain reaction (PCR). Additionally, using knowledge of the human or rat RIZ-encoding nucleic acid sequences and polypeptides, those skilled in the art can readily determine cDNA and coding sequences from other species from an analysis of ESTs and genomic sequences present in available databases. From these sequences, full-length RIZ1 or RIZ2 polypeptides, and fragments thereof with HMT activity, can be prepared for use in the screening methods disclosed herein.

A RIZ polypeptide useful in the methods of the invention can also have one or more minor modifications to the naturally occurring sequence, such as one or more substitutions, additions or deletions. A modified RIZ polypeptide will generally retain at least 70%, 75%, 80%, 90%, 95%, 98% or higher identity with a native RIZ sequence. Such modifications can be advantageous, for example, in enhancing the stability, bioavailability, bioactivity or immunogenicity of the polypeptide, or to facilitate its purification.

Substitutions to a RIZ amino acid sequence can either be conservative or non-conservative. Conservative amino acid substitutions include, but are not limited to, substitution of an apolar amino acid with another apolar amino acid (such as replacement of leucine with an isoleucine, valine, alanine, proline, tryptophan, phenylalanine or methionine); substitution of a charged amino acid with a similarly charged amino acid (such as replacement of a glutamic acid with an aspartic acid, or replacement of an arginine with a lysine or histidine); substitution of an uncharged polar amino acid with another uncharged polar amino acid (such as replacement of a serine with a glycine, threonine, tyrosine, cysteine, asparagine or glutamine); or substitution of a residue with a different functional group with a residue of similar size and shape (such as replacement of a serine with an alanine; an arginine with a methionine; or a tyrosine with a phenylalanine).

Additions to a RIZ amino acid sequence include, but are not limited to, the addition of "tag" sequences, which are conveniently added at the N- or C-termini, after the signal peptide, or within extracellular or intracellular loops. Such tag sequence include, for example, epitope tags, histidine tags, glutathione-S-transferase (GST), fluorescent proteins (e.g. Enhanced Green Fluorescent Protein (EGFP)) and the like. Such additional sequences can be used, for example, to facilitate expression, purification or characterization of the RIZ polypeptide.

Deletions to a RIZ amino acid sequence include, but are not limited to, deletion of residues at the N- or C-termini that are not critical for function. Deleted sequences can optionally be replaced by tag sequences or fusion sequences, as described previously.

Modifications to a RIZ amino acid sequence can be randomly generated, such as by random insertions, deletions or substitutions of nucleotides in a nucleic acid molecule encoding the polypeptide. Alternatively, modifications can be directed, such as by site-directed mutagenesis of a nucleic acid molecule encoding the polypeptide.

Guidance in modifying the sequence of a RIZ polypeptide while retaining biological activity can be provided by the alignment of the sequence of the RIZ orthologs from human and rat. It is well known in the art that evolutionarily conserved amino acid residues are more likely to be important for maintaining biological activity than less well-conserved residues. Thus, it would be expected that substituting a residue that is highly conserved among RIZ polypeptides across species with a non-conserved residue may be deleterious, whereas making the same substitution at a residue which varies among species would likely not have a significant effect on biological activity. An alignment of the rat and human RIZ1 amino acid sequences is presented in FIG. 10 of U.S. Pat. No. 5,811,304.

Computer programs well known in the art can also provide guidance in predicting which amino acid residues can be modified without abolishing a structural or functional feature of a RIZ polypeptide.

As disclosed herein, RIZ histone methyltransferase activity is present in an N-terminal, PR-domain containing portion specific to RIZ1. Accordingly, an exemplary RIZ or RIZ fragment useful in the methods of the invention contains amino acids 1–200 of RIZ1, such as amino acids 1–332 of RIZ1. A further exemplary RIZ or RIZ fragment useful in the methods of the invention contains amino acids 1–520 of RIZ1. In contrast, a RIZ fragment consisting of residues 1–161 of human RIZ1 lacked HMT activity, as did a RIZ1 containing missense mutations in the PR-domain found in tumors, namely C106Y, I88V and A159V.

Additionally, as disclosed herein, RIZ histone methyltransferase activity is also present in a C-terminal PR-binding domain (PBD) containing portion common to RIZ1 and RIZ2 (Huang et al., *J. Biol. Chem.* 273:15933–15940 (1988)). Accordingly, an exemplary RIZ or RIZ fragment useful in the methods of the invention contains amino acids 1514–1680 of RIZ1, such as amino acids 1514 to the C-terminus of RIZ1.

The HMT activity of other RIZ polypeptides and fragments, including polypeptides and fragment with modified sequences as described above, can readily be determined by the assays described herein in order to select a RIZ or RIZ fragment having histone methyltransferase activity for use in the screening methods.

As used herein, the term "histone methyltransferase activity" or "HMT activity," with respect to a RIZ or RIZ fragment, refers to the ability of the RIZ or RIZ fragment to catalyze the methylation of histones or histone peptides under suitable assay conditions. In contrast, under the same conditions, a control polypeptide, such as glutathione-S-transferase (GST), will not be able to catalyze the methylation of histones or histone peptides. HMT activity can be exhibited either in an in vitro assay with purified or partially purified RIZ, or in a cell-based assay. HMT activity includes HMT activity exhibited toward any histone, such as histone H1, H2A, H2B, H3 or H4.

Histones suitable for use as substrates in HMT activity assays can be obtained commercially (e.g. from Roche Molecular Biochemicals), prepared recombinantly based on known nucleic acid sequences, or extracted from cells using methods known in the art. Histone peptides suitable for use as substrates in HMT assays, including peptides with native sequences and peptides modified by acetylation on lysine residues, can be obtained commercially (e.g. from Upstate Biotech) or produced synthetically. Suitable histone peptides include, for example, H3 N-terminal peptides that include lys-9 (K9) (e.g. H3 amino acids 1–20) and H1 N-terminal peptides that include lys-25 (K25) (e.g. H1 amino acids 15–37 or 12–31). The methylation site on H4 is expected to be lys-20 (K20). Accordingly, a suitable histone H4 peptide can be an N-terminal peptide that includes lys-20.

For HMT assays, a RIZ or RIZ fragment of any desired sequence can conveniently be produced recombinantly, such as by expression of the encoding nucleic acid molecule in bacteria, yeast, insect or mammalian cells. The expressed polypeptide can then be isolated with anti-RIZ antibodies, or purified or partially purified by standard biochemical fractionation methods. Alternatively, to facilitate isolation, the RIZ polypeptide can be expressed as a fusion with a tag sequence, such as glutathione-S-transferase (GST), a 6×His tag or an epitope tag. Methods of producing and isolating tagged and untagged recombinant proteins are well known in the art (see, for example, Sambrook et al., *Molecular Cloning: A Laboratory Manual*, 3rd ed., Cold Spring Harbor Press, Plainview, N.Y. (2001); Ausubel et al. (*Current Protocols in Molecular Biology* (Supplement 47), John Wiley & Sons, New York (1999)).

As an alternative to preparing a recombinant RIZ or RIZ fragment, an endogenous RIZ1 or RIZ2 can be purified or partially purified from a convenient cell or tissue source. A RIZ fragment can thus be prepared by enzymatic or chemical cleavage of the endogenous RIZ. Alternatively, a RIZ fragment can be prepared by synthetic methods.

HMT activity of a RIZ can be determined by methods known in the art. For example, the RIZ and a histone or histone peptide can be incubated with a labeled methyl donor, such as S-adenosyl-[methyl-$^{14}$C]-L-methionine, or S-adenosyl-[methyl-$^{3}$H]-L-methionine, under suitable assay conditions. Transfer of the radiolabel to the histone or histone peptide can be detected, for example, by SDS-PAGE electrophoresis and fluorography. Alternatively, following the reaction the histone or histone peptides can be separated from the methyl donor by filtration, and the amount of radiolabel retained on the filter quantitated by scintillation counting. Other suitable labels that can be attached to methyl donors, such as chromogenic and fluorescent labels, and methods of detecting transfer of these labels to histones and histone peptides, are known in the art.

Alternatively, HMT activity of a RIZ can be determined using an unlabeled methyl donor (e.g. S-adenosyl-L-methionine) and reagents that selectively recognize methylated histones or histone peptides. For example, after incubation of the RIZ, methyl donor and histones or histone peptides, under suitable assay conditions, methylated histones or histone peptides can be detected by immunoblotting or by an ELISA assay with antibodies specific for methylated histone epitopes. Suitable antibodies are described, for example, in Nakayama et al., *Science* 292:110–113 (2001), Noma et al., *Science* 293:1150–1155 (2001) and published U.S. patent application Ser. No. 20020039776, or can be prepared by methods known in the art (see Harlow and Lane, *Antibodies: A Laboratory Manual*, Cold Spring Harbor Laboratory Press (1988)).

Instead of using antibodies, methylated histones can be detected using reagents that selectively bind methylated histones with high affinity. Such reagents are known in the art or can be determined by screening assays known in the art. An exemplary binding reagent is heterochromatin protein HP1, which binds histone H3 when methylated at lysine 9 (H3-K9). HP1, or a binding fragment thereof, can be labeled, and the HP1 or fragment bound to methylated H3-K9 detected. Alternatively, the HP1 or fragment need not be labeled, and can instead be detected using an anti-HP1 antibody in an ELISA assay.

Various low-throughput and high-throughput enzyme assay formats are known in the art and can be readily adapted for RIZ HMT assays. For high-throughput assays, the histone or histone peptide substrate can conveniently be immobilized on a solid support, such as a multiwell plate, slide or chip. Following the reaction, the methylated product can be detected on the solid support by the methods described above. Alternatively, the HMT reaction can take place in solution, after which the histone or histone peptide can be immobilized on a solid support, and the methylated product detected. To facilitate such assays, the solid support can be coated with streptavidin and the histone labeled with biotin, or the solid support can be coated with anti-histone antibodies. The skilled person can determine suitable assay formats depending on the desired throughput capacity of the screen.

The invention screening method involves contacting a RIZ or RIZ fragment having histone methyltransferase activity with one or more candidate compounds and assaying histone methyltransferase activity of the contacted RIZ or RIZ fragment. A candidate compound useful in the methods of the invention can be a naturally occurring macromolecule, such as a peptide, nucleic acid, carbohydrate, lipid, or any combination thereof. A candidate compound alternatively can be a partially or completely synthetic derivative, analog or mimetic of such a macromolecule, or a small, synthetic molecule, such as an organic molecule prepared by combinatorial chemistry methods. A candidate compound can be detectably labeled or attached to a solid support, if desired, as appropriate in a particular assay.

Methods for producing large libraries of compounds, including simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422–428 (1998); Tietze et al., *Curr. Biol.*, 2:363–371 (1998); Sofia, *Mol. Divers.* 3:75–94 (1998); Eichler et al., *Med. Res. Rev.* 15:481–496 (1995). Libraries containing large numbers of natural and synthetic compounds also can be obtained from commercial sources.

The number of different candidate compounds to screen in a particular assay can be determined by those skilled in the art, and can be 2 or more, such as 5, 10, 15, 20, 50 or 100 or more different compounds. For certain applications, such as when a library of random compounds is to be screened, and for automated procedures, it may be desirable to screen $10^3$ or more compounds, such as $10^5$ or more compounds, including $10^7$ or more compounds. If desired, a plurality of candidate compounds can be assayed in a pool, and the pool repeatedly subdivided until a single compound with the desired activity is identified. Candidate compounds can be assayed simultaneously, in parallel, or sequentially.

The amount of candidate compound to use in a reaction can be determined by the skilled person based on the nature of the compound, the nature of the assay, and the concentration of the reactants. If desired, a range of doses of candidate compound can be tested.

Generally, the candidate compound will be included in an HMT reaction together with the RIZ, histone or histone peptide substrate, and methyl donor. Optionally, the candidate compound and the RIZ can first be incubated together, and then the other reactants added. If desired, other components, such as different RIZ polypeptides or RIZ fragments, can be included in the reactions, and the effect of the candidate compound on modulating RIZ HMT activity under such conditions determined. The skilled person can determine suitable combinations of reactants and components.

For cell-based screening assays, a cell expressing a RIZ can be contacted with a candidate compound. Either the in vivo methylation of isolated histones can be determined following contacting, or the RIZ polypeptide can be isolated and its activity in methylating isolated histones or histone fragments assayed as described above. If desired, the ability of a candidate compound to modulate RIZ activity under physiologically relevant conditions can be determined in cell-based screening assays. For example, the ability of a candidate compound to module RIZ activity in the presence of estrogen or prpogesterone, in response to co-expressed polypeptides, or in tumor cells, can be determined.

Determining whether a candidate compound modulates RIZ HMT activity, either positively or negatively, generally requires comparison to a control. A control can be an identical reaction to the test reaction, except the control is not exposed to the candidate compound. The HMT activity of the control reaction can be assessed either before, after, or at the same time as the test reaction. A compound that "modulates" HMT activity is a compound that increases or decreases HMT activity, in comparison to a control, by at least 2-fold, such as at least 5-fold, 10-fold or more.

The results described in Example I suggest that the H3-K9 methylation activity of RIZ1 is linked with growth arrest, whereas its H1-K25 methylation activity is associated with cell proliferation. Accordingly, compounds that differentially regulate these two activities can be identified and used to promote or inhibit cell growth, as appropriate for a particular application.

As disclosed herein, RIZ1, but not RIZ2, acts as a transcriptional coactivator of the nuclear hormone receptors for the female sex steroids estrogen (ERα) and progesterone. Furthermore, RIZ1 is required for normal growth and development of female target organs, such as the uterus, vagina, and mammary gland, in response to estrogen and progesterone. Therefore RIZ1, and particularly the PR domain of RIZ1, is a physiologically important regulator of progesterone and estrogen receptor activity. Compounds that modulate RIZ1 activity are thus likely to also be able to modulate progesterone receptor and/or ERα activity. Such compounds can be used as therapeutics to prevent, ameliorate or treat conditions that are benefitted by modulated female sex steroid receptor activity, including reproductive conditions and cancer.

In one embodiment, the invention provides a method of screening for a compound that modulates progesterone receptor activity. The method is practiced by providing a RIZ1 modulatory compound, and determining the ability of the compound to also modulate progesterone receptor activity.

As used herein, the term "RIZ1 modulatory compound" refers to a compound that affects a RIZ1 biological activity, such as a binding interaction with a cellular molecule or an enzymatic activity (e.g. histone methyltransferase activity). A RIZ1 modulatory compound can thus be, for example, a compound that selectively binds RIZ1, a compound that modulates (by either increasing or decreasing) an interaction between RIZ1 and a binding partner, a compound that modulates a functional activity of RIZ1, or a compound with several of these effects.

Compounds that selectively bind RIZ1 are known in the art or can be identified by available screening methods. For example, compounds that selectively bind RIZ1 include RIZ1-specific antibodies (described, for example, in U.S. Pat. No. 5,811,304) and RIZ1 binding partners. As used herein, the term "RIZ1 binding partner" is intended to refer to a cellular molecule that normally binds with high affinity to a RIZ1, such as cellular proteins, nucleic acid molecules, enzymatic substrates and cofactors, the RIZ1-binding domains from these molecules, and RIZ1-binding variants and analogs of these molecules.

A "variant" of a RIZ1-binding partner has substantially the same amino acid or nucleotide sequence as the native molecule (e.g. at least 70%, 75%, 80%, 90%, 95%, 98% or higher identity), and retains substantially the same binding activity as the native molecule. In the case of a polypeptide, the polypeptide can have one or more conservative or non-conservative amino acid substitutions, additions or deletions compared to the naturally occurring sequence. Methods of preparing and assaying the binding activity of variants of RIZ1-binding partners are well known in the art.

An "analog" of a RIZ1-binding partner has substantially the same core chemical structure as the native molecule, and retain substantially the same binding activity as the native molecule. Methods of preparing and assaying the binding activity of analogs of RIZ1-binding partners are well known in the art.

An exemplary cellular protein that binds RIZ1 is the retinoblastoma protein (Rb). U.S. Pat. No. 5,811,304 describes the specific binding of RIZ1 to full-length Rb and to a C-terminal 56 kDa fragment of Rb that contains the Rb binding pocket (see also Buyse et al., *Proc. Natl. Acad. Sci. USA* 92:4467–4471 (1995)). Other cellular proteins that selectively bind RIZ1 include the estrogen receptor (ERα) (see Abbondanza et al., *Proc. Natl. Acad. Sci. USA* 97:3130–3135 (2000) and Example I) and progesterone receptor (PR) (see Example I). Additionally, GATA-3 (Shapiro et al., *Gene* 163:329–330 (1995)), p53, SRC1 and p300 are exemplary cellular proteins that selectively bind RIZ1.

Nucleic acid molecules that selectively bind RIZ1 are described, for example, in U.S. Pat. No. 5,811,304. Exemplary nucleic acid molecules to which RIZ1 selectively binds, through its zinc finger DNA binding motifs, contain GC-rich or Sp-1-binding elements.

Exemplary enzymatic substrates and cofactors that selectively bind RIZ1 include GTP (see U.S. Pat. No. 5,811,304), zinc ions (which associate with the zinc finger motifs) and S-adenosyl-methionine (SAM).

SAM acts as a substrate and methyl group donor for RIZ1 methyltransferase activity. Analogs of SAM include S-adenosyl-L or D-homocysteine (SAH), and adenosyl-L-ethionine. Other binding compounds can include, for example, A-adenosyl-gamma-thio-alpha-ketobutyrate, S-adenosyl-L-homocysteine sulfoxide, methythioadenosine (MTA), L-homocysteine, L-homoserine, Adenosine, Adenine, ATP, CAMP and methionine.

Therefore, any of the above compounds, or variants, analogs, agonists and antagonists of these compounds, can be assayed for their ability to modulate progesterone receptor activity by the methods of the invention.

Compounds that modulate the interaction between RIZ1 and a binding partner are also known in the art or can be identified by available screening methods. For example, U.S. Pat. No. 5,811,304 describes a 17 amino acid Rb binding peptide (101–118: T-pep) from the SV40 large T antigen as a compound that interferes with the interaction between RIZ1 and Rb. Other molecules that bind to a RIZ1 binding partner, or include a binding domain from a RIZ1 binding partner, are expected to be compounds that modulate the interaction between RIZ1 and a binding partner. Other compounds that can modulate the interaction between RIZ1 and a binding partner can contain a RIZ1 binding domain, and thus compete with full-length RIZ1 for the binding partner. RIZ binding domains include, for example, the LXXLL steroid receptor binding motif described herein, as well as the E1A-related region; the leucine-zipper; conserved regions 1 and 2; common epitope 1; zinc fingers; the GTPase domain; the SH3 domain; the SH3-binding domain; and the PMT (PR) domain, each of which is described in U.S. Pat. No. 5,811,304.

Other compounds that selectively bind RIZ1, or that modulate the interaction between RIZ1 and a binding partner, can be identified by either manual or high-throughput screening assays, starting from a library of known or unknown compounds, as described above.

A binding assay can use a detectably labeled candidate compound and an unlabeled RIZ1 (and optionally an unlabeled binding partner). Alternatively, a binding assay can use an unlabeled candidate compound or binding partner and a labeled RIZ1. Other appropriate combinations of labeled and unlabeled molecules can be determined by the skilled person depending on the assay format.

A variety of competitive and non-competitive binding assay formats for determining binding between molecules are known in the art. These assays include both-solution-based methods and solid phase methods (e.g. molecules bound to plates, chips, affinity columns and the like). Binding assays are amenable to either manual or high-throughput automated screening of compounds. Two exemplary binding assays are set forth in Example IIA and IIB.

Detectable labels can include, for example, a radioisotope, fluorochrome, ferromagnetic substance, or luminescent substance. Exemplary radiolabels useful for labeling compounds include $^{125}I$, $^{14}C$ and $^{3}H$. Methods, of detectably labeling organic molecules, either by incorporating labeled amino acids into the compound during synthesis, or by derivatizing the compound after synthesis, are known in the art.

RIZ1 functional activities are described herein or are known in the art. Exemplary activities include, for example, transcriptional activation (see, for example, U.S. Pat. No. 5,811,304), transcriptional repression (see, for example, Xie et al., *J. Biol. Chem.* 272:26360–26366 (1997)), histone methyltransferase activity (see Example I) and hormone receptor coactivation (see Examples I and II).

Suitable assays for identifying compounds that modulate RIZ1 transcriptional activation, repression and coactivation function can be determined by the skilled person. Such assays are generally based on co-expression of RIZ1 and an appropriate promoter-linked reporter gene in a cell, under conditions where a certain amount of transcription occurs, contacting the cell with the candidate compound, and determining whether there is a change (i.e. either an increase or decrease) in transcriptional activity. Transcription based assays are well known in the art, and readily amenable to high-throughput screening assays. Methyltransferase activity assays have been described above.

A compound that is identified as a RIZ1 modulatory compound by any of the above methods is then tested, in either an in vitro or in vivo assay, to determine whether it also modulates progesterone receptor activity. A compound that "modulates" progesterone receptor activity is intended to refer to a compound that either increases or decreases a PR biological activity.

The progesterone receptor is normally present in an inactive form in the cytoplasm, where it interacts with molecular chaperones, immunophillins, and heat shock proteins. The active PR binds progesterone and translocates to the nucleus where it binds as a transcription factor to canonical DNA transcriptional elements present in progesterone-regulated genes. As described herein, RIZ1 coactivates the transcriptional activity of PR. A compound that modulates progesterone receptor (PR) activity can thus be, for example, a compound that alters the interaction between PR and the molecules that normally hold it in an inactive form; alters the interaction between PR and progesterone; alters the interaction between RIZ1 and PR; or directly increases or decreases the transcriptional activity or specificity of PR toward PR-regulated genes.

Competitive and non-competitive binding assays have been described above with respect to RIZ1, and can be applied to identifying compounds that modulate PR interactions with progesterone, regulatory molecules or RIZ1. Assays that measure PR transcriptional activity can also be used to identify compounds that modulate PR activity. Conveniently, the progesterone response element (PRE) can be operatively linked to a reporter gene (e.g. luciferase, green fluorescent protein, beta-galactosidase and the like) and expressed in a cell, and an increase or decrease in expression of the reporter gene in response to a compound determined. Such an assay is described in Example I and IIC. Alternatively, a gene that is naturally induced by PR can be used in such assays, such as casein, and the mRNA or protein product detected.

Transcription-based assays, reporter genes, and methods for detecting gene expression, and methods of adapting these assays for high-throughput screening are well known in the art and described, for example, in Ausubel et al., *Current Protocols in Molecular Biology*, John Wiley and Sons, Baltimore, Md. (2001).

Other assays for compounds that modulate progesterone receptor activity include in vivo assays that report PR function, such as the assays for uterine, vaginal and mammary development described in Example I and IID. A change in development of these organs in response to treatment of the animal with a particular compound is consistent with the compound having an effect on PR activity.

Once identified, compounds that modulate progesterone receptor activity can be formulated as pharmaceutical compositions and used to prevent or treat reproductive and endocrinological disorders and cancers. Such disorders can include, for example: infertility, tubal disease, ovulatory defects, endometriosis, disruptions of the estrous cycle, disruptions of the menstrual cycle, polycystic ovary syndrome, ovarian hyperstimulation syndrome, endometrial and ovarian tumors, autoimmune disorders, ectopic pregnancy, teratogenesis, cancer of the breast, fibrocystic breast disease, galactorrhea, disruptions of spermatogenesis, abnormal sperm physiology, cancer of the testis, cancer of the prostate, benign prostatic hyperplasia, prostatitis, carcinoma of the male breast and gynecomastia. Other conditions in which increasing or decreasing progesterone receptor activity would be beneficial are known in the art or can be determined by the skilled person. The invention thus provides for the administration of a pharmaceutical composition containing a compound that modulates progesterone receptor activity, to prevent or ameliorate any of the disorders and conditions described above.

The pharmaceutical compositions of the invention, which include compounds that modulate RIZ1 HMT activity, and compounds that modulate progesterone receptor activity, may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Pills, capsules, tablets and the like may further contain suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the pills or coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. Such labeling can include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, or in animal models, usually mice, rats, rabbits, dogs, or pigs. The animal model may also be used to determine the appropriate concentration range and route of administration. Such information can then be used to determine useful doses and routes for administration in humans.

A therapeutically effective dose refers to that amount of active ingredient which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks-depending on half-life and clearance rate of the particular formulation.

Normal dosage amounts may vary from 0.1 $\mu$g to 100 mg, up to a total dose of about 1 g, depending upon the route of administration. Guidance as to particular dosages and methods of delivery is provided in the literature and generally available to practitioners in the art.

As disclosed herein, RIZ1 is an estrogen receptor coactivator. RIZ1 silencing is significantly more common in ER-negative breast cancers compared with ER-positive breast cancers, and appears to be implicated in the acquisition of estrogen resistance, since nearly half of ER+ cancer tissues examined were determined to be RIZ1 expression-negative.

The action of estrogen is mediated via interaction with a specific receptor (ER) that initiates a series of downstream events, leading to the modulation of hormone-responsive genes and cell proliferation. Endocrine therapy, including both surgical and medical therapies to reduce estrogen action, is the preferred, first-line therapy in patients with ER+ cancers.

However, a large percentage of patients with ER-positive tumors do not respond to endocrine therapy. The determination that RIZ1 inactivation is highly associated with decreased estrogen responsiveness in breast cancer cells allows RIZ1 status to be used to predict whether an individual with an ER+ tumor is likely to respond to endocrine therapy.

Based on information regarding RIZ1 status, a clinician can determine a suitable treatment for the particular individual that is more likely to be effective in prolonging disease-free survival and/or reducing mortality, while avoiding exposing the individual to unnecessary treatments with potential side effects. For an individual determined by the invention method to have a normal likelihood of responding to endocrine therapy, endocrine therapy is appropriate.

However, for an individual determined by the invention method to have a reduced likelihood of responding to endocrine therapy, an alternative treatment can be chosen from among the available treatment options. Alternatively, for such an individual, endocrine therapy can be combined with an additional treatment.

The nature of an alternative or additional treatment for such an individual can be chosen by the clinician depending on the type and stage of tumor, extent of metastasis, overall health of the individual and other concurrent treatments. For example, in an individual determined to have a reduced likelihood of responding to endocrine therapy, chemotherapy, surgery or radiation can be combined with, or used as an alternative to, endocrine therapy.

Accordingly, the invention provides a method of identifying an individual with an estrogen receptor positive (ER+) tumor having a reduced likelihood of responding to endocrine therapy. The method is practiced by determining the RIZ1 status of the tumor, wherein an abnormal RIZ1 status identifies the individual as an individual with a reduced likelihood of responding to endocrine therapy. A normal RIZ1 status identifies the individual as an individual with a normal likelihood of responding to endocrine therapy.

As used herein, the term "endocrine therapy" refers to a therapy that reduces the proliferative potential of estrogen. Endocrine therapy can be either surgical or medical, and affect any aspect of estrogen action, including estrogen production and estrogen receptor signaling.

Methods of ablating estrogen production include surgical removal or irradiation of the ovaries, which are the primary source of estrogen in premenopausal women. Ablation of estrogen production can also be achieved pharmacologically by using luteinizing hormone-releasing hormone or gonadotropin-releasing hormone agonists.

Selective estrogen receptor modulators (SERMs) refer to compounds that blunt or block the effects of an estrogen agonist, such as 17β-estradiol, when administered concomitantly in a test system. SERMs used in cancer therapy, although commonly known as "anti-estrogens," generally exhibit a combination of anti-estrogenic and estrogenic effects. The antagonist effect of tamoxifen, the most widely used SERM, is a result of blocking the transmission of E2-ER-initiated signals for cell proliferation. Other SERMs include 4-hydroxytamoxifen and related triphenylene antiestrogens; clomiphene; and non-uterotrophic antiesestrogens, such as raloxifene, droloxifene, idoxifine, nafoxidine, toremifene, TAT-59, levomeloxifene, LY-353381, CP-336156, MDL-103323, EM-800, ERA-923, ICI-182,780 and the like. Other SERMs are known in the art or can be determined.

Aromatase inhibitors are also used in endocrine therapy for ER+ cancers in postmenopausal women. Aromatase catalyzes the final step in the synthesis of the estrogens estrone and estradiol from androgens and, therefore, inhibitors of aromatase reduce estrogen production. Exemplary aromatase inhibitors include aminoglutethimide, megestrol acetate, anastrozole, letrozole and exemestane.

As used herein, the term "estrogen receptor positive (ER+) tumor" refers to a tumor that expresses estrogen receptors above an art-recognized threshold level. A number of assays are routinely used in the art to categorize a tumor as ER+ or ER−. Such assays include, for example, ligand binding assays (LBA) and immunohistochemistry (IHC). Conveniently, immunohistochemistry can allow for simultaneous determination of ER status and RIZ1 status of a tumor, as described herein. Generally, an ER level of greater than 3 fmol/mg cytosolic protein by an LBA is considered ER+, whereas greater than 1% positive cells by an IHC assay is considered ER+ (Harvey et al., *J. Clin. Oncol.* 17:1474–1481 (1999); Elledge et al., *Int. J. Cancer (Pred. Oncol.)* 89:111–117 (2000)). A cutoff of 10% positive cells was considered ER+ in the immunohistochemical assays described in Example I. However, the results would not have changed significantly using a 1% cutoff.

As used herein, the term "tumor" refers to a malignant neoplasm. A tumor can be either a primary lesion or a metastatic lesion. Tumors that have been shown to express estrogen receptors include breast carcinoma, endometrial carcinoma, prostate carcinoma, ovarian carcinoma, renal carcinoma, melanoma, colorectal tumors, desmoid tumors, pancreatic carcinoma, and pituitary tumors. The methods of the invention are applicable to ER+ tumors of any of these types, as well as other tumors determined to be ER+. The methods of the invention are applicable to ER+ cancers at any clinical stage, including localized cancers, cancers with regional spread and cancers with distant spread.

Additionally, the method can be practiced with respect to individuals whose tissues upon biopsy are determined not to be malignant, including tissues that are determined to be normal or precancerous. An abnormal RIZ1 status in such ER+ tissues is predictive of an increased likelihood of the individual developing a tumor in that tissue. In particular, in women with low amounts of circulating estrogen, including post-menopausal women and women whose ovaries have been removed, an abnormal RIZ1 status in ER+ tissues is predictive of an increased likelihood of the individual developing a tumor in that tissue. For such individuals, prophylactic treatment, other than endocrine therapy, can be warranted. Suitable prophylactic treatments, including lifestyle changes (e.g. diet and exercise) and drug treatments, can be determined by those skilled in the art.

As used herein, the term "status" with respect to RIZ1 refers to a measurable property that is correlated with RIZ1 polypeptide function in the tumor. The measurable property that is determined can be a property of the RIZ1 polypeptide or of the encoding RIZ1 gene or mRNA.

An exemplary measurable property correlated with RIZ1 polypeptide function in the tumor in the tumor is the amount of the RIZ1 gene, mRNA or polypeptide in the tumor. An "abnormal RIZ1 status" in this case can thus be a decreased amount, in the tumor sample, of the RIZ1 gene, mRNA or polypeptide. Generally, a decreased amount of the RIZ1 gene, mRNA or polypeptide in the tumor refers to at least an 80% reduction, such as a 90% reduction, in the amount of the RIZ1 gene, mRNA or polypeptide in the tumor sample, relative to the amount in a control sample. The skilled person can determine an appropriate control for a,particular assay, such as nearby normal tissue from the same individual, or a tumor sample previously identified as having a normal amount of the RIZ1 gene, mRNA or polypeptide.

A further exemplary measurable property correlated with RIZ1 polypeptide function in the tumor is the structural integrity of the RIZ1 gene. An "abnormal RIZ1 status" in this case can thus be a mutation in the normal nucleotide sequence of the RIZ1 gene in the tumor sample. Such a mutation can be determined directly by sequencing all or selected portions of the RIZ1 gene or mRNA. A mutation in the RIZ1 gene sequence can also be inferred indirectly, such as by detecting an alteration in the normal size or abundance of the RIZ1 mRNA, an alteration in the normal ratio of RIZ2/RIZ1, or by detecting an alteration in the normal size, stability or localization of the RIZ1 polypeptide product.

Mutations that can affect the ability of the RIZ1 polypeptide to be expressed or function normally include, for example, genomic deletions, frameshift mutations (Chadwick et al., *Proc. Natl. Acad. Sci. USA* 97:2662–2667 (2000); Piao et al., *Cancer Res.* 60:4701–4704 (2000); Sakurada et al., *Genes, Chroms. Cancer* 30:207–211 (2001)), missense mutations, nonsense mutations, and mutations in regulatory regions (U.S. Pat. No. 5,811,304).

Methods for determining the amount or structural integrity of a particular gene, mRNA or polypeptide in a sample are well known in the art and described, for example, in Sambrook et al., *Molecular Cloning: A Laboratory Manual*, 3rd ed., Cold Spring Harbor Press, Plainview, N.Y. (2001); Ausubel et,al. (*Current Protocols in Molecular Biology* (Supplement 47), John Wiley & Sons, New York (1999)). The particular method for a given application can be chosen by the skilled person. Exemplary methods include, for example, DNA sequencing, SSCP, Southern blotting, PCR, Northern blotting, RT-PCR, RNAse protection, in situ hybridization, immunohistochemistry, immunoblotting and immunoprecipitation. Reagents suitable for detecting RIZ1 nucleic acid molecules in these methods, such as hybridization probes and PCR primers, are known in the art and described, for example, in He et al., *Cancer Res.* 4238–4244 (1998) and in the Example herein. Reagents suitable for detecting RIZ1 polypeptide in these methods, such as the KG7.1S and 2D7 antibodies, are also known in the art and described, for example, in Buyse et al. *Proc. Natl. Acad. Sci. USA* 92:4467–4471 (1995).

Another exemplary measurable property correlated with RIZ1 polypeptide function in the tumor is the extent of methylation of the RIZ1 gene promoter. As described in Du et al., *Cancer Res.* 61:8094–8099 (2001), partial or complete methylation of the 35 CpGs in the RIZ1 promoter is strongly correlated with reduced RIZ1 mRNA expression, which in turn results in reduced RIZ1 polypeptide abundance. An "abnormal RIZ1 status" in this case can thus be partial or complete RIZ1 promoter CpG methylation.

RIZ1 promoter methylation can be determined, for example, by the methods described in Du et al., supra (2001). Briefly, one method involves treating genomic DNA from a sample with bisulfite, amplifying the RIZ1 promoter DNA using polymerase chain reaction (PCR), followed by cloning and sequencing the amplified product. Bisulfite treatment converts unmethylated cytosines to uridine, whereas methylated cytosines are resistant to conversion. An exemplary primer set suitable for RIZ1 promoter amplification by this method is 5'-GGTTGGGTGGTGGTTATTGGG-3' (SEQ ID NO:5) and 5'-CAAAAACCGCCCTGCGCCACTCCTTACC-3' (SEQ ID NO:6). An alternative method involves treating genomic DNA from a sample with bisulfite and amplifying the DNA using methylation-specific polymerase chain reaction (MSP) with RIZ1 specific primers. An exemplary primer set for selectively amplifying methylated RIZ1 promoter DNA is 5'-GTGGTGGTTATTGGGCGACGGC-3' (SEQ ID NO:7) and 5'-GCTATTTCGCCGACCCCGACG-3' (SEQ ID NO:8), whereas an exemplary primer set for selectively amplifying unmethylated RIZ1 promoter DNA is 5'-TGGTGGTTATTGGGTGATGGT-3' (SEQ ID NO:9) and 5'-ACTATTTCACCAACCCCAAGA-3' (SEQ ID NO:10).

Another exemplary measurable property correlated with RIZ1 polypeptide function in the tumor is histone methyltransferase activity of the RIZ1 polypeptide. An "abnormal RIZ1 status" in this case can thus be altered H1-K25 methylation activity, altered H3-K9 methylation activity, or an alteration in the normal RIZ activity toward another identified histone methylation site. Such an alteration can be either increased or decreased HMT activity, relative to a normal control. Histone methyltransferase assays have been described above, and can be adapted by the skilled person for determining histone methyltransferase activity of a RIZ1 polypeptide in a tumor sample.

The skilled person can determine other measurable properties correlated with RIZ1 polypeptide function in the tumor, which can be used in the invention method to determine RIZ1 status. If by any of these criteria it is determined that the RIZ1 polypeptide would be unlikely to function normally in the tumor, whether because of altered amount, structure or activity, the tumor is designated as having an "abnormal RIZ1 status," and the individual identified as having a "reduced likelihood of responding to endocrine therapy." Accordingly, alternatives to endocrine therapy, or the use of endocrine therapy in combination with other therapies, are warranted in such an individual to improve the chance of disease-free and overall survival.

The following examples are intended to illustrate but not limit the present invention.

EXAMPLE I

This example shows that the tumor suppressor gene RIZ1(PRDM2) is a member of the histone methyltransferase superfamily and a coactivator of female sex hormone receptors. This example also shows that RIZ1 mediates female sex hormone action in vivo, and that loss of its function is involved in the transition to hormone resistance and hormone independent growth of breast cancer.

Materials and Methods

Plasmids and Transient Transfections

The human RIZ1 and RIZ2 expression vectors and RIZ1 mutant vectors used are described in Steele-Perkins et al., *Genes Dev.* 15:2250–2262 (2001). The mammalian RIZ1 expression vector p3RIZ1RH4.1 was constructed by cloning the full-length wild type human RIZ1 cDNA into the pcDNA3 vector (Invitrogen). The vector p3RIZ1 RH4.1-L965A containing a missense mutation (leucine to alanine) was generated by the Quick-Change mutagenesis kit (Stratagene), and verified by DNA sequencing. Expression vectors of RIZ proteins and expression vectors containing full length mammalian ERα, PR, RARα, RXRα, VDR, AR, TR and GR were cotransfected into CV-1 cells with an appropriate reporter construct containing a synthetic hormone response element linked to the tk-CAT reporter. The reporter TREpal-tk-CAT containing a synthetic response element for RAR, RXR and TR (Zhang et al., *Nature* 355:441–446 (1992)) was used to evaluate effects of RARα, RXRα, and TR, the GRE-tk-CAT (Zhang et al., *J. Biol. Chem.* 266:8248–8254 (1991)) for GR and AR, the ERE-tk-CAT (Lee et al., *Mol. Cell. Biol.* 15:4194–4207 (1995)) for ERα, the PRE-tk-cat for PR (McKay and Cidlowski, *Mol. Endocrinol.* 12:45–56 (1998)), and the VDRE-tk-CAT (Agadir et al., *Carcinogenesis* 20:577–582 (1999)) for VDR.

A calcium phosphate precipitation procedure was used for transient transfection as described previously (Lee et al., *Mol. Cell. Biol.* 15:4194–4207 (1995)). Briefly, 0.5–1.0×10$^5$ cells/well were seeded in 24-well plates, and 50–400 ng of RIZ plasmids, 100 ng of expression vectors for NHRs, 100 ng of reporter plasmid, and 100 ng of a β-gal expression vector were mixed with carrier DNA to 1 μg of total DNA/well. Transfections of MCF-7 cells (2×10$^5$ cells/well in 6-well plates) used the Effectene Transfection Reagent (Qiagen), according to the manufacture's instructions. Cells were treated with or without the indicated hormone (50 nM for estradiol (E2), and 100 nM for R5020 (synthetic P agonist), all-trans retinoic acid (all-trans-RA), 9-cis retinoic acid (9-cis-RA), 1,25 dihydroxyvitamin D3 (VD3), dihydrotestosterone (DHT), triiodothyronine (T3), and dexamethasone (DEX); all from Sigma except R5020 which was from NEN) for 24 h. and CAT activity was measured as described (Lee et al., *Mol. Cell. Biol.* 15:4194–4207 (1995)). CAT values were normalized for transfection efficiency by the corresponding β-gal activity.

Plasmids used for GST protein production were constructed by PCR cloning as follows. To express human RIZ1 protein 1–200 residue region, full length human RIZ1 cDNA plasmid was used as template for PCR (Pfu polymerase, Stratagene) by primers hRP109.2 (AAA CCA TGG ATC AGA ACA CTA CTG AG (SEQ ID NO:11)) and RP274 (CCG TAA GCT TCA TGC AGA GGT GAA ATC TGG C (SEQ ID NO:12)). The PCR fragment was cloned into the NcoI and HindIII sites in the vector pKG-PBR (Huang et al., *J. Biol. Chem.* 273:15933–15940 (1998b)) to generate pKG-HN1. BL-21 cells were transformed by pKG-HN1 to produce the GST-RIZ200 protein. To express RIZ1 protein 1–161 residue region, a stop codon was introduced at residue 162 in the plasmid pKG-HN1 by using the Quick-Change mutagenesis kit (Stratagene). The primers used were RP296P1 (CGA GCC AGC GCC CGG AGC TAA GCT TAA GCG GAG CTC CCC (SEQ ID NO:13)) and RP296P2 that has the compliment sequence of RP296P1. To generate missense mutant GST-RIZ200 proteins, mutagenesis by Quick-Change was performed on the pKG-HN1 plasmid template using primers as described previously (Steele-Perkins et al., *Genes Dev.* 15:2250–2262 (2001)). To generate longer peptide fragments of RIZ1 in bacteria, the N-terminal 520-residue fragment was first cloned into the Nco1 and HindIII sites of PKG-PBR vector by PCR to generate the plasmid pKGH205. However, this plasmid did not give high yields of the expected protein product. Next, a stop codon was introduced into this plasmid by Quick-change mutagenesis to generate pKGRIZ332, which then produced high yields of the RIZ1 N-terminus 332-residue peptide. The PCR primers used for mutagenesis are: RP307: GAT TTA TTA GAG GAA tgA AAA ACA ACT TCA GAA G (SEQ ID NO:14), and RP308: CTT CTG AAG TTG TTT TTc aTT CCT CTA ATA AAT C (SEQ ID NO:15).

Immunoprecipitation and Immunoblot

MCF-7 and T47-D breast cancer cells were grown in 15 cm dishes in DMEM with 5% FCS, and 2 mM L-glutamine. Subconfluent cells (4×10$^6$) were then cultured in DMEM without phenol red, serum or hormones for an additional 3 days, during which media was changed twice daily. Cells were incubated for 24 h with or without hormones (50 nM for E2 and 100 nM for R5020) and infected with an adenovirus vector containing RIZ1 (AdRIZ1; at a concentration of 1×10$^{10}$ viral particles/15 cm dish) or the empty vector (AdNull) (He et al., *Cancer Res.* 58:4238–4244 (1998)). Cells were then grown for an additional 48 h in DMEM without phenol red supplemented with 5% charcoal-treated FCS (Omega Scientific). Cells were harvested and proceeded to immunoprecipitation and immunoblot essentially as described (Buyse et al., *Proc. Natl. Acad. Sci. U.S.A.* 92:4467–4471 (1995); Liu et al., *J. Biol. Chem.* 272:2984–2991 (1997)). Antibodies used included RIZ monoclonal antibody 2D7 (Buyse et al., *Proc. Natl. Acad. Sci. U.S.A.* 92:4467–4471 (1995)), monoclonal antibodies versus ERα (sc-8005, Santa Cruz Biotechnology), progesterone receptor (1A6, DAKO). For histone methylation analysis, anti-dimethyl-H3-K9 and anti-dimethyl-H3-K4 antibodies (Upstate Biotech) were used for immunoblot analysis of acid extracted histones from cells infected with control and AdRIZ1 viruses for 48 hr. For H1 phosphorylation analysis, anti-phosph-H1 and anti-H1 antibody (Upstate Biotech) were used for immunoblot analysis of acid extracted histones.

Mice

RIZ1–/–mice were generated as described in Steele-Perkins et al., *Genes Dev.* 15:2250–2262 (2001). Briefly, a PR-domain-encoding cDNA fragment of rat RIZ1 cDNA was used to screen a mouse 129Sv genomic library (Stratagene) to obtain mouse genomic DNA. The targeting construct was designed to insert the PGK-neo$^r$-BpA cassette (Soriano et al., *Cell* 64:693–702 (1991)) into exon 5 and to place the Herpes Simplex Virus TK cassette from PMC1-TK (Mansour et al., *Nature* 336:348–352 (1988)) external and adjacent to the region of homology. The targeting plasmid was linearized by XhoI digestion and electroporated into D3 ES cells (Gossler et al., *Proc. Natl. Acad. Sci. USA* 83:9065–9069 (1986)). The ES clones were selected in media containing G418 (150 µg/ml) and ganciclovir (2.0 µM). Homologous recombination events were screened by Southern blot analysis with XbaI digestion and hybridization to the 0.5-kb XbaI-BglII 5' probe or with NotI plus EcoRI digestion and hybridization to the 0.5-kb SacII-NotI 3' probe. Five RIZ1+/–ES cell-lines were microinjected into C57BL/6 blastocysts that were implanted subsequently into the uteri of Balb/c foster mothers. Male chimeric mice generated from two RIZ1+/–ES clones transmitted the RIZ mutation into germline. The presence of the RIZ1 mutant allele in the F1 animals was confirmed by Southern blotting and polymerase chain reaction (PCR) analysis of genomic DNA from the tail of animals. RIZ1+/–F1 animals were bred together to generate RIZ1–/–mice.

To examine reproductive functions, female RIZ1–/–mice were bred with male RIZ1+/–mice, female RIZ1+/–mice were bred with male RIZ1–/–mice, and breedings between heterozygous mutants were also performed. The number of litters was recorded, and all mice were routinely measured for body weight throughout the studies.

Analysis of Gene Expression

For RIZ staining, the RIZ rabbit antiserum KG7.1S (Buyse et al., *Proc. Natl. Acad. Sci. U.S.A.* 92:4467–4471 (1995)) was used at an optimal dilution of 1/200. For ERα staining the polyclonal rabbit anti-ERα antibody (sc-542 Santa Cruz) was used at a dilution of 1/250, and for PR staining the polyclonal rabbit anti-PR antibody (A0098 DAKO) was used at a dilution of 1/100, essentially as described (Tibbetts et al., *Biol. Reprod.* 59:1143–1152 (1998)). Tissues were fixed in Bouin's solution and processed by routine methods for embeddement in paraffin and sectioning (5 µm). For RIZ and ER staining, sections were treated with trypsin (Zymed), whereas for PR staining, the sections were subjected to treatment using the Target Retrieval Solution (DAKO), all performed according to the manufacture's instructions. Sections were then incubated with the primary antibody followed with a biotinylated secondary antibody. The localization of the primary antibody was visualized with the imidazole-DAB reaction producing a brown colored stain, followed by hematoxyline counterstaining and routine processing for bright-field microscopy analysis. Negative controls included omission of the primary antibodies and incubation with the preimmune KG7.1S antiserum, whereas colorectal xenograft tumors infected with AdRIZ1 were used as positive control for RIZ expression (Jiang and Huang, *Cancer Res.* 61:1796–1798 (2001)).

For RT-PCR analysis of RIZ gene expression, tissues from 7-week old RIZ1+/+mice were pulverized in liquid nitrogen and total RNA was isolated using the TRIZOL reagent (Gibco BRL). cDNA was synthesized using the first strand cDNA synthesis kit (Gibco BRL). Oligos RP260 (5'-CTC ATT CAT CTA AGA AAG GTG G-3'; SEQ ID NO:16)+RP259 (5'-TGA TTC CAG GTC ACT TCA GG-3'; SEQ ID NO:17) and RP170 (5'-GAA GCC AAA GGC CTC TCA TC-3'; SEQ ID NO:18)+K05 (5'-AGA CTC TGG CTG AGG TAC C-3'; SEQ ID NO:19) were used in standard PCR conditions encompassing 30 cycles at an annealing temperature of 59° C. to amplify the RIZ1+2 and RIZ1 specific fragments, respectively.

Analysis of Target Organs in Response to Hormone Treatments

Figure 4:
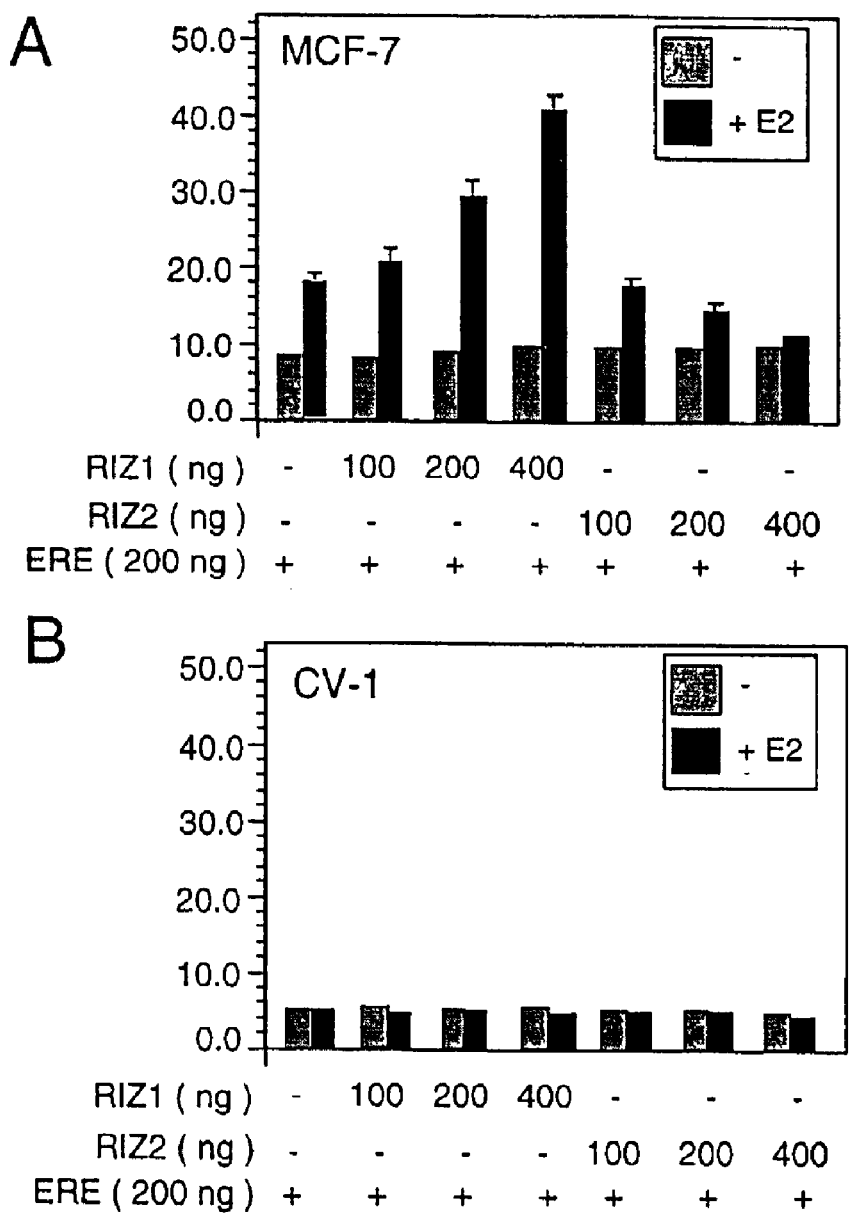
FIG. 4 shows modulation by RIZ of E2-dependent transcription mediated by endogenous ER. MCF-7 cells (A) and CV-1 cells (B) were cotransfected with the reporter ERE-tk-CAT and either RIZ1 or RIZ2 expression plasmids. Cells were treated with or without E2 and assayed for CAT activity. Data shown represent the means±SEM of three independent experiments.

To investigate E2-mediated increments in proliferation and hyperemia of uteri and changes in the cellular organization of the vaginal epithelium (Xu et al., *Science* 279:1922–1925 (1998)), 8-week old female RIZ−/− and RIZ+/+mice were ovariectomized (OVXed). At day 15–17 following OVX, mice were treated with S.C. injections of E2 (0.8 ng/g/day; Sigma) or with the vehicle (0.1 ml corn oil) alone for three days. The mice were then sacrificed at day 18 and the uterine wet weight was measured, and vaginal tissue was collected. The tissues were processed as above and vaginal specimens were stained with routine H & E and uterine specimens for PR expression. The thickness of the vaginal epithelium and the cornified layer was photographed and measured as described in FIG. 4 using the Spot 3.2.4. software (Diagnostic Instruments).

To evaluate the P- and E2-mediated decidual response a previously described protocol was used (Lydon et al., *Genes Dev.* 9:2266–2278 (1995)); Xu et al., *Science* 279:1922–1925 (1998)). Briefly, 8 week old female mice were OVXed and at day 10–12 following OVX, mice were treated with S.C. injections of E2 in corn oil (100 ng/day), then treated with P (1 mg/day; Sigma)+E2 (6.7 ng/day) from day 16–23. Six h after the third P+E2 injection on day 18, the left uterine horn (right horn served as a control) was traumatically stimulated by insertion of a burred needle proximal to the cervix and longitudinally scratching the entire length of the uterine horn antimesometrially. The mice were sacrificed on day 23, six hour after the last P+E2 injection, and the wet weights of the left and right uterine horns were measured.

To measure effects on mammopoiesis by normal development, pregnancy, and female sex hormone treatment the following protocols were used (Xu et al., *Proc. Natl. Acad. Sci. USA* 97:6379–6384 (2000); Xu et al., *Science* 279:1922–1925 (1998)). To determine the effects of normal pubertal development on mammary gland growth, 7 week old virgin female mice were sacrificed. Additionally, pregnant female mice at day 19 of first pregnancy were sacrificed. To examine the effects of E2+P treatments on mammary gland development, 8 week old female mice were OVXed and at 14 days following OVX treated with S.C. 21-day releasing hormone pellets containing 0.1 mg of E2 and 10 mg P4 or S.C. placebo pellets (Innovative Research of America). On day 35, the mice were sacrificed and the uterus was wet weighed and analyzed microscopically to ensure actual hormone release. In all cases, whole mounts were prepared from the fourth mammary gland and carmine-stained according to standard procedures(Evans et al., *Oncogene* 19:989–991 (2000)), and the relationship between mammary ducts and mammary fat pad, extent of branching as well as number of branches were investigated microscopically.

In order to evaluate the response to testosterone, twelve week old male mice were orchiectomized (ORCed) and testicles were wet weighed (Xu et al., *Science* 279:1922–1925 (1998)). Nine days following ORC, mice were treated during days 9–15 with S.C. injections of testosterone (3 mg/kg/day, Sigma) or vehicle alone (0.1 ml corn oil). On day 16, mice were sacrificed and the prostate and the pars prostate of the urethra (for technical reasons) were removed and wet weighed.

Statistical Analysis

Student's unpaired t-test was used for statistical evaluation of means, with P<0.05 considered to be significant. All results are expressed as mean±SEM (standard error of the mean) or mean±SD (standard deviation, when stated). Fisher's exact test was used for evaluation of the difference between ER-negative and ER-positive breast cancers, with P<0.05 considered to be significant.

Methylation Assays

Methylation reactions (30–40 $\mu$l) contained 20 mM Tris-HCl (pH8.0), 0.2 M NaCl, 0.4 mM EDTA, affinity-purified GST-RIZ1 or immunoprecipitation products, free histones (20–40 $\mu$g) purified from acid extraction of human cancer cells (A549 or U2OS), and 3 $\mu$l (1.65 $\mu$Ci and 21 pmole) [methyl-$^3$H]-adenosyl-methionine (Amersham-Pharmacia). Nuclear extracts were prepared according to standard procedures and used for immunoprecipitation. Antisera used for immunoprecipitation were anti-KG7.1S and preimmune serum as described previously (Buyse et al., *Proc. Natl. Acad. Sci. U.S.A.* 92:4467–4471 (1995)). Similar HMT activity has also been observed with immunoprecipitates using a different serum (data not shown), 1715, which was described previously (Steele-Perkins et al., *Genes Dev.* 15:2250–2262 (2001)). Various amount of SAH (Sigma) were added in some methylation reactions.

To determine the methylated residues on H3 and H1, H3 N terminus 1–20 residue peptides (Upstate Biotech), non-acetylated and acetylated on K9 and K14, and H1 N terminus 15–37 and 12–31 peptides were used as substrates for in vitro methylation reactions as described above. The reactions were resolved on Tris-Tricine 10–20% gel (Invitrogen) followed by fluorography. The $^3$H-labelled H3 or H1 peptides were purified by HPLC and sequenced from the amino termini in an Applied Biosystems model 477A Protein Sequencer. After conversion, the samples were collected for determination of radioactivity by scintillation counting.

Histones from nocodazole treated cells were isolated by acid extraction of U2OS cells treated for 48 hour with 50 ng/ml nocodazole. Histones (20 mg) were treated with lambda protein phosphatase (400 U) (New England Biolabs) for 1 hr at 30° C. in buffer. Control histones were treated the same except that phosphatase was omitted from the incubation mixture.

Results

RIZ1 is a Specific Coactivator of ER and Progesterone Receptor

RIZ1 has been shown to be a coactivator of estrogen receptor (ER) (Abbondanza et al., *Proc. Natl. Acad. Sci. USA* 97:3130–3135 (2000); Steele-Perkins et al., *Genes Dev.* 15:2250–2262 (2001)). To better understand the coactivator function of RIZ1, the effects of RIZ1 on ER were compared with its effects on several other NHRs. As shown in FIG. 1A, RIZ1 enhanced ER and progesterone receptor (PR) function in a ligand- and dose-dependent manner. In contrast, RIZ1 had no major effects on the activities of androgen receptor, retinoic acid receptor a (RAR$\alpha$), retinoic X receptor $\alpha$ (RXR$\alpha$), thyroid hormone receptor (not shown), glucocoticoid receptor (not shown), and vitamin D receptor (not shown). Similar to what has been found with ER (Steele-Perkins et al., *Genes Dev.* 15:2250–2262

(2001)), RIZ2 and RIZ1 missense mutants (C106Y and I188V) failed to coactivate progesterone receptor (FIG. 1A). The introduction of a point mutation in the LXXLL motif of RIZ also produced a protein unable to act as a coactivator for progesterone receptor (FIG. 1A). Consistent with RIZ1 effects on ER and progesterone receptor, protein complexes containing RIZ1 and these receptors were detected by a coimmunoprecipitation assay (FIG. 1B). Thus, RIZ1 is a specific coactivator of estrogen receptor and progesterone receptor but not for other nuclear hormone receptors, and the intact PR/SET-domain of RIZ1 is essential for its function.

To confirm the expected RIZ expression in the target organs of E2 and progesterone, RIZ expression was determined by immunohistochemistry. The gene products displayed nuclear staining in the uterus, including both glandular and luminal epithelium as well as stromal and myometrial cells, similar to the expression of ER (FIG. 1C). Additionally, RIZ is expressed in both mammary and vaginal epithelium. For these experiments, the serum anti-KG7.1S, which recognizes both RIZ1 and RIZ2, was used (Buyse et al., Proc. Natl. Acad. Sci. USA 92:4467–4471 (1995); Liu et al., J. Biol. Chem. 272:2984–2991 (1997)). Positive results from this antibody likely reflect expression of both proteins because they are coexpressed in most tissues (Buyse et al., Proc. Natl. Acad. Sci. USA. 92:4467–4471 (1995); Liu et al., J. Biol. Chem. 272:2984–2991 (1997)). Nonetheless, by RT-PCR analysis using primer sets that can differentiate RIZ1 from RIZ2, it was confirmed that RIZ1 was indeed expressed in various target tissues of female sex steroid hormones (FIG. 1D).

Partial Hormone Resistance in Target Organs of RIZ1 Deficient Female Mice

Figure 2:
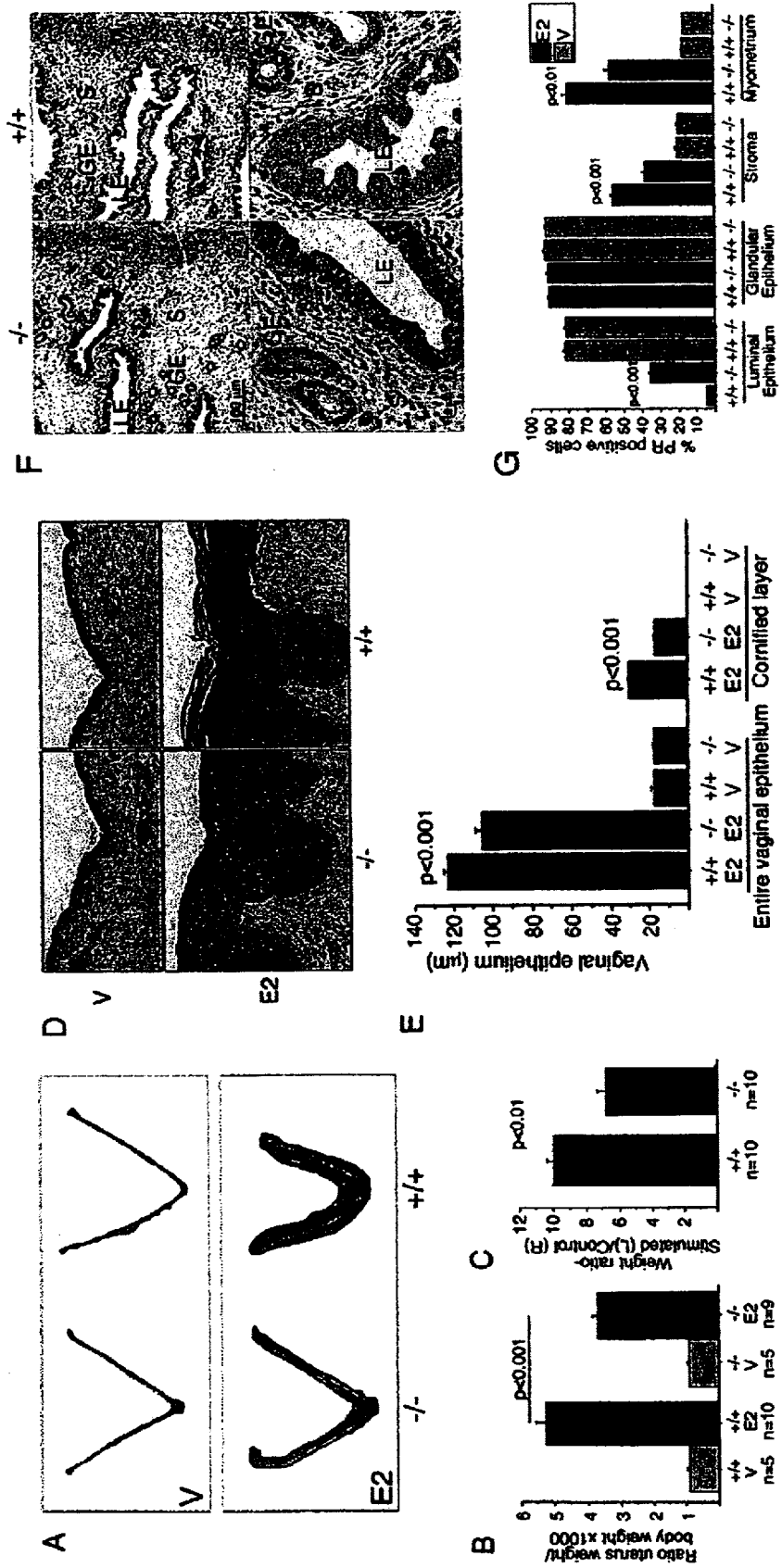
FIG. 2 shows uterine and vaginal responses to female sex steroid hormones in RIZ1 mutant mice. A and B. Uterine wet weight was measured and the ratio of uterine weight to body weight calculated for the indicated number of mice and presented as mean±SEM. C. The uterine response to a decidual response was measured. After treatment with E2 and progesterone, and mechanical stimulation of the left uterine horn, the ratio of the weights of the stimulated (L) to the unstimulated (control; R) horn was calculated for the indicated number of mice and presented as mean±SEM. D and E. Vaginal responses. Vaginal tissues were collected and fixed for H & E staining. The thickness of the entire vaginal epithelium and the cornified layer were measured at 7 randomly selected areas at the maximum depth of the vaginal epithelium in each mouse and data are presented as mean±SEM for 7 mice in each group. F and G. Impaired regulation of uterine progesterone receptor expression by E2 in RIZ1 mutant mice. Uteri were collected and immunohistochemically analyzed for progesterone receptor expression. Estrogen treated uteri are shown in G (top panel: low magnification; bottom panel: high magnification). Randomly selected areas were photographed and more than 1000 cells from each compartment of the uteri of 4 mice in each group were counted, and data is presented as mean±SEM (G). Inserted scale bars apply for both genotypes.

The RIZ1 mutant mice are deficient in RIZ1, but not RIZ2, and therefore lack specifically any PR-domain related functions of the gene (Steele-Perkins et al., Genes Dev. 15:2250–2262 (2001)). These animals are viable and fertile and show no gross developmental defects (Steele-Perkins et al., supra (2001)). To determine the physiological role of RIZ1 in steroid hormone action, uterine growth in response to E2 was first examined in ovariectomized (OVXed) mice (Lubahn et al., Proc. Natl. Acad. Sci. USA 90:11162–11166 (1993)). Wild-type or heterozygous RIZ1 mutant mice responded to E2 treatment with a 5.3±0.5 and 5.4±0.4 fold increase in uterine wet weight. Uteri of homozygous RIZ1 mutants showed a smaller increase of about 3.7±0.4 fold (P<0.001 for +/+ vs. -/-; FIG. 2A and B). Uterine response to mechanical traumatization (decidual stimulation) is mainly a progesterone receptor-dependent process (Lydon et al., Genes Dev. 9:2266–2278 (1995)). OVXed mice were treated with a high dose of progesterone and a low dose of E2, followed by mechanical stimulation of the left uterine horn of each animal. The unstimulated left uterine horn served as a control. The decidual response resulted in an increase in the uterine horn size and was consistently observed in the stimulated left uterine horn in wild-type mice. Only a partial response was observed in the uterine horn of the RIZ1 null mutant (FIG. 2C). These results suggest that RIZ1 is required for maximal uterine response to E2 and progesterone in vivo.

Vaginal cornification in response to a three-day treatment of E2 was examined in OVXed mice. The hormone produces an increased vaginal thickening and cornification of the epithelium (Lubahn et al., supra (1993)), which was consistently seen in the wild-type mice (FIG. 2D,E). RIZ1 null female mice, however, failed to show a maximal such response, thus suggesting that RIZ1 is required for vaginal response to E2 in vivo.

The epithelial and stromal compartments of the uterus were then analyzed for E2-induced changes in progesterone receptor expression. Such a regulation via ER is highly compartment-specific and mimics the changes in the uterus during the estrous cycle (Tibbetts et al., Biol. Reprod. 59:1143–1152 (1998)). Progesterone receptor staining in OVXed RIZ1+/+ and -/-mice treated with vehicle was apparently similar and showed strong immunoreactivity in almost all cells of both the luminal (LE) and glandular epithelium (GE), whereas only a fraction of stromal and myometrial cells were positive (FIG. 2G, data not shown). As expected, E2 treatment of wild type animals had dual effect on progesterone receptor expression, reducing the levels in the LE and increasing the levels in the stromal and myometrial compartments. Immunoreactivity in the GE was unchanged, consistent with previous findings showing that E2 alone does not regulate progesterone receptor expression in this compartment (FIG. 2F,G) (Tibbetts et al., supra (1998)). Upon E2 treatment of RIZ1 deficient animals, the decrease of progesterone receptor levels in the LE was nearly 8-fold less than in wild type tissues, and the increase of the receptor level in the stroma and myometrium was nearly 2-fold less than normal. These findings suggest that RIZ1 plays a role in the E2 regulation of progesterone receptor expression in the uterus.

Figure 3:
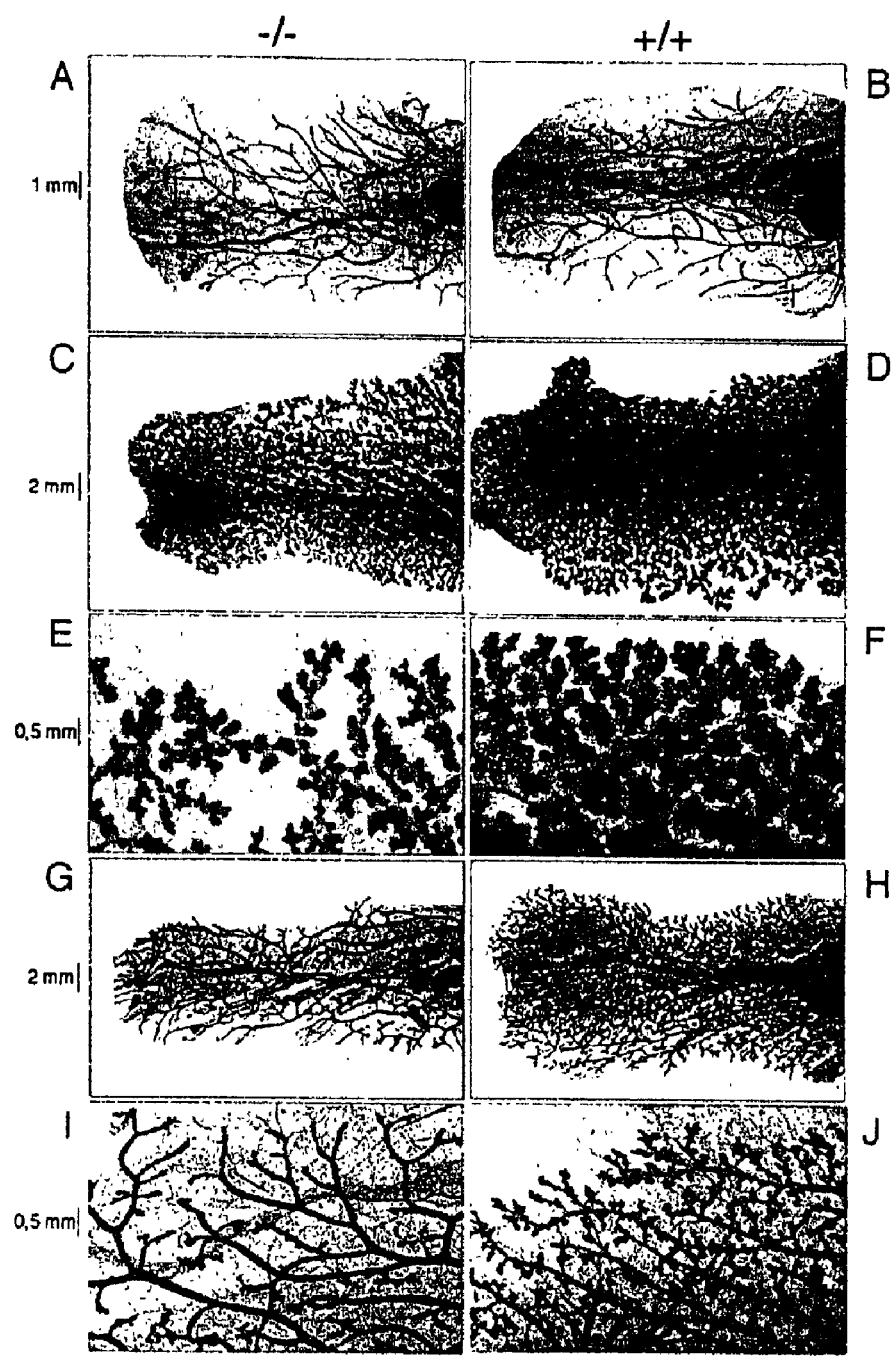
FIG. 3 shows mammopoiesis in RIZ1 deficient mice. Whole mounts of the fourth mammary gland of mice with the indicated genotypes were prepared and stained. A and B, Seven week old virgin mice. C and D, Mice pregnant for the first time. E and F, Higher magnification of the ducts and alveolar structures of the mammary glands of the pregnant mice. G and H, Mammary glands from mice treated with hormone pellets containing P and E2 as described in methods. I and J, Higher magnification of the mammary ducts and alveolar structures from G and H, respectively. Scale bars that apply to both genotypes are inserted.

Steroid hormones play an important role in mammopoiesis (Hennighausen and Robinson, Genes Dev. 12:449–455 (1998)). Both E2 and progesterone are essential for alveolar development during pregnancy. In 7-week-old wild-type females, mammary ducts had started to grow into the mammary fat pad but with no apparent differences in the age-matched RIZ1 null mutants (FIG. 3A and B). However, when stimulated by pregnancy, alveolar structures in wild-type mammary glands were highly developed and appeared on all ductal sections, filling the interductal spaces. In the RIZ1 mutant mammary glands, alveoli were much less developed in terms of number and size of alveoli, and fewer alveoli were observed at the ends of ducts at the same stage of pregnancy (FIG. 3C through F). Although mammary glands of RIZ1 null mutants can still produce milk, these results suggest that RIZ1 is required for normal mammary ductal elongation and alveolar development in vivo during pregnancy. Mammary gland development in response to E2 and progesterone treatment in OVXed adult mice was also examined. E2 and progesterone stimulated a complex ductal arborization and extensive alveolar formation in mammary glands of wild-type mice, which mimics a stage of mammopoiesis in early pregnancy. In the mammary glands of RIZ1 mutant mice, only partial ductal growth was observed after hormone treatment (FIG. 3G through J). Thus, RIZ1 seems to be required for efficient proliferation and differentiation of the mammary gland in response to E2 and progesterone.

Normal Steroid Hormone Response in RIZ1 Deficient Male Mice

Although RIZ1 is expressed in target tissues of male steroid hormones such as testis (Buyse et al., Proc. Natl. Acad. Sci. USA 92:4467–4471 (1995)), it does not appear to serve as coactivator for androgen receptor (FIG. 1A). To study this further, prostate growth was measured in orchiectomized male mice after they were treated with androgen. Similar to female mice, no difference in total body weight was noted in RIZ1 null mutant male animals (Table 1).

TABLE 1

| | Mean ± S.D. (number of mice weighed) | | |
|---|---|---|---|
| | 5 weeks | 8 weeks female | 12 weeks female |
| RIZ1−/− | Female-<br>16.83 + 1.64(11) 83<br>Male-<br>19.24 + 2.25(7) | 21.28 + 2.70(32) | 24.27 + 2.21(13) |
| RIZ1+/− | Female-<br>16.83 + 2.01(15)<br>Male-<br>20.00 + 2.56(15) | 20.49 + 2.70(12) | 24.51 + 3.22(23) |
| RIZ1+/+ | Female-<br>18.52 + 1.55(5)<br>Male-<br>20.61 + 2.72(7) | 20.37 + 2.13(31) | 21.71 + 3.49(13) |

Eight days after orchiectomization, prostates in both wild-type and mutant animals regressed. Injection of testosterone for 7 days stimulated prostate growth in wild-type animals as well as in RIZ1 null animals. Wild-type and RIZ1 null mutant animals had similar ratios of the weight of prostate and urethra to body weight (1.19±0.03 vs. 1.14±0.03; n=10 and 9 mice for +/+ and −/−, respectively; p=0.23). They also had similar ratios of testis weight to body weight (7.7±0.4 vs. 7.4±0.4; n=14 for both genotypes; p=0.58). Thus, tissue responses to testosterone are not significantly affected in mice lacking RIZ1, consistent with the lack of effect of the gene on androgen receptor transactivation functions (FIG. 1A).

Reduced Litter Size by RIZ1 Deficient Female Mice

The reproductive abilities of RIZ1 mutant mice were assessed. Female RIZ1−/−mice were bred with male RIZ1+/−mice and as controls, female RIZ1+/−mice were bred with male RIZ1−/−mice. Also, breedings between heterozygous mutants were conducted. The average litter size from breeding RIZ−/−female×RIZ1+/−male was 6.6±3.2 (S.D.; n=35 litters) but the average litter size was 8.4±2.0 (n=20 litters) for litters of breeding RIZ1+/−female× RIZ1−/−male (P<0.01), and 8.0±2.2 (n=50 litters) for litters of breeding between heterozygous mice (P<0.02). The results indicated a slightly compromised reproductive ability associated with the female, but not male, mice deficient in RIZ1, consistent with the above results showing defective tissue responses to steroids in female but not male animals.

Regulation of ER-dependent Transcription in Breast Cancer by RIZ1 and RIZ2

The above results suggest a physiological role of RIZ1 in E2 response of normal tissues. In view of RIZ1's tumor suppressor role, the question was posed whether RIZ also plays a role in the E2-response of breast cancer cells. RIZ1 is often lost but RIZ2 is uniformly present in breast cancer (He et al., Cancer Res. 58:4238–4244 (1998); Jiang and Huang, Histol. Histopathol. 15:109–117 (2000)). RIZ2 does not serve as a coactivator of ER and can actually neutralize the coactivator function of RIZ1 (Steele-Perkins et al., Genes Dev. 15:2250–2262 (2001)). Therefore, the effects of overexpressing RIZ1 and RIZ2 in MCF-7 were examined in breast cancer cells that express ER and RIZ1 (He et al., supra (1998)). When cotransfected with the ERE-tk-CAT reporter into MCF-7 cells, RIZ1 enhanced estrogen-induced reporter activity (FIG. 4A). In contrast, E2 induced reporter gene transcription was suppressed by RIZ2 expression. In CV-1 cells that lack ER, reporter gene expression was not affected by RIZ1, RIZ2, and E2 (FIG. 4B). The data suggest that RIZ1 can sensitize breast cancer to E2 and that decreasing RIZ1 activity, as achieved by RIZ2 expression, can inhibit E2 sensitivity of breast cancer.

RIZ1 Gene Silencing in Hormone Resistant Breast Cancer

If RIZ1 appears to facilitate E2-mediated normal and breast cancer growth as indicated by the above studies, why is it also a tumor suppressor and often silenced in breast cancer (He et al., supra (1998))? Upon re-analysis of the published data, it was found that RIZ1 loss is related to hormone resistance (as represented by ER status) among those breast cancer cell lines examined (Table 2).

A methylation-specific PCR assay was developed to examine RIZ1 promoter methylation, which showed that DNA methylation is a good indicator of lost or decreased RIZ1 mRNA expression in tumor cell lines and tissues (Du et al., Cancer Res. 22:8094–8099 (2001)). Methylation of RIZ1 promoter was found to be common in breast cancer tissues, occurring in 11 of 25 breast cancer tissues examined. Except for BT20 and ZR75–1 cell lines, the mRNA expression data in Table 2 are from (He et al., supra (1998)). Expression levels below 10% of normal were scored negative (−)

TABLE 2

| | RIZ1 Methylation | mRNA | ER |
|---|---|---|---|
| MB468 | + | − | − |
| MCF-7 | − | + | + |
| MB-435 | + | − | − |
| T47-D | − | + | + |
| MB231 | + | − | − |
| BT474 | − | + | + |
| SKBR3 | + | − | − |
| BT549 | − | + | − |
| BT20 | − | + | − |

To address the relationship between RIZ1 and hormone responsiveness of breast cancer tissues, the ER expression status was examined for 18 of the 25 samples for which tissue sections were available. ER expression was determined by immunohistochemistry (below 10% positivity was considered negative) and was scored in a double-blind fashion without knowledge of the methylation status of these samples. The results showed the same trend as previously found in cell lines that ER negative tumors tend to be RIZ1 negative (Table 3).

TABLE 3

| Ex-pres-sion | ER(−) | | ER(+) | |
|---|---|---|---|---|
| | RIZ1(−) | RIZ1(+) | RIZ1(−) | RIZ1(+) |
| # tumor cases | 83% (5/6) | 17% (1/6) | 42% (5/12) | 58% (7/12) |
| # cell lines | 67% (4/6) | 20% (2/6) | 0% | 100% (4/4) |
| # Total | 75% (9/12) | 25% (3/12) | 31% (5/16) | 69% (11/16) |

Thus, 5 of 6 ER-negative cases were RIZ1 negative compared to 5 of 12 ER-positive cases. Together with data from cell lines, these results shows that there is a significant association between RIZ1 silencing and ER-negative breast cancers (RIZ1 silencing found in 9 of 12 ER-negative samples versus 5 of 16 ER-positive samples, P<0.05). The results also reveal that nearly half of ER-positive cancer tissues were RIZ1 negative (5 of 12), indicating a potential role of RIZ1 silencing in the development of hormone resistance of ER-positive breast cancers. Together, these studies indicate a dual status of RIZ1 in breast cancer that is linked with the presence or absence of ER, and in turn, the early or late stage of the disease. The dual status of the gene appears consistent with its dual role as a tumor suppressor and an ER/E2-dependent tumor promoter (see discussion below).

Histone Methyltransferase Activity of RIZ1 and Regulation by Estrogen

The results of animal knock out studies presented here and previously (Steele-Perkins et al., supra (2001)), as well as the dual role of RIZ1 in breast cancer discussed above, suggest a physiological role of RIZ1 as an ER-coactivator/growth promoter and a tumor suppressor. Because it is only the PR domain of RIZ1 that is missing in these animals or in tumors, owing to normal expression of RIZ2, it was asked whether RIZ1 has an activity that may explain its dual function as an ER-coactivator/growth promoter and tumor suppressor.

Recombinant GST fusion proteins of RIZ1's N-terminus PR domain region were prepared in bacteria. The recombinant proteins were purified and assayed for histone methyltransferase activity using histones as substrates and S-adenosyl-[methyl-$^3$H]-L-methionine as methyl group donor. Reaction products were separated by SDS-PAGE and visualized by flurography. Specific labeling of histone H4 was observed in the presence of purified GST product consisting of residues 1–200 of RIZ1 (FIG. 5A). GST alone or a protein consisting of residues 1–161 lacked HMT activity. Furthermore, missense mutations found in tumors, C106Y, I188V, and A159V, abolished HMT activity. The results suggest that RIZ1 has HMT activity, which requires the conserved PR-domain (residues 30–160) as well as the non-conserved residues C-terminal to the PR-domain (residues 162–200).

It was next asked whether the HMT activity of the PR domain may be modulated by additional sequences of RIZ1 by testing longer RIZ1 N-terminal fragments made in bacteria. A GST fusion protein expressing the N-terminal 332-residue peptide showed similar activities to the N-terminal 200-residue peptide in methylating H4 (FIG. 5B). An attempt to test an even longer peptide (520 residue) in bacteria was not successful because of low yield of protein. The result suggests that residues 200–332 may not intrinsically contribute to HMT activity but could not exclude other regions of RIZ1 (333–1719) from playing role in modulating the HMT activity of the N-terminal 200-residue region.

A domain located at the C-terminus of RIZ1 protein (amino acids 1514–1680) was previously defined that can bind to the PR domain of RIZ1 (Huang et al., *J. Biol. Chem.* 273:15933–15940 (1998)). It was next asked whether this domain, termed PBD or PR-binding domain, can regulate the PR HMT activity. The previously described GST fusion protein, GST-hRIZ1(1514–1680) or now termed GSTRIZPBD, was examined for its effects on the HMT activity of GSTRIZ332. Unexpectedly, GSTRIZPBD protein alone showed HMT activity, specifically on H4, suggesting that the RIZ PBD domain represents a novel catalytic motif of methyltransferase. A synergistic enhancement (more than additive effects) of HMT activity was observed when GSTRIZ322 and GSTRIZPBD were both present in HMT reactions, as indicated by the increased methylation of H4 and the methylation of a new substrate with a molecular weight similar to that of H1 (FIG. 5C). This result suggests that the PR domain HMT activity can be modulated by other regions of RIZ1, such as the PBD domain.

Figure 6:
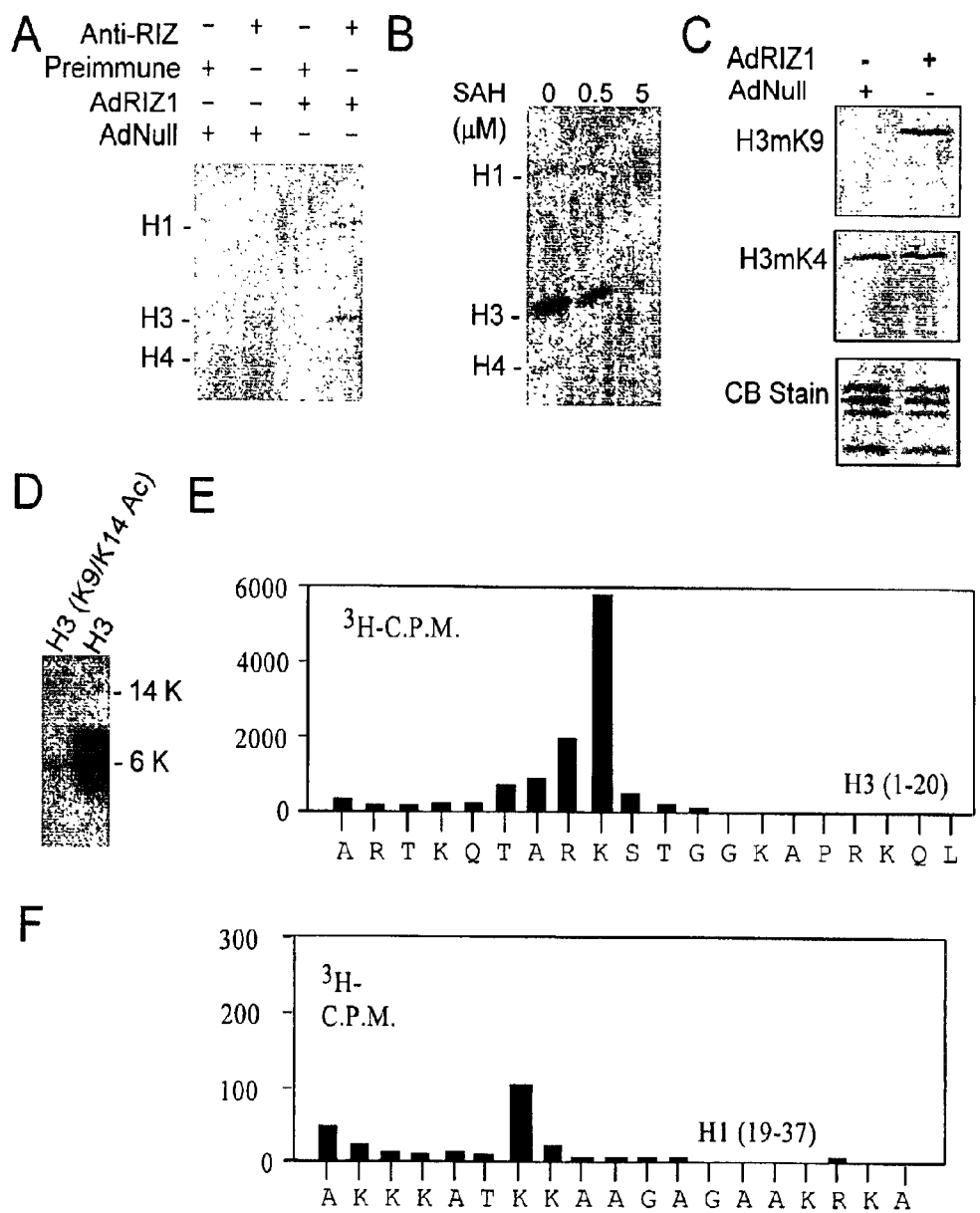
FIG. 6 shows methylation of histones by full length RIZ1 protein expressed in mammalian cells. A. Nuclear extracts (500 μg) prepared from U20S cells infected with AdRIZ1 virus or AdNull control virus were immunoprecipitated with preimmune serum or RIZ1 serum anti-KG7.1S. Immunoprecipitates were then assayed for HMT activity using free histones as substrates. The panel shows fluorography indicating methylation of histone H1, H3 and H4. B. Enhanced methylation of lysine 9 on H3 by RIZ1 overexpression. Histones were extracted from U20S cells infected with AdRIZ1 or control virus and analyzed by western blot analysis using either antibody for methylated K9 on H3 or methylated K4 on H3. C. Methylation of H3 N terminus peptide in vitro by RIZ1. In vitro methylation assays using immunoprecipitated RIZ1 as enzyme and the indicated N-terminal 1–20 residue peptide of H3 and acetylated H3 (K9/K14 Ac: acetylated on K9 and K14 residues) as substrates. The methylated peptides were resolved by 16% Tris-Tricine SDS gel followed by fluorography. D. Automated sequencing of the H3 N-terminal peptide (residues 1–20) that had been methylated in vitro by full length RIZ1 purified by immunoprecipitation. The tritium incorporation of individual amino acids identified at each successive round of microsequencing is shown.

Enzyme activity of full-length RIZ1 protein from mammalian cells was next assayed. Human osteosarcoma U2OS cells, which express little RIZ1 (He et al., *Cancer Res.* 58:4238–4244 (1998)), were infected with AdRIZ1 virus or control AdNull virus and nuclear extracts from virus infected cells were immunoprecipitated with RIZ serum anti-KG7.1S or preimmune serum. Immunoprecipitated products by RIZ1 serum from RIZ1-expressing extracts caused methylation of H1, H3, and H4 (FIG. 6A). A similar result was also obtained using a different RIZ1 antiserum, 1715 (data not shown). As controls, HMT activity was not detected for immunoprecipitates of preimmune serum or when RIZ1 negative nuclear extracts were used for immunoprecipitation.

Figure 5:
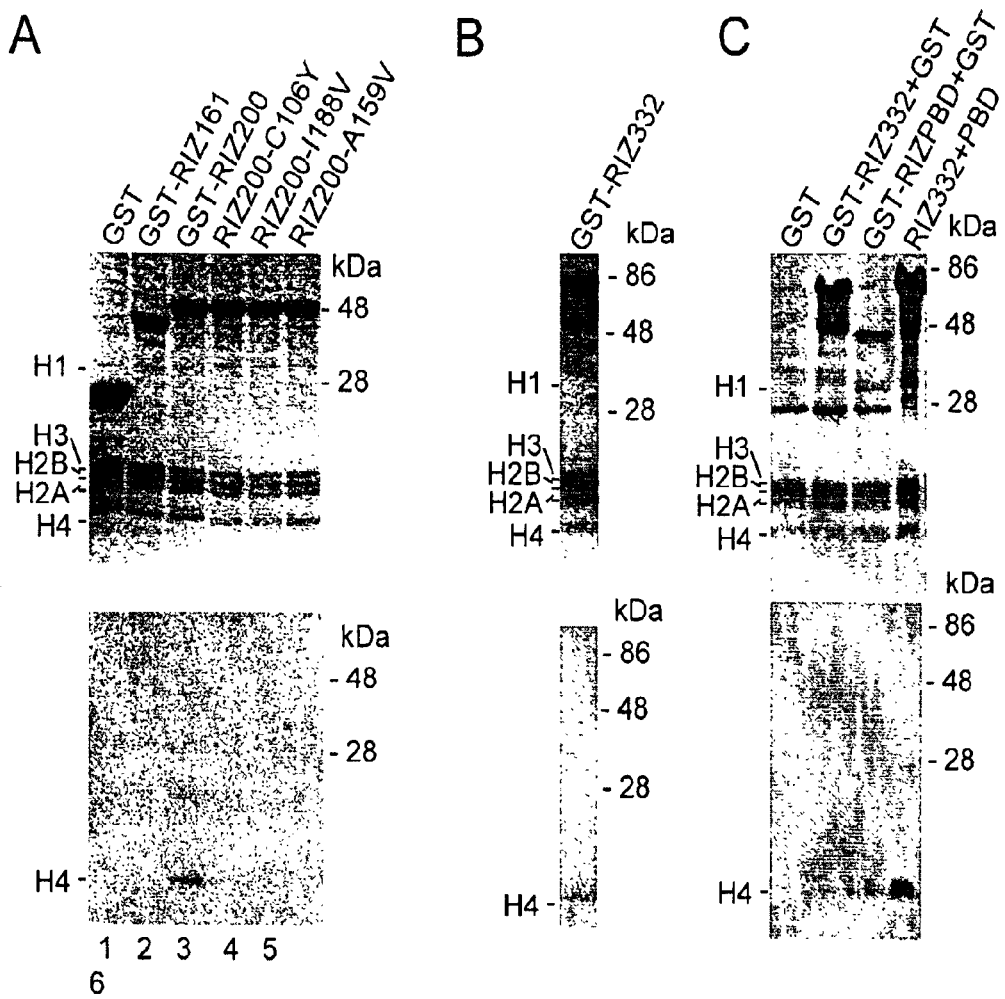
FIG. 5 shows methylation of histones in vitro by the PR-domain, the PR-binding domain (PBD), and the combined action of the two domains. Bacteria-expressed GST fusion proteins of human RIZ1 were used for in vitro HMT reactions using histones as substrates. Top panel shows Coomassie blue staining of purified proteins and histones. Bottom panel shows fluorography indicating methylation of substrates. A. Methylation of H4 by GST-RIZ200 (consisting of RIZ1 residues 1–200) but not by GST protein alone, GST-RIZ161 (consisting of RIZ1 residues 1–161), and three GST-RIZ200 point mutant proteins as indicated. B. Methylation of H4 by GST-RIZ332 (consisting of RIZ1 residues 1–332). C. Enhanced methylation conferred by GST-RIZ322 plus GST-RIZPBD.

The data indicate that RIZ1 protein of mammalian cells has HMT activity, which is consistent with the activity of truncated proteins obtained from bacteria (FIG. 5). However, full length protein appears to target more histone substrates than truncated proteins from bacteria, probably because it has sequences or modifications or both that are missing in bacteria expressed proteins. The results are consistent with other regions of RIZ protein regulating PR domain HMT activity.

In view of RIZ1's role in tumor suppression, it was determined whether S-adenosylhomocysteine (SAH), an analog inhibitor of SAM-dependent methyltransferases whose abnormal accumulation is linked with carcinogenesis, can inhibit RIZ1 enzyme activities. The effect of SAH on the in vitro methylation of histones by immunoprecipitated RIZ1 was tested. A methylation assay was performed in the presence of 0, 0.5 and 5 $\mu$M of SAH and 0.42 $\mu$M of 3H-SAM. Histone methylation by RIZ1 was partially inhibited by 0.5 $\mu$M of SAH and completely inhibited by 5 $\mu$M of SAH (FIG. 6B). The results show that SAH is an inhibitor of RIZ1 methyltransferase.

The methylated lysine residues at position 4 and 9 of histone H3 are the best-characterized histone lysine methylations with regard to their biological function. Methylation of H3-K9 is associated with gene repression and heterochromatin formation, whereas methylation of H3-K4 is often linked to gene activation (Noma et al., *Science* 293:1150–1155 (2001); Rea et al., *Nature* 406:593–599 (2000); Strahl et al., *Curr. Biol.* 11:1–5 (2001)). Each of the two lysine residues can be targeted by several different SET domain HMTs, which are either K4 or K9 specific but not both, and often have non-H3 substrates such as H1 (Nishioka et al., *Genes & Dev.* 16:479–489 (2002); Rea et al., *Nature* 406:593–599 (2000); Tachibana et al., *J. Biol. Chem.* 276:25309–25317 (2001); Wang et al., *Mol. Cell.* 8:1207–1217 (2001a)). To determine whether RIZ1 may belong to such a group of H3-K4 or H3-K9 specific HMTs may immediately explain how RIZ1 functions in transcription. Therefore, it was determined whether RIZ1 may have any activity toward H3-K4 or H3-K9. First, it was determined whether RIZ1 can alter the methylation of these residues in vivo in mammalian cells. Histones were extracted from U2OS cells infected with AdRIZ1 or control virus and analyzed by western blot analysis using antibodies that recognize specifically H3-K9 methylation or H3-K4 methylation. The result shows that RIZ1 increased H3-K9 methylation but did not affect H3-K4 methylation (FIG. 6C), consistent with H3-K9 but not H3-K4 as a potential target of RIZ1 methyltransferase.

To show that RIZ1 can directly methylate H3-K9, peptide methylation and sequencing experiments were performed. A peptide consisting the N-terminal 1–20 residues of H3 was indeed methylated in vitro by immunoprecipitated RIZ1 protein using S-adenosyl-[methyl-3H]-L-methionine as methyl donor (FIG. 6D). In contrast, a peptide containing acetylated K9 and K14 was not methylated, consistent with K9 but not K4 as a target of RIZ1. The migration of the peptide as a doublet has also been observed by others, and may be due to the poor resolution of SDS-PAGE. The methylated peptide was next purified by HPLC and subjected to peptide sequencing analysis. Purified peptides were sequenced from the amino termini and the radioactivity of each of the sequenced residues was determined by scintillation counting. A single radioactive peak at lysine 9 was observed (FIG. 6E). The results suggest that H3-K9, but not H3-K4, is a target of RIZ1 methyltransferase.

Next, the possible methylation site on H1 was determined. A H1 peptide (aa 15–37) was methylated by RIZ1 in vitro, which was then subjected to HPLC purification and sequencing analysis. Repeated methylation and sequencing analysis showed that lysine 25 was methylated by RIZ1 (FIG. 6F).

Figure 7:
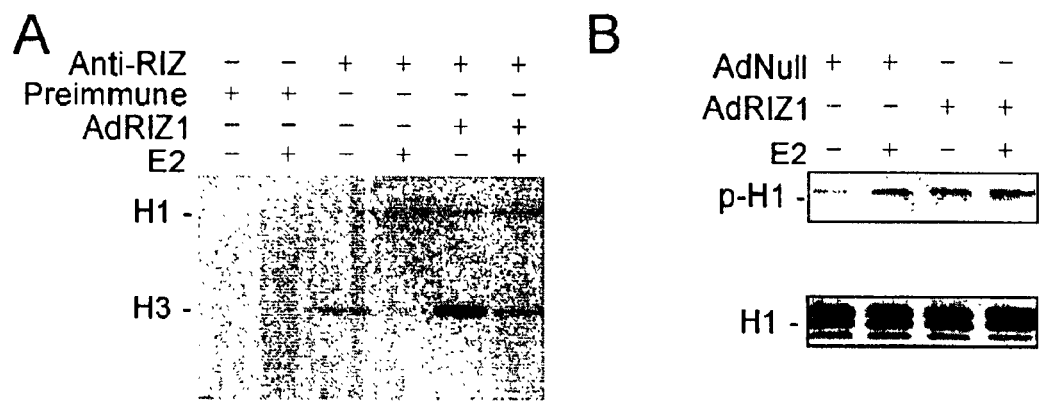
FIG. 7 shows regulation of RIZ1 methyltransferase activity by estrogen. A. Effects of estrogen on RIZ1 in MCF7 cells. Same amounts of nuclear extracts (500 μg) from E2 treated or control MCF-7 cells, or from AdRIZ1 infected cells were immunoprecipitated with preimmune serum or RIZ1 serum anti-KG7.1S. Immunoprecipitates were then assayed for HMT activity using free histones as substrates. The panel shows fluorography indicating methylation of histone H1 and H3. B. Effects of E2 and RIZ1 on H1 phosphorylation. MCF7 cells infected with control or AdRIZ1 virus were treated with E2 or vehicle for 48 hr. Histones were extracted after treatment and analyzed by western blot using anti-phosph-H1 (top panel) or anti-H1 antibodies (bottom panel).

The capacity to methylate H3 in a K9 specific manner suggests a role for RIZ1 in transcriptional repression, which appears to be in conflict with RIZ1's role as an ER coactivator. To help understand this apparent paradox, the estrogen effects on RIZ1 HMT activity were examined. Nuclear extracts from control and E2 treated MCF-7 cells were immunoprecipitated by RIZ1 serum anti-KG7.1S or preimmune serum. As expected, HMT activity (labeling of H3 and H1) was detected in the immunoprecipitates of RIZ1 serum but not preimmune serum (FIG. 7A, lanes 1 and 3). Interestingly, estrogen treatment decreased H3 methylation but maintained or slightly enhanced H1 methylation by RIZ1 (FIG. 7A, lane 4). RNase protection analysis did not reveal altered RIZ1 or RIZ2 gene expression by E2 treatment of MCF-7 cells (not shown). Furthermore, E2 also similarly regulated the HMT activity of overexpressed RIZ1 protein in AdRIZ1 virus infected MCF-7 cells (FIG. 7A, lanes 5–6); cells infected with control virus showed similar results as non-infected cells (not shown). Thus, E2 appears to regulate RIZ1 HMT activity in a selective way, inhibiting specifically methylation of H3 but not H1. The data suggest that E2 may turn RIZ1, possibly with a dual role of transcriptional repressor and activator, into a transcriptional activator by selectively turn off its repressor activity as represented by H3 methylation while enhancing its putative activator activity, presumably represented by H1 methylation.

Although the function of H1 methylation remains to be characterized, the results here suggest, at least, that RIZ1 methylation of H1 is unlikely to be similar to H3-K9 methylation, in view of the contrasting behavior of these two methylation activities of RIZ1. Because H1 phosphorylation has been linked with transcriptional activation (Bhattacharjee et al., Mol. Cell. Biol. 21:5417–5425 (2001); Dou and Gorovsky, Mol. Cell. 6:225–231 (2000)), it was next asked whether E2 or RIZ1 can enhance H1 phosphorylation. Histones were extracted from MCF7 cells infected with AdRIZ1 or control virus and analyzed by western blot analysis using antibodies that recognize specifically phosphorylated H1. The result shows that both E2 and RIZ1 increased H1 phosphorylation (FIG. 7B), suggesting that E2 or RIZ1 may function to stimulate transcription in part by mediating enhanced H1 phosphorylation. That RIZ1 methylation of H1 was positively correlated with H1-phosphorylation suggests that such methylation is correlated with transcriptional activation.

Next, the methyl acceptor potential of phosphorylated H1 with non- or hypophosphorylated H1 was compared. Histones were isolated from cells arrested at G2/M by nocodazole, which were enriched for phosphorylated H1, and used as substrates for in vitro methylation by RIZ1. H1 from nocodazole treated cells appeared to serve as a poor substrates compared to H1 from control cells (not shown). This result indicates either that H1 isolated from nocodazole treated cells was both phosphorylated and methylated or that phosphorylation of H1 may prevent its methylation. To resolve this, histones were treated with phosphatase prior to use as methylation substrates. Phosphatase treatment removed a significant amount of phosphate on H1 but did not affect its ability to serve as methylation substrates (not shown). Together, these results suggest that phosphorylated H1 is associated with a higher extent of methylation than non- or hypophosphorylated H1 and that methylated H1 is associated with a higher degree of phosphorylation than non- or hypomethylated H1.

The time course response of RIZ1 methylation activity to E2 treatment was then studied. A decrease of RIZ1 H3 methylation activity was found at 4 hr post E2 treatment, which stayed at low levels thereafter (not shown). Because E2-induced cell proliferation is not known to occur prior to at least 8 hr of treatment, the data suggest that inhibition of RIZ1 H3-methylation activity by E2 is unlikely a result of cell proliferation.

The observation that E2, a growth factor, has a sustained inhibitory effect on RIZ1 methylation of H3 but not H1 suggests that H3 and H1 methylation activity of RIZ1 may be oppositely linked with cell growth. To further study the contrasting behavior of H1 and H3 methylation, regulation of RIZ1 HMT activity by cell growth was examined, using 12-O-tetradecanoyl-phorbol-13-acetate (TPA) treatment of U937 myeloid leukemic cells as a model system. U937 cells undergo growth arrest and terminal differentiation into monocytes when exposed to TPA. This cell model was selected for study because it has been shown in these cells that RIZ gene expression is only marginally regulated by TPA. A slight increase (less than 2 fold) in RIZ1 mRNA, but no change in RIZ2 levels, was not observed until after 3 or more days of TPA treatment (Gazzerro et al., Mol. Med. 7:552–560 (2001)). Thus, any significant changes in HMT activity, especially a decrease, may not be attributed to changes in RIZ1 protein amounts, at least within the first three days of treatment. The TPA effects on U937 cell growth and differentiation were confirmed by counting cell numbers and examining cell morphology (not shown). It was also confirmed that RIZ gene expression was not significantly altered within the first 3 days of TPA treatment. By assaying the HMT activity of RIZ1 immunoprecipitates from nuclear extracts, it was found that H3 methylation was increased, whereas H1 methylation was slightly decreased at 24 hr following TPA treatment (not shown). Similar results were observed at 3 days or 7 day spost TPA treatment, although H3 methylation activity was noted to be lower than that at 1 day post treatment. No significant change in HMT activity was noted for any treatment periods of less than 24 hr. The change at 24 hr post TPA treatment was well before any significant growth arrest had taken place, suggesting that such a change is unlikely a result of growth arrest. The results suggest that the H3 methylation activity of RIZ1 is linked with growth arrest, whereas its H1 methylation activity is associated with cell proliferation, confirming the above described contrasting behavior of these activities in response to E2.

Discussion

The above results show that female mice deficient in RIZ1 display an impaired response to E2 and progesterone, and reduced reproductive abilities. RIZ1 shows coactivator activity for ER and progesterone receptor but no or weak activity for other NHRs examined. Furthermore, the results suggest that a coactivator (RIZ1) may serve as both an E2-dependent growth promoter in early stage breast cancer and a tumor suppressor in preventing breast cancer progression to an estrogen independent state. Estrogen mediated transactivation in breast cancer cells is suppressed by a RIZ1 antagonist (RIZ2), and hormone resistant breast cancers more commonly carry a silenced RIZ1 gene than hormone sensitive breast cancers. These data suggest that RIZ1 has HMT activity, which is mediated-by two independent but interacting catalytic motifs. The HMT activity of the PR domain is linked to both its ER-coactivator function and tumor suppressor function. Cancer-associated mutations in the PR-domain, which inactivate its coactivator function, impair the HMT activity. Also, the HMT activity of RIZ1 can be regulated by E2, in a fashion consistent with RIZ1's role as an ER-coactivator.

The specificity of RIZ1 in its interaction with female sex NHRs contrasts to members of the SRC-1/p160 family members, which seem more promiscuous in this respect. Thus, one may expect more subtle phenotypes for RIZ1 deficient mice versus SRC-deficient animals. Indeed, this is the case even when comparing to mice deficient in SRC-1, which shows the mildest phenotypes among animals deficient in a SRC member (Wang et al., *Proc. Natl. Acad. Sci. USA* 97:13549–13554 (2000); Xu et al., *Proc. Natl. Acad. Sci. USA* 97:6379–6384 (2000); Xu et al., *Science* 279:1922–1925 (1998)). While SRC-1 and RIZ1 deficient female animals show similar reduced sensitivity to female sex hormones, SRC-1 mutation, unlike RIZ1, also affects mammary duct growth during puberty in virgin mice and hormone response in males. The partial hormone resistance phenotypes observed in RIZ1 or SRC-1 deficient mice likely reflect overlapping functions of RIZ1 or SRC-1 related proteins, for which there are many. Or, it may be related to an additive effect of RIZ1 and SRC-1 on ER function. Reduced H3-K9 methylation, as induced by E2 inhibition of RIZ1, would, in and of itself, facilitate transcription activation by reducing the binding of the heterochromatin protein HP1 to methylated K9 on H3 (Bannister et al., *Nature* 410:120–124 (2001); Lachner et al., *Nature* 410:116–120 (2001)). In addition, transcription would be further enhanced by the acetylation of the methyl-free H3-K9 by SRC-1 or its related HATs.

The partial reduction in tissue response to steroids in RIZ1 deficient mice was accompanied by a corresponding reduction in-target gene expression. E2 induction of progesterone receptor gene expression in the stroma and myometrium compartments of the uterus was reduced in RIZ1 deficient mice (FIG. 2F–G). The result suggests a physiological role of RIZ1 in facilitating ER-transcriptional activation function and that such a coactivator function is likely responsible for the observed tissue response to E2.

While the overall tissue response to steroids is only partially reduced by RIZ1 deficiency, this does not necessarily indicate that RIZ1 is unable to serve a unique and non-redundant function in facilitating NHR function. It is possible that at the molecular level, RIZ1 may be uniquely involved in controlling expression of certain target genes. Indeed, estrogen repressed progesterone receptor gene expression nearly 20-fold in the luminal epithelial cells of the uterus in the presence of RIZ1 but only 2-fold in its absence (FIG. 2F–G). Although ER/E2 appear to largely use RIZ1 as a coactivator, this result further suggests that it can also employ it as a corepressor in certain circumstances. It is possible that ER/E2 may enhance RIZ1 methylation of H3-K9 in certain cellular contexts.

That RIZ1 appears required for E2 induced tissue growth contrasts with its tumor suppressor role. To help understand the apparent paradox, the role of RIZ1 in breast cancer was studied. RIZ1 overexpression enhanced ER-dependent transactivation of reporter gene whereas overexpressing a RIZ1 antagonist, RIZ2, inhibited the transactivation function of endogenous ER in breast cancer cells. Thus, RIZ1 inactivation maybe associated with decreased hormone response in breast cancers. Consistently, RIZ1 silencing was shown to be significantly more common in E2 resistant or ER-negative comparing to ER-positive breast cancers. It is logical to expect that alteration of ER coactivators may play a role in the hormone response phenotypes of breast cancers. This idea has been pursued by several previous studies, which found overexpression of SRC3 (AIB1) and SRA in mostly ER-positive breast cancers (Anzick et al., *Science* 277:965–968 (1997); Kurebayashi et al., *Clin. Cancer Res.* 6:512–518 (2000); Murphy et al., *Cancer Res.* 60:6266–6271 (2000); Thenot et al., *Mol. Cell. Endocrinol.* 156:85–93 (1999)). As might be anticipated, there is a quantitative relationship between ER concentration in breast cancer tissue and response to E2 (Allegra, *Semin. Oncol.* 10:23–28 (1983); Osborne et al., *Cancer* 46:2884–2888 (1980)). The higher the ER amount, the more likely a response. ER is rarely mutated and the term ER-negative refers to ER level that is below an empirically determined level. Partial hormone response still exists in such cells with low ER levels. It is therefore expected that loss in one of the coactivators (RIZ1) may further reduce hormone response of such cells. Similarly, silencing of a coactivator in ER-positive breast cancers, as shown here for RIZ1, may play a role in the acquisition of hormone resistance phenotypes of these tumors.

For hormone sensitive early stage breast cancer, the dual role of RIZ1 as a tumor suppressor and an ER-coactivator/growth promoter raises the issue whether disabling RIZ1 could be beneficial or not to tumor cell proliferation. It appears that retaining RIZ1 may be more favorable than disabling it, in view of the reduction of E2-induced tissue growth in RIZ1 deficient mice. This view is also consistent with the finding that RIZ1 silencing was less common in ER-positive versus ER-negative breast cancers.

If RIZ1 may confer growth advantage to early stage breast cancers, why is it not so for late stage ER-negative breast cancers, where RIZ1 is commonly silenced? This is expected for a tumor suppressor that also has an ER-dependent growth promoter function. In breast cancers with functional ER, which, upon E2-binding, may turn RIZ1 from a default tumor suppressor into a coactivator/tumor promoter, RIZ1 is often present and may play a role in promoting tumor growth in the presence of E2. In these tumors, RIZ1 may also play a role in keeping tumor growth in check when E2 is absent. In contrast, in ER-negative breast cancers, where a coactivator would be no longer useful and a tumor suppressor would be undesirable, RIZ1 is frequently lost, which may play a role in promoting the E2-independent growth phenotype of these tumors.

The questions arises as to why most other ER-coactivators are not silenced in hormone resistant breast cancers (Anzick et al., *Science* 277:965–968 (1997); Kurebayashi et al., *Clin. Cancer Res.* 6:512–518 (2000); Murphy et al., *Cancer Res.* 60:6266–6271 (2000); Thenot et al., *Mol. Cell. Endocrinol.* 156:85–93 (1999)). This is probably because they are not tumor suppressors. It is likely that only a coactivator with tumor suppressor function would represent a preferred target of inactivation during the transition from hormone sensitive to insensitive tumors. During such transition, hormone sensitive tumors will develop mechanisms to grow in the absence of hormonal stimuli or ER function. In these tumor cells that have survived compromised ER, a coactivator may not be useful anymore, and thus there will be no longer a selective pressure to keep it active. Meanwhile, in the absence of the ER switch, the default tumor suppressor function of a coactivator would be on, which would not be favorable to tumors and a selective pressure to inactivate the coactivator may emerge.

These results suggest that RIZ1 possesses intrinsic HMT activity. The RIZ1 specific region (1–200 aa) containing the PR-domain, which is absent in RIZ2, is sufficient for histone H4 methylation in vitro. The PR-domain (residues 30–160) is necessary but insufficient, and requires the less conserved regions (residues 161–200) C-terminal to the PR-domain for HMT activity. The requirement for the region nearby the PR-domain is similar to what has been described for the SET-domain (Rea et al., *Nature* 406:593–599 (2000)). The activity of the PR domain was impaired by tumor associated point mutations, consistent with an important role of the activity in tumor suppression functions.

A new methyltransferase catalytic motif was identified, the PBD domain, located at the RIZ1 C-terminus. This domain can methylate H4 in vitro and can physically/functionally cooperate with the PR domain to produce higher HMT activity as well as to broaden substrate specificity. The PBD domain appears not to be significantly related to any proteins in the database. That this domain has HMT activity and can modulate PR activity is consistent with a potential role of this domain in tumor suppression, as indicated by its deletion owing to frameshift mutations in microsatellite unstable cancers.

These data show that a bacteria-expressed 200-residue peptide consisting of the PR-domain region of RIZ1 N-terminus methylated histone H4 while the full-length protein also used H1 and H3 as substrates. The result is consistent with a need for other regions of RIZ1, such as the PBD domain, in modulating the PR domain activity. Indeed, a novel H1 like-protein was methylated only in the presence of both PR and PBD but not by either alone. Alternatively, immunoprecipitated RIZ1 may not be free of RIZ1 bound proteins that could modulate its enzyme activity. RIZ1 may exist as part of a protein complex and the intact nature of such a complex may be required by HMT activity. An example of a HMT complex is the SUV39H1complex of 650 kDa (Nishioka et al., *Genes & Dev.* 16:479–489 (2002)). Finally, mammalian specific post-translational modifications of RIZ1 could play a role in substrate specific methylation activities. The latter two possibilities are consistent with the substrate specific regulation of RIZ1 HMT activity by E2 and TPA, and should be an important topic for future investigations.

The results also show that lysine 9 of histone H3 is a major methylation target of RIZ1 protein. RIZ1 protein caused enhanced H3-K9 methylation in vivo and also methylated H3-K9 in vitro. H3-K9 methylation is linked with heterochromatin formation and gene silencing, which in turn, implicates a similar role for RIZ1. Histone H1 and H4 are also methylated by RIZ1 but the role of H1 and H4 methylations in gene transcription remains to be understood. A RIZ1 target residue was identified on H1 in vitro as lysine 25, which is consistent with the known methylation of H1-K25 in vivo (Ohe et al., *J. Biochem.* (Tokyo) 100:359–368 (1986)).

That E2 can maintain or enhance methylation of one substrate (H1) while decrease methylation of another (H3) suggests a complex mechanism of regulation of RIZ1 activity. The changes in H3 and H1 presumably together contribute to the ligand-dependent RIZ1 activation of ER trans-activation functions. That H3-K9 methylation by RIZ1 is inhibited by E2 is consistent with RIZ1 as a coactivator, given that such methylation is linked with gene silencing. The contrasting change in H1 methylation suggests that the role of such methylation is likely to be at least different from, if not the opposite of, that of H3-K9 methylation. H1 phosphorylation is known to be important in transcriptional activation (Bhattacharjee et al., *Mol. Cell. Biol.* 21:5417–5425 (2001); Dou and Gorovsky, *Mol. Cell.* 6:225–231 (2000)), although the role of its methylation remains unknown. The finding here that RIZ1 or E2 induced both phosphorylation and methylation of H1 suggests a role for H1 methylation similar to that of H1 phosphorylation. In view of the coactivator function and the previously described transcriptional repressor function (Xie et al., *J. Biol. Chem.* 272:26360–26366 (1997)), RIZ1 appears to have a dual role in both transcription activation and repression. The dual role may be mediated in part by methylation of H3-K9 and H1-K25, respectively (Table 4), which may be turned more toward one direction or the other depending on the protein and promoter environment of RIZ1 at particular circumstances. When RIZ1 is recruited by estrogen to activate transcription, the H3 methylation function of RIZ1 would be inhibited and the H1 methylation would be maintained or enhanced. The results suggest a model that RIZ1 has a dual role of a tumor suppressor and an ER-coactivator/growth promoter and the same PR-domain is required for both. ER/E2 appears to be a switch that can turn RIZ1 from a tumor suppressor into a growth promoter. The dual role of RIZ1 may be mediated by different substrate usage. The H3-K9 methylation/gene repression function of RIZ1 appears to be associated with growth arrest whereas the H1 methylation is associated with cell growth, as indicated by the changes of these methylation activities of RIZ1 during terminal differentiation of U937 cells (summarized in Table 4). The tumor suppressor role of RIZ1 is non-tissue specific but the ER-coactivator function is restricted to ER-positive tissues.

TABLE 4

| | E2 target tissues or ER(+) breast cancer | Non-E2 target tissues or ER(−) breast cancer | Cell proliferation potential | |
|---|---|---|---|---|
| RIZ1 function[a] | +E2 | −E2 | high | low |
| H1-K25 methylation | + + | + | + + | + |
| H1 phosphorylation Gene activation Growth promotion | + | | | |
| H3-K9 methylation Gene repression Growth suppression | + + + | + + | + | + + |

[a]The functional activity of RIZ1 is indicated as relatively low(+) or high(++)

It seems paradoxical that E2 employs a tumor suppressor for its growth promoting functions. That RIZ1 HMT activity is sensitive to E2 raises the possibility that RIZ1 may have a role as a sensor and breaker to prevent abnormal hormone-independent growth of cells. The presence of RIZ1 in early stage breast cancers may explain the lack of tumor growth in the absence of E2, while its common absence in advanced breast cancers may explain the hormone-independent tumor growth. E2 may serve as a switch to turn off the tumor suppressor function of RIZ1, perhaps by changing target genes and/or HMT activities. Given that the HMT function is required for both tumor suppressor and coactivator functions of RIZ1, E2 must not simply turn off all HMT activities. It is therefore reassuring that E2 can selectively inhibit RIZ1 HMT activity toward one substrate (H3) while maintain or enhance the activity toward the other (H1).

In summary, the studies described above demonstrate that a HMT (RIZ1) is a target of estrogen and is required for efficient female sex hormone action in vivo. Compromised HMT function of RIZ1 is associated with estrogen resistant breast cancers, and may prove important in the transition to hormone resistance and hormone independent growth during breast cancer progression. By analogy, altered HMT function may also be involved in clinical syndromes characterized by an impaired female sex hormone homeostasis such as osteoporosis, cardiovascular disease, and Alzheimer's disease.

EXAMPLE II

This example shows various assays suitable for identifying RIZ1 modulatory compounds and compounds that modulate progesterone receptor activity.

A. Biochemical Assay Based on Binding of RIZ1 to Universal Inhibitors of Protein Methyltransferase Activity.

The best presently known universal inhibitor of PMT is S-Adenosyl-L- or D-homocysteine (SAH, Ki=5 to 12 $\mu$M). A less potent inhibitor is Adenosyl-L-ethionine (Ki=170 $\mu$M). SAH mimics the structure of S-adenosyl-L-methionine (SAM) that is the substrate of PMT and the methylgroup donor. RIZ1 is expected to bind to SAH through its PR/PMT motif and its PBD domain.

Multi-well plates are coated with SAH and each well contacted with compounds from a small molecule chemical compound library. The plates are incubated with purified recombinant protein,containing the RIZ1 PR/PMT motif (about 200 amino acids) that has been labeled with a fluorescent probe. After washing away unbound RIZ1 protein, the plates are read by a fluorescence detector.

B. Biochemical Assay Based on Binding of RIZ1 to ER or PR

The coactivator function of RIZ1 on ER and PR is dependent upon physical complex formation. Binding of RIZ1 to ER and PR is mediated by the LXXLL motif of RIZ1 and is hormone dependent.

Recombinant RIZ1 protein is coated onto multiwell plates and each well contacted with compounds from a small molecule chemical compound library, as well as estrogen or progesterone. The plates are incubated with purified recombinant ER or PR protein that is labeled with a fluorescent probe. After washing away unbound ER or PR protein, the plates are read by a fluorescence detector.

C. Cellular Assay Based on RIZ1 Coactivation of ER or PR

Multiwell plates are seeded with CV1 cells and the cells transfected with a plasmid containing a ER responsive promoter linked to a luciferase reporter, a plasmid expressing ER, and a plasmid expressing RIZ1. Each well is contacted with compounds from a small molecule chemical compound library. Two days following transfection, the luciferase activity of each well is assayed and read by a fluorescence detector.

D. Assay to Determine or Verify the In Vivo Efficacy of Modulators of RIZ1

Once target compounds are obtained through in vitro biochemical or cellular high throughput screening, the compounds are tested for in vivo efficacy in inhibiting/enhancing the physiological function of RIZ1. Female mice lacking RIZ1 PR/PMT function show decreased response to estrogen and progesterone. Therefore, inhibitors of RIZ1 PR/PMT are expected to decrease estrogen and progesterone responses in mice, while activators of RIZ1 may enhance responses.

Overectomized female mice are treated with estrogen and target compounds for three days. The animals are sacrificed and examined for uterine wet weight and vaginal cornification. In addition, mammary gland growth in response to estrogen and progesterone is determined. 8 week old female mice are ovariectomized at day 0 and treated with E2 (50 $\mu$g/day)+P4 (1 $\mu$g/day) from day 14–34 (or 21-day releasing hormone pellets containing 0.1 mg of E2 and 10 mg P4; Innovative Research of America). Target compounds are applied together with the hormones. On day 35, the mice are sacrificed and whole mounts prepared and stained. RIZ1 null mutant mice are similarly treated to serve as specificity control for the effects of the target compounds.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention.

What is claimed is:

1. A method of screening for a compound that modulates RIZ histone methyltransferase activity, comprising:

a) contacting a RIZ having at least 70% sequence identity with SEQ ID NO:1, 2, 3 or 4, or a RIZ fragment, said RIZ or RIZ fragment having histone methyltransferase activity, with one or more candidate compounds; and b) determining histone methyltransferase activity of said contacted RIZ or RIZ fragment, wherein a compound that modulates RIZ histone methyltransferase activity is identified.

2. The method of claim 1, wherein said RIZ is RIZ1 of SEQ ID NO:1 or 3.

3. The method of claim 1, wherein said RIZ is RIZ2 of SEQ ID NO:2 or 4.

4. The method of claim 1, wherein said RIZ fragment comprises amino acids 1–200 of human RIZ1 of SEQ ID NO:1 or 3.

5. The method of claim 1, wherein said RIZ fragment comprises amino acids 1–332 of human RIZ1 of SEQ ID NO:1 or 3.

6. The method of claim 1, wherein said RIZ fragment comprises amino acids 1514–1680 of human RIZ1 of SEQ ID NO:1 or 3.

7. The method of claim 1, wherein histone H1 methyltransferase activity is determined.

8. The method of claim 1, wherein histone H3 methyltransferase activity is determined.

9. The method of claim 1, wherein histone H4 methyltransferase activity is determined.

* * * * *

SEQUENCE LISTING

<160> NUMBER OF SEQ ID NOS: 19

<210> SEQ ID NO 1
<211> LENGTH: 1719
<212> TYPE: PRT
<213> ORGANISM: Homo sapiens

<400> SEQUENCE: 1

Met Asn Gln Asn Thr Thr Glu Pro Val Ala Ala Thr Glu Thr Leu Ala
 1               5                  10                  15

Glu Val Pro Glu His Val Leu Arg Gly Leu Pro Glu Glu Val Arg Leu
            20                  25                  30

Phe Pro Ser Ala Val Asp Lys Thr Arg Ile Gly Val Trp Ala Thr Lys

-continued

```
               35                  40                  45
Pro Ile Leu Lys Gly Lys Lys Phe Gly Pro Phe Val Gly Asp Lys Lys
 50                  55                  60
Lys Arg Ser Gln Val Lys Asn Asn Val Tyr Met Trp Glu Val Tyr Tyr
 65                  70                  75                  80
Pro Asn Leu Gly Trp Met Cys Ile Asp Ala Thr Asp Pro Glu Lys Gly
                 85                  90                  95
Asn Trp Leu Arg Tyr Val Asn Trp Ala Cys Ser Gly Glu Glu Gln Asn
                100                 105                 110
Leu Phe Pro Leu Glu Ile Asn Arg Ala Ile Tyr Tyr Lys Thr Leu Lys
                115                 120                 125
Pro Ile Ala Pro Gly Glu Glu Leu Leu Val Trp Tyr Asn Gly Glu Asp
130                 135                 140
Asn Pro Glu Ile Ala Ala Ile Glu Glu Arg Ala Ser Ala Arg
145                 150                 155                 160
Ser Lys Arg Ser Ser Pro Lys Ser Arg Lys Gly Lys Lys Lys Ser Gln
                165                 170                 175
Glu Asn Lys Asn Lys Gly Asn Lys Ile Gln Asp Ile Gln Leu Lys Thr
                180                 185                 190
Ser Glu Pro Asp Phe Thr Ser Ala Asn Met Arg Asp Ser Ala Glu Gly
                195                 200                 205
Pro Lys Glu Asp Glu Glu Lys Pro Ser Ala Ser Ala Leu Glu Gln Pro
                210                 215                 220
Ala Thr Leu Gln Glu Val Ala Ser Gln Glu Val Pro Pro Glu Leu Ala
225                 230                 235                 240
Thr Pro Ala Pro Ala Trp Glu Pro Gln Pro Glu Pro Asp Glu Arg Leu
                245                 250                 255
Glu Ala Ala Ala Cys Glu Val Asn Asp Leu Gly Glu Glu Glu Glu Glu
                260                 265                 270
Glu Glu Glu Glu Asp Glu Glu Glu Glu Asp Asp Asp Asp Asp Glu
                275                 280                 285
Leu Glu Asp Glu Gly Glu Glu Ala Ser Met Pro Asn Glu Asn Ser
                290                 295                 300
Val Lys Glu Pro Glu Ile Arg Cys Asp Glu Lys Pro Glu Asp Leu Leu
305                 310                 315                 320
Glu Glu Pro Lys Thr Thr Ser Glu Glu Thr Leu Glu Asp Cys Ser Glu
                325                 330                 335
Val Thr Pro Ala Met Gln Ile Pro Arg Thr Lys Glu Glu Ala Asn Gly
                340                 345                 350
Asp Val Phe Glu Thr Phe Met Phe Pro Cys Gln His Cys Glu Arg Lys
                355                 360                 365
Phe Thr Thr Lys Gln Gly Leu Glu Arg His Met His Ile His Ile Ser
                370                 375                 380
Thr Val Asn His Ala Phe Lys Cys Lys Tyr Cys Gly Lys Ala Phe Gly
385                 390                 395                 400
Thr Gln Ile Asn Arg Arg Arg His Glu Arg Arg His Glu Ala Gly Leu
                405                 410                 415
Lys Arg Lys Pro Ser Gln Thr Leu Gln Pro Ser Glu Asp Leu Ala Asp
                420                 425                 430
Gly Lys Ala Ser Gly Glu Asn Val Ala Ser Lys Asp Asp Ser Ser Pro
                435                 440                 445
Pro Ser Leu Gly Pro Asp Cys Leu Ile Met Asn Ser Glu Lys Ala Ser
450                 455                 460
```

-continued

```
Gln Asp Thr Ile Asn Ser Ser Val Val Glu Glu Asn Gly Glu Val Lys
465                 470                 475                 480

Glu Leu His Pro Cys Lys Tyr Cys Lys Lys Val Phe Gly Thr His Thr
            485                 490                 495

Asn Met Arg Arg His Gln Arg Arg Val His Glu Arg His Leu Ile Pro
        500                 505                 510

Lys Gly Val Arg Arg Lys Gly Gly Leu Glu Glu Pro Gln Pro Pro Ala
    515                 520                 525

Glu Gln Ala Gln Ala Thr Gln Asn Val Tyr Val Pro Ser Thr Glu Pro
530                 535                 540

Glu Glu Glu Gly Glu Ala Asp Asp Val Tyr Ile Met Asp Ile Ser Ser
545                 550                 555                 560

Asn Ile Ser Glu Asn Leu Asn Tyr Tyr Ile Asp Gly Lys Ile Gln Thr
            565                 570                 575

Asn Asn Asn Thr Ser Asn Cys Asp Val Ile Glu Met Glu Ser Ala Ser
        580                 585                 590

Ala Asp Leu Tyr Gly Ile Asn Cys Leu Leu Thr Pro Val Thr Val Glu
    595                 600                 605

Ile Thr Gln Asn Ile Lys Thr Thr Gln Val Pro Val Thr Glu Asp Leu
610                 615                 620

Pro Lys Glu Pro Leu Gly Ser Thr Asn Ser Glu Ala Lys Lys Arg Arg
625                 630                 635                 640

Thr Ala Ser Pro Pro Ala Leu Pro Lys Ile Lys Ala Glu Thr Asp Ser
            645                 650                 655

Asp Pro Met Val Pro Ser Cys Ser Leu Ser Leu Pro Leu Ser Ile Ser
        660                 665                 670

Thr Thr Glu Ala Val Ser Phe His Lys Glu Lys Ser Val Tyr Leu Ser
    675                 680                 685

Ser Lys Leu Lys Gln Leu Leu Gln Thr Gln Asp Lys Leu Thr Pro Pro
690                 695                 700

Ala Gly Ile Ser Ala Thr Glu Ile Ala Lys Leu Gly Pro Val Cys Val
705                 710                 715                 720

Ser Ala Pro Ala Ser Met Leu Pro Val Thr Ser Ser Arg Phe Lys Arg
            725                 730                 735

Arg Thr Ser Ser Pro Pro Ser Ser Pro Gln His Ser Pro Ala Leu Arg
        740                 745                 750

Asp Phe Gly Lys Pro Ser Asp Gly Lys Ala Ala Trp Thr Asp Ala Gly
    755                 760                 765

Leu Thr Ser Lys Lys Ser Lys Leu Glu Ser His Ser Asp Ser Pro Ala
770                 775                 780

Trp Ser Leu Ser Gly Arg Asp Glu Arg Glu Thr Val Ser Pro Pro Cys
785                 790                 795                 800

Phe Asp Glu Tyr Lys Met Ser Lys Glu Trp Thr Ala Ser Ser Ala Phe
            805                 810                 815

Ser Ser Val Cys Asn Gln Gln Pro Leu Asp Leu Ser Ser Gly Val Lys
        820                 825                 830

Gln Lys Ala Glu Gly Thr Gly Lys Thr Pro Val Gln Trp Glu Ser Val
    835                 840                 845

Leu Asp Leu Ser Val His Lys Lys His Cys Ser Asp Ser Glu Gly Lys
850                 855                 860

Glu Phe Lys Glu Ser His Ser Val Gln Pro Thr Cys Ser Ala Val Lys
865                 870                 875                 880
```

-continued

Lys Arg Lys Pro Thr Thr Cys Met Leu Gln Lys Val Leu Leu Asn Glu
            885                 890                 895

Tyr Asn Gly Ile Asp Leu Pro Val Glu Asn Pro Ala Asp Gly Thr Arg
            900                 905                 910

Ser Pro Ser Pro Cys Lys Ser Leu Glu Ala Gln Pro Asp Pro Asp Leu
            915                 920                 925

Gly Pro Gly Ser Gly Phe Pro Ala Pro Thr Val Glu Ser Thr Pro Asp
        930                 935                 940

Val Cys Pro Ser Ser Pro Ala Leu Gln Thr Pro Ser Leu Ser Ser Gly
945                 950                 955                 960

Gln Leu Pro Pro Leu Leu Ile Pro Thr Asp Pro Ser Ser Pro Pro Pro
            965                 970                 975

Cys Pro Pro Val Leu Thr Val Ala Thr Pro Pro Pro Leu Leu Pro
            980                 985                 990

Thr Val Pro Leu Pro Ala Pro Ser Ser Ala Ser Pro His Pro Cys
            995                 1000                1005

Pro Ser Pro Leu Ser Asn Ala Thr Ala Gln Ser Pro Leu Pro Ile Leu
    1010                1015                1020

Ser Pro Thr Val Ser Pro Ser Pro Ser Pro Ile Pro Val Glu Pro
1025                1030                1035                1040

Leu Met Ser Ala Ala Ser Pro Gly Pro Pro Thr Leu Ser Ser Ser Ser
            1045                1050                1055

Ser Ser Ser Ser Ser Ser Ser Ser Phe Ser Ser Ser Ser Ser Ser Ser
            1060                1065                1070

Ser Pro Ser Pro Pro Leu Ser Ala Ile Ser Ser Val Val Ser Ser
    1075                1080                1085

Gly Asp Asn Leu Glu Ala Ser Leu Pro Met Ile Ser Phe Lys Gln Glu
    1090                1095                1100

Glu Leu Glu Asn Glu Gly Leu Lys Pro Arg Glu Glu Pro Gln Ser Ala
1105                1110                1115                1120

Ala Glu Gln Asp Val Val Gln Glu Thr Phe Asn Lys Asn Phe Val
            1125                1130                1135

Cys Asn Val Cys Glu Ser Pro Phe Leu Ser Ile Lys Asp Leu Thr Lys
            1140                1145                1150

His Leu Ser Ile His Ala Glu Glu Trp Pro Phe Lys Cys Glu Phe Cys
            1155                1160                1165

Val Gln Leu Phe Lys Asp Lys Thr Asp Leu Ser Glu His Arg Phe Leu
            1170                1175                1180

Leu His Gly Val Gly Asn Ile Phe Val Cys Ser Val Cys Lys Lys Glu
1185                1190                1195                1200

Phe Ala Phe Leu Cys Asn Leu Gln Gln His Gln Arg Asp Leu His Pro
            1205                1210                1215

Asp Lys Val Cys Thr His His Glu Phe Glu Ser Gly Thr Leu Arg Pro
            1220                1225                1230

Gln Asn Phe Thr Asp Pro Ser Lys Ala His Val Glu His Met Gln Ser
            1235                1240                1245

Leu Pro Glu Asp Pro Leu Glu Thr Ser Lys Glu Glu Glu Leu Asn
            1250                1255                1260

Asp Ser Ser Glu Glu Leu Tyr Thr Thr Ile Lys Ile Met Ala Ser Gly
1265                1270                1275                1280

Ile Lys Thr Lys Asp Pro Asp Val Arg Leu Gly Leu Asn Gln His Tyr
            1285                1290                1295

Pro Ser Phe Lys Pro Pro Pro Phe Gln Tyr His His Arg Asn Pro Met

-continued

```
              1300                1305                1310
Gly Ile Gly Val Thr Ala Thr Asn Phe Thr Thr His Asn Ile Pro Gln
        1315                1320                1325
Thr Phe Thr Thr Ala Ile Arg Cys Thr Lys Cys Gly Lys Gly Val Asp
    1330                1335                1340
Asn Met Pro Glu Leu His Lys His Ile Leu Ala Cys Ala Ser Ala Ser
1345                1350                1355                1360
Asp Lys Lys Arg Tyr Thr Pro Lys Lys Asn Pro Val Pro Leu Lys Gln
            1365                1370                1375
Thr Val Gln Pro Lys Asn Gly Val Val Leu Asp Asn Ser Gly Lys
        1380                1385                1390
Asn Ala Phe Arg Arg Met Gly Gln Pro Lys Arg Leu Asn Phe Ser Val
            1395                1400                1405
Glu Leu Ser Lys Met Ser Ser Asn Lys Leu Lys Leu Asn Ala Leu Lys
        1410                1415                1420
Lys Lys Asn Gln Leu Val Gln Lys Ala Ile Leu Gln Lys Asn Lys Ser
1425                1430                1435                1440
Ala Lys Gln Lys Ala Asp Leu Lys Asn Ala Cys Glu Ser Ser His
            1445                1450                1455
Ile Cys Pro Tyr Cys Asn Arg Glu Phe Thr Tyr Ile Gly Ser Leu Asn
            1460                1465                1470
Lys His Ala Ala Phe Ser Cys Pro Lys Pro Leu Ser Pro Pro Lys
        1475                1480                1485
Lys Lys Val Ser His Ser Lys Lys Gly His Ser Ser Pro Ala
        1490                1495                1500
Ser Ser Asp Lys Asn Ser Asn Ser Asn His Arg Arg Arg Thr Ala Asp
1505                1510                1515                1520
Ala Glu Ile Lys Met Gln Ser Met Gln Thr Pro Leu Gly Lys Thr Arg
            1525                1530                1535
Ala Arg Ser Ser Gly Pro Thr Gln Val Pro Leu Pro Ser Ser Ser Phe
            1540                1545                1550
Arg Ser Lys Gln Asn Val Lys Phe Ala Ala Ser Val Lys Ser Lys Lys
            1555                1560                1565
Pro Ser Ser Ser Leu Arg Asn Ser Ser Pro Ile Arg Met Ala Lys
        1570                1575                1580
Ile Thr His Val Glu Gly Lys Lys Pro Lys Ala Val Ala Lys Asn His
1585                1590                1595                1600
Ser Ala Gln Leu Ser Ser Lys Thr Ser Arg Ser Leu His Val Arg Val
            1605                1610                1615
Gln Lys Ser Lys Ala Val Leu Gln Ser Lys Ser Thr Leu Ala Ser Lys
            1620                1625                1630
Lys Arg Thr Asp Arg Phe Asn Ile Lys Ser Arg Glu Arg Ser Gly Gly
        1635                1640                1645
Pro Val Thr Arg Ser Leu Gln Leu Ala Ala Ala Asp Leu Ser Glu
    1650                1655                1660
Asn Lys Arg Glu Asp Gly Ser Ala Lys Gln Glu Leu Lys Asp Phe Ser
1665                1670                1675                1680
Tyr Ser Leu Arg Leu Ala Ser Arg Cys Ser Pro Ala Ala Pro Tyr
            1685                1690                1695
Ile Thr Arg Gln Tyr Arg Lys Val Lys Ala Pro Ala Ala Ala Gln Phe
            1700                1705                1710
Gln Gly Pro Phe Phe Lys Glu
        1715
```

-continued

<210> SEQ ID NO 2
<211> LENGTH: 1518
<212> TYPE: PRT
<213> ORGANISM: Homo sapiens

<400> SEQUENCE: 2

Met Arg Asp Ser Ala Glu Gly Pro Lys Glu Asp Glu Lys Pro Ser
1               5                   10                  15

Ala Ser Ala Leu Glu Gln Pro Ala Thr Leu Gln Glu Val Ala Ser Gln
            20                  25                  30

Glu Val Pro Pro Glu Leu Ala Thr Pro Ala Pro Ala Trp Glu Pro Gln
            35                  40                  45

Pro Glu Pro Asp Glu Arg Leu Glu Ala Ala Cys Glu Val Asn Asp
    50                  55                  60

Leu Gly Glu Glu Glu Glu Glu Glu Glu Asp Glu Glu Glu
65                  70                  75                  80

Glu Asp Asp Asp Asp Glu Leu Glu Asp Gly Glu Glu Glu Ala
                85                  90                  95

Ser Met Pro Asn Glu Asn Ser Val Lys Glu Pro Glu Ile Arg Cys Asp
            100                 105                 110

Glu Lys Pro Glu Asp Leu Leu Glu Glu Pro Lys Thr Thr Ser Glu Glu
            115                 120                 125

Thr Leu Glu Asp Cys Ser Glu Val Thr Pro Ala Met Gln Ile Pro Arg
    130                 135                 140

Thr Lys Glu Glu Ala Asn Gly Asp Val Phe Glu Thr Phe Met Phe Pro
145                 150                 155                 160

Cys Gln His Cys Glu Arg Lys Phe Thr Thr Lys Gln Gly Leu Glu Arg
                165                 170                 175

His Met His Ile His Ile Ser Thr Val Asn His Ala Phe Lys Cys Lys
            180                 185                 190

Tyr Cys Gly Lys Ala Phe Gly Thr Gln Ile Asn Arg Arg Arg His Glu
        195                 200                 205

Arg Arg His Glu Ala Gly Leu Lys Arg Lys Pro Ser Gln Thr Leu Gln
    210                 215                 220

Pro Ser Glu Asp Leu Ala Asp Gly Lys Ala Ser Gly Glu Asn Val Ala
225                 230                 235                 240

Ser Lys Asp Asp Ser Ser Pro Pro Ser Leu Gly Pro Asp Cys Leu Ile
                245                 250                 255

Met Asn Ser Glu Lys Ala Ser Gln Asp Thr Ile Asn Ser Ser Val Val
            260                 265                 270

Glu Glu Asn Gly Glu Val Lys Glu Leu His Pro Cys Lys Tyr Cys Lys
        275                 280                 285

Lys Val Phe Gly Thr His Thr Asn Met Arg Arg His Gln Arg Arg Val
    290                 295                 300

His Glu Arg His Leu Ile Pro Lys Gly Val Arg Arg Lys Gly Gly Leu
305                 310                 315                 320

Glu Glu Pro Gln Pro Pro Ala Glu Gln Ala Gln Ala Thr Gln Asn Val
                325                 330                 335

Tyr Val Pro Ser Thr Glu Pro Glu Glu Gly Glu Ala Asp Asp Val
            340                 345                 350

Tyr Ile Met Asp Ile Ser Ser Asn Ile Ser Glu Asn Leu Asn Tyr Tyr
        355                 360                 365

Ile Asp Gly Lys Ile Gln Thr Asn Asn Asn Thr Ser Asn Cys Asp Val

```
            370             375             380
Ile Glu Met Glu Ser Ala Ser Ala Asp Leu Tyr Gly Ile Asn Cys Leu
385                 390                 395                 400

Leu Thr Pro Val Thr Val Glu Ile Thr Gln Asn Ile Lys Thr Thr Gln
                405                 410                 415

Val Pro Val Thr Glu Asp Leu Pro Lys Glu Pro Leu Gly Ser Thr Asn
            420                 425                 430

Ser Glu Ala Lys Lys Arg Arg Thr Ala Ser Pro Pro Ala Leu Pro Lys
        435                 440                 445

Ile Lys Ala Glu Thr Asp Ser Asp Pro Met Val Pro Ser Cys Ser Leu
450                 455                 460

Ser Leu Pro Leu Ser Ile Ser Thr Thr Glu Ala Val Ser Phe His Lys
465                 470                 475                 480

Glu Lys Ser Val Tyr Leu Ser Ser Lys Leu Lys Gln Leu Leu Gln Thr
                485                 490                 495

Gln Asp Lys Leu Thr Pro Pro Ala Gly Ile Ser Ala Thr Glu Ile Ala
            500                 505                 510

Lys Leu Gly Pro Val Cys Val Ser Ala Pro Ala Ser Met Leu Pro Val
        515                 520                 525

Thr Ser Ser Arg Phe Lys Arg Arg Thr Ser Ser Pro Pro Ser Ser Pro
530                 535                 540

Gln His Ser Pro Ala Leu Arg Asp Phe Gly Lys Pro Ser Asp Gly Lys
545                 550                 555                 560

Ala Ala Trp Thr Asp Ala Gly Leu Thr Ser Lys Ser Lys Leu Glu
                565                 570                 575

Ser His Ser Asp Ser Pro Ala Trp Ser Leu Ser Gly Arg Asp Glu Arg
            580                 585                 590

Glu Thr Val Ser Pro Pro Cys Phe Asp Glu Tyr Lys Met Ser Lys Glu
                595                 600                 605

Trp Thr Ala Ser Ser Ala Phe Ser Ser Val Cys Asn Gln Gln Pro Leu
            610                 615                 620

Asp Leu Ser Ser Gly Val Lys Gln Lys Ala Glu Gly Thr Gly Lys Thr
625                 630                 635                 640

Pro Val Gln Trp Glu Ser Val Leu Asp Leu Ser Val His Lys Lys His
                645                 650                 655

Cys Ser Asp Ser Glu Gly Lys Glu Phe Lys Glu Ser His Ser Val Gln
                660                 665                 670

Pro Thr Cys Ser Ala Val Lys Lys Arg Lys Pro Thr Thr Cys Met Leu
            675                 680                 685

Gln Lys Val Leu Leu Asn Glu Tyr Asn Gly Ile Asp Leu Pro Val Glu
        690                 695                 700

Asn Pro Ala Asp Gly Thr Arg Ser Pro Ser Pro Cys Lys Ser Leu Glu
705                 710                 715                 720

Ala Gln Pro Asp Pro Asp Leu Gly Pro Gly Ser Phe Pro Ala Pro
            725                 730                 735

Thr Val Glu Ser Thr Pro Asp Val Cys Pro Ser Ser Pro Ala Leu Gln
                740                 745                 750

Thr Pro Ser Leu Ser Ser Gly Gln Leu Pro Pro Leu Leu Ile Pro Thr
            755                 760                 765

Asp Pro Ser Ser Pro Pro Cys Pro Pro Val Leu Thr Val Ala Thr
        770                 775                 780

Pro Pro Pro Pro Leu Leu Pro Thr Val Pro Leu Pro Ala Pro Ser Ser
785                 790                 795                 800
```

-continued

```
Ser Ala Ser Pro His Pro Cys Pro Ser Pro Leu Ser Asn Ala Thr Ala
                805                 810                 815
Gln Ser Pro Leu Pro Ile Leu Ser Pro Thr Val Ser Pro Ser Pro Ser
                820                 825                 830
Pro Ile Pro Pro Val Glu Pro Leu Met Ser Ala Ala Ser Pro Gly Pro
                835                 840                 845
Pro Thr Leu Ser Ser Ser Ser Ser Ser Ser Ser Ser Ser Ser Ser Phe
                850                 855                 860
Ser Ser Ser Ser Ser Ser Ser Pro Ser Pro Pro Pro Leu Ser Ala
865                 870                 875                 880
Ile Ser Ser Val Val Ser Ser Gly Asp Asn Leu Glu Ala Ser Leu Pro
                885                 890                 895
Met Ile Ser Phe Lys Gln Glu Glu Leu Glu Asn Glu Gly Leu Lys Pro
                900                 905                 910
Arg Glu Glu Pro Gln Ser Ala Ala Glu Gln Asp Val Val Gln Glu
                915                 920                 925
Thr Phe Asn Lys Asn Phe Val Cys Asn Val Cys Glu Ser Pro Phe Leu
                930                 935                 940
Ser Ile Lys Asp Leu Thr Lys His Leu Ser Ile His Ala Glu Glu Trp
945                 950                 955                 960
Pro Phe Lys Cys Glu Phe Cys Val Gln Leu Phe Lys Asp Lys Thr Asp
                965                 970                 975
Leu Ser Glu His Arg Phe Leu Leu His Gly Val Gly Asn Ile Phe Val
                980                 985                 990
Cys Ser Val Cys Lys Lys Glu Phe Ala Phe Leu Cys Asn Leu Gln Gln
                995                 1000                1005
His Gln Arg Asp Leu His Pro Asp Lys Val Cys Thr His His Glu Phe
                1010                1015                1020
Glu Ser Gly Thr Leu Arg Pro Gln Asn Phe Thr Asp Pro Ser Lys Ala
1025                1030                1035                1040
His Val Glu His Met Gln Ser Leu Pro Glu Asp Pro Leu Glu Thr Ser
                1045                1050                1055
Lys Glu Glu Glu Glu Leu Asn Asp Ser Ser Glu Glu Leu Tyr Thr Thr
                1060                1065                1070
Ile Lys Ile Met Ala Ser Gly Ile Lys Thr Lys Asp Pro Asp Val Arg
                1075                1080                1085
Leu Gly Leu Asn Gln His Tyr Pro Ser Phe Lys Pro Pro Pro Phe Gln
                1090                1095                1100
Tyr His His Arg Asn Pro Met Gly Ile Gly Val Thr Ala Thr Asn Phe
1105                1110                1115                1120
Thr Thr His Asn Ile Pro Gln Thr Phe Thr Thr Ala Ile Arg Cys Thr
                1125                1130                1135
Lys Cys Gly Lys Gly Val Asp Asn Met Pro Glu Leu His Lys His Ile
                1140                1145                1150
Leu Ala Cys Ala Ser Ala Ser Asp Lys Lys Arg Tyr Thr Pro Lys Lys
                1155                1160                1165
Asn Pro Val Pro Leu Lys Gln Thr Val Gln Pro Lys Asn Gly Val Val
                1170                1175                1180
Val Leu Asp Asn Ser Gly Lys Asn Ala Phe Arg Arg Met Gly Gln Pro
1185                1190                1195                1200
Lys Arg Leu Asn Phe Ser Val Glu Leu Ser Lys Met Ser Ser Asn Lys
                1205                1210                1215
```

-continued

```
Leu Lys Leu Asn Ala Leu Lys Lys Asn Gln Leu Val Gln Lys Ala
        1220                1225                1230

Ile Leu Gln Lys Asn Lys Ser Ala Lys Gln Lys Ala Asp Leu Lys Asn
            1235                1240                1245

Ala Cys Glu Ser Ser His Ile Cys Pro Tyr Cys Asn Arg Glu Phe
    1250                1255                1260

Thr Tyr Ile Gly Ser Leu Asn Lys His Ala Ala Phe Ser Cys Pro Lys
1265                1270                1275                1280

Lys Pro Leu Ser Pro Pro Lys Lys Val Ser His Ser Ser Lys Lys
            1285                1290                1295

Gly Gly His Ser Ser Pro Ala Ser Ser Asp Lys Asn Ser Asn Ser Asn
        1300                1305                1310

His Arg Arg Thr Ala Asp Ala Glu Ile Lys Met Gln Ser Met Gln
        1315                1320                1325

Thr Pro Leu Gly Lys Thr Arg Ala Arg Ser Ser Gly Pro Thr Gln Val
        1330                1335                1340

Pro Leu Pro Ser Ser Ser Phe Arg Ser Lys Gln Asn Val Lys Phe Ala
1345                1350                1355                1360

Ala Ser Val Lys Ser Lys Pro Ser Ser Ser Leu Arg Asn Ser
            1365                1370                1375

Ser Pro Ile Arg Met Ala Lys Ile Thr His Val Glu Gly Lys Lys Pro
        1380                1385                1390

Lys Ala Val Ala Lys Asn His Ser Ala Gln Leu Ser Ser Lys Thr Ser
            1395                1400                1405

Arg Ser Leu His Val Arg Val Gln Lys Ser Lys Ala Val Leu Gln Ser
        1410                1415                1420

Lys Ser Thr Leu Ala Ser Lys Lys Arg Thr Asp Arg Phe Asn Ile Lys
1425                1430                1435                1440

Ser Arg Glu Arg Ser Gly Gly Pro Val Thr Arg Ser Leu Gln Leu Ala
            1445                1450                1455

Ala Ala Ala Asp Leu Ser Glu Asn Lys Arg Glu Asp Gly Ser Ala Lys
            1460                1465                1470

Gln Glu Leu Lys Asp Phe Ser Tyr Ser Leu Arg Leu Ala Ser Arg Cys
        1475                1480                1485

Ser Pro Pro Ala Ala Pro Tyr Ile Thr Arg Gln Tyr Arg Lys Val Lys
        1490                1495                1500

Ala Pro Ala Ala Ala Gln Phe Gln Gly Pro Phe Phe Lys Glu
1505                1510                1515
```

<210> SEQ ID NO 3
<211> LENGTH: 1706
<212> TYPE: PRT
<213> ORGANISM: Rattus sp.

<400> SEQUENCE: 3

```
Met His Gln Asn Thr Glu Ser Val Ala Ala Thr Glu Thr Leu Ala Glu
1               5                   10                  15

Val Pro Glu His Val Leu Arg Gly Leu Pro Glu Glu Val Arg Leu Phe
            20                  25                  30

Pro Ser Ala Val Asp Lys Thr Arg Ile Gly Val Trp Ala Thr Lys Pro
        35                  40                  45

Ile Leu Lys Gly Lys Lys Phe Gly Pro Phe Val Gly Asp Lys Lys Lys
    50                  55                  60

Arg Ser Gln Val Arg Asn Asn Val Tyr Met Trp Glu Val Tyr Tyr Pro
65                  70                  75                  80
```

-continued

```
Asn Leu Gly Trp Met Cys Ile Asp Ala Thr Asp Pro Glu Lys Gly Asn
                85                  90                  95
Trp Leu Arg Tyr Val Asn Trp Ala Cys Ser Gly Glu Glu Gln Asn Leu
               100                 105                 110
Phe Pro Leu Glu Ile Asn Arg Ala Ile Tyr Tyr Lys Thr Leu Lys Pro
           115                 120                 125
Ile Ala Pro Gly Glu Glu Leu Leu Val Trp Tyr Asn Gly Glu Asp Asn
       130                 135                 140
Pro Glu Ile Ala Ala Ala Ile Glu Glu Glu Arg Ala Ser Ala Arg Ser
145                 150                 155                 160
Lys Arg Ser Ser Pro Lys Ser Arg Arg Gly Lys Lys Ser His Glu
                165                 170                 175
Asn Lys Asn Lys Gly Ile Arg Thr His Pro Thr Gln Leu Lys Ala Ser
                180                 185                 190
Glu Leu Asp Ser Thr Phe Ala Asn Met Arg Gly Ser Ala Glu Gly Pro
            195                 200                 205
Lys Glu Glu Asp Glu Arg Pro Leu Ala Ser Ala Pro Glu Gln Pro Ala
    210                 215                 220
Pro Leu Pro Glu Val Gly Asn Gln Asp Ala Val Pro Gln Val Ala Ile
225                 230                 235                 240
Pro Leu Pro Ala Cys Glu Pro Gln Pro Glu Val Asp Gly Lys Gln Glu
                245                 250                 255
Val Thr Asp Cys Glu Val Asn Asp Val Glu Glu Glu Leu Glu Glu
                260                 265                 270
Glu Glu Glu Leu Glu Glu Glu Glu Glu Glu Leu Gly Glu Asp Gly
            275                 280                 285
Val Glu Glu Ala Asp Met Pro Asn Glu Ser Ser Ala Lys Glu Pro Glu
    290                 295                 300
Ile Arg Cys Glu Glu Lys Pro Glu Asp Leu Leu Glu Glu Pro Gln Ser
305                 310                 315                 320
Met Ser Asn Glu Ala Arg Glu Asp Ser Pro Asp Val Thr Pro Pro Pro
                325                 330                 335
His Thr Pro Arg Ala Arg Glu Glu Ala Asn Gly Asp Val Leu Glu Thr
            340                 345                 350
Phe Met Phe Pro Cys Gln His Cys Glu Arg Lys Phe Ala Thr Lys Gln
        355                 360                 365
Gly Leu Glu Arg His Met His Ile His Ile Ser Thr Ile Asn His Ala
370                 375                 380
Phe Lys Cys Lys Tyr Cys Gly Lys Arg Phe Gly Thr Gln Ile Asn Arg
385                 390                 395                 400
Arg Arg His Glu Arg Arg His Glu Thr Gly Leu Lys Arg Arg Pro Ser
                405                 410                 415
Met Thr Leu Gln Ser Ser Glu Asp Pro Asp Asp Gly Lys Gly Glu Asn
            420                 425                 430
Val Thr Ser Lys Asp Glu Ser Ser Pro Pro Gln Leu Gly Gln Asp Cys
        435                 440                 445
Leu Ile Leu Asn Ser Glu Lys Thr Ser Gln Glu Val Leu Asn Ser Ser
    450                 455                 460
Phe Val Glu Glu Asn Gly Glu Val Lys Glu Leu His Pro Cys Lys Tyr
465                 470                 475                 480
Cys Lys Lys Val Phe Gly Thr His Thr Asn Met Arg Arg His Gln Arg
                485                 490                 495
```

```
Arg Val His Glu Arg His Leu Ile Pro Lys Gly Val Arg Arg Lys Gly
            500                 505                 510

Gly Leu Leu Glu Glu Pro Gln Pro Ala Glu Gln Ala Pro Pro Ser
            515                 520                 525

Gln Asn Val Tyr Val Pro Ser Thr Glu Pro Glu Glu Gly Glu Thr
            530                 535                 540

Asp Asp Val Tyr Ile Met Asp Ile Ser Ser Asn Ile Ser Glu Asn Leu
545                 550                 555                 560

Asn Tyr Tyr Ile Asp Gly Lys Ile Gln Thr Asn Ser Ser Thr Ser Asn
                565                 570                 575

Cys Asp Val Ile Glu Met Glu Ser Asn Ser Ala His Leu Tyr Gly Ile
            580                 585                 590

Asp Cys Leu Leu Thr Pro Val Thr Val Glu Ile Thr Gln Asn Ile Lys
            595                 600                 605

Ser Thr Gln Val Ser Val Thr Asp Asp Leu Leu Lys Asp Ser Pro Ser
            610                 615                 620

Ser Thr Asn Cys Glu Ser Lys Lys Arg Arg Thr Ala Ser Pro Pro Val
625                 630                 635                 640

Leu Pro Lys Ile Lys Thr Glu Thr Glu Ser Asp Ser Thr Ala Pro Ser
                645                 650                 655

Cys Ser Leu Ser Leu Pro Leu Ser Ile Ser Thr Ala Glu Val Val Ser
            660                 665                 670

Phe His Lys Glu Lys Gly Val Tyr Leu Ser Ser Lys Leu Lys Gln Leu
            675                 680                 685

Leu Gln Thr Gln Asp Lys Leu Thr Leu Pro Ala Gly Phe Ser Ala Ala
            690                 695                 700

Glu Ile Pro Lys Leu Gly Pro Val Cys Ala Ser Ala Pro Ala Ser Met
705                 710                 715                 720

Leu Pro Val Thr Ser Ser Arg Phe Lys Arg Arg Thr Ser Ser Pro Pro
                725                 730                 735

Ser Ser Pro Gln His Ser Pro Ala Leu Arg Asp Phe Gly Lys Pro Asn
            740                 745                 750

Asp Gly Lys Ala Ala Trp Thr Asp Thr Val Leu Thr Ser Lys Lys Pro
            755                 760                 765

Lys Leu Glu Ser Arg Ser Asp Ser Pro Ala Trp Ser Leu Ser Gly Arg
            770                 775                 780

Asp Glu Arg Glu Thr Gly Ser Pro Pro Cys Phe Asp Glu Tyr Lys Ile
785                 790                 795                 800

Ser Lys Glu Trp Ala Ala Ser Ser Thr Phe Ser Ser Val Cys Asn Gln
                805                 810                 815

Gln Pro Leu Asp Leu Ser Ser Gly Val Lys Gln Lys Ser Glu Gly Thr
            820                 825                 830

Gly Lys Thr Pro Val Pro Trp Glu Ser Val Leu Asp Leu Ser Val His
            835                 840                 845

Lys Lys Pro Cys Asp Ser Glu Gly Lys Glu Phe Lys Glu Asn His Leu
850                 855                 860

Ala Gln Pro Ala Ala Lys Lys Lys Pro Thr Thr Cys Met Leu Gln
865                 870                 875                 880

Lys Val Leu Leu Asn Glu Tyr Asn Gly Val Ser Leu Pro Thr Glu Thr
                885                 890                 895

Thr Pro Glu Val Thr Arg Ser Pro Ser Pro Cys Lys Ser Pro Asp Thr
            900                 905                 910

Gln Pro Asp Pro Glu Leu Gly Pro Asp Ser Ser Cys Ser Val Pro Thr
```

-continued

```
            915                 920                 925
Ala Glu Ser Pro Pro Glu Val Val Gly Pro Ser Ser Pro Pro Leu Gln
930                 935                 940
Thr Ala Ser Leu Ser Ser Gly Gln Leu Pro Pro Leu Leu Thr Pro Thr
945                 950                 955                 960
Glu Pro Ser Ser Pro Pro Cys Pro Pro Val Leu Thr Val Ala Thr
                965                 970                 975
Pro Pro Pro Pro Leu Leu Pro Thr Val Pro Leu Ser His Pro Ser Ser
                980                 985                 990
Asp Ala Ser Pro Gln Gln Cys Pro Ser Pro Phe Ser Asn Thr Thr Ala
                995                 1000                1005
Gln Ser Pro Leu Pro Ile Leu Ser Pro Thr Val Ser Pro Ser Pro Ser
            1010                1015                1020
Pro Ile Pro Pro Val Glu Pro Leu Met Ser Ala Ala Ser Pro Gly Pro
1025                1030                1035                1040
Pro Thr Leu Ser Ser Ser Ser Ser Ser Ser Ser Phe Pro Ser Ser
                1045                1050                1055
Ser Cys Ser Ser Thr Ser Pro Ser Pro Pro Leu Ser Ala Val Ser
                1060                1065                1070
Ser Val Val Ser Ser Gly Asp Asn Leu Glu Ala Ser Leu Pro Ala Val
                1075                1080                1085
Thr Phe Lys Gln Glu Glu Ser Glu Ser Glu Gly Leu Lys Pro Lys Glu
                1090                1095                1100
Glu Ala Pro Pro Ala Gly Gly Gln Ser Val Val Gln Glu Thr Phe Ser
1105                1110                1115                1120
Lys Asn Phe Ile Cys Asn Val Cys Glu Ser Pro Phe Leu Ser Ile Lys
                1125                1130                1135
Asp Leu Thr Lys His Leu Ser Val His Ala Glu Glu Trp Pro Phe Lys
                1140                1145                1150
Cys Glu Phe Cys Val Gln Leu Phe Lys Val Lys Thr Asp Leu Ser Glu
                1155                1160                1165
His Arg Phe Leu Leu His Gly Val Gly Asn Ile Phe Val Cys Ser Val
                1170                1175                1180
Cys Lys Lys Glu Phe Ala Phe Leu Cys Asn Leu Gln Gln His Gln Arg
1185                1190                1195                1200
Asp Leu His Pro Asp Glu Val Cys Thr His His Glu Phe Glu Ser Gly
                1205                1210                1215
Thr Leu Arg Pro Gln Asn Phe Thr Asp Pro Ser Lys Ala Asn Val Glu
                1220                1225                1230
His Met Pro Ser Leu Pro Glu Glu Pro Leu Glu Thr Ser Arg Glu Glu
                1235                1240                1245
Glu Leu Asn Asp Ser Ser Glu Glu Leu Tyr Thr Thr Ile Lys Ile Met
                1250                1255                1260
Ala Ser Gly Ile Lys Thr Lys Asp Pro Asp Val Arg Leu Gly Leu Asn
1265                1270                1275                1280
Gln His Tyr Pro Ser Phe Lys Pro Pro Phe Gln Tyr His His Arg
                1285                1290                1295
Asn Pro Met Gly Ile Gly Val Thr Ala Thr Asn Phe Thr Thr His Asn
                1300                1305                1310
Ile Pro Gln Thr Phe Thr Thr Ala Ile Arg Cys Thr Lys Cys Gly Lys
                1315                1320                1325
Gly Val Asp Asn Met Pro Glu Leu His Lys His Ile Leu Ala Cys Ala
                1330                1335                1340
```

```
Ser Ala Ser Asp Lys Lys Arg Tyr Thr Pro Lys Lys Asn Pro Val Pro
1345                1350                1355                1360

Leu Lys Gln Thr Val Gln Pro Lys Asn Gly Val Val Leu Asp Asn
        1365                1370                1375

Ser Gly Lys Asn Ala Phe Arg Arg Met Gly Gln Pro Lys Arg Leu Ser
            1380                1385                1390

Phe Asn Val Glu Leu Gly Lys Met Ser Pro Asn Lys Leu Lys Leu Ser
        1395                1400                1405

Ala Leu Lys Lys Lys Asn Gln Leu Val Gln Lys Ala Ile Leu Gln Lys
    1410                1415                1420

Asn Arg Ala Ala Lys Gln Lys Ala Asp Leu Arg Asp Thr Ser Glu Ala
1425                1430                1435                1440

Ser Ser His Ile Cys Pro Tyr Cys Asp Arg Glu Phe Thr Tyr Ile Gly
                1445                1450                1455

Ser Leu Asn Lys His Ala Ala Phe Ser Cys Pro Lys Lys Pro Leu Ser
            1460                1465                1470

Pro Ser Lys Arg Lys Val Ser His Ser Ser Lys Lys Gly Gly His Ala
        1475                1480                1485

Ser Ser Ser Ser Ser Asp Arg Asn Ser Ser Cys His Pro Arg Arg Arg
    1490                1495                1500

Thr Ala Asp Thr Glu Ile Lys Met Gln Ser Thr Gln Ala Pro Leu Gly
1505                1510                1515                1520

Lys Thr Arg Ala Arg Ser Thr Gly Pro Ala Gln Ala Ser Leu Pro Ser
                1525                1530                1535

Ser Ser Phe Arg Ser Arg Gln Asn Val Lys Phe Ala Ala Ser Val Lys
            1540                1545                1550

Ser Lys Lys Ala Ser Ser Ser Leu Arg Asn Ser Ser Pro Ile Arg
        1555                1560                1565

Met Ala Lys Ile Thr His Val Glu Gly Lys Lys Pro Lys Ala Val Ala
    1570                1575                1580

Lys Ser His Ser Ala Gln Leu Ser Ser Lys Ser Ser Arg Gly Leu His
1585                1590                1595                1600

Val Arg Val Gln Lys Ser Lys Ala Val Ile Gln Ser Lys Thr Ala Leu
                1605                1610                1615

Ala Ser Lys Arg Arg Thr Asp Arg Phe Ile Val Lys Ser Arg Glu Arg
            1620                1625                1630

Ser Gly Gly Pro Ile Thr Arg Ser Leu Gln Leu Ala Ala Ala Asp
        1635                1640                1645

Leu Ser Glu Ser Arg Arg Glu Asp Ser Ser Ala Arg His Glu Leu Lys
    1650                1655                1660

Asp Phe Ser Tyr Ser Leu Arg Leu Ala Ser Arg Cys Gly Ser Ser Thr
1665                1670                1675                1680

Ala Ser Tyr Ile Thr Arg Gln Cys Arg Lys Val Lys Ala Ala Ala Ala
                1685                1690                1695

Thr Pro Phe Gln Gly Pro Phe Leu Lys Glu
            1700                1705

<210> SEQ ID NO 4
<211> LENGTH: 1506
<212> TYPE: PRT
<213> ORGANISM: Rattus sp.

<400> SEQUENCE: 4

Met Arg Gly Ser Ala Glu Gly Pro Lys Glu Glu Asp Glu Arg Pro Leu
```

-continued

```
  1               5                  10                 15
Ala Ser Ala Pro Glu Gln Pro Ala Pro Leu Pro Glu Val Gly Asn Gln
             20                 25                 30

Asp Ala Val Pro Gln Val Ala Ile Pro Leu Pro Ala Cys Glu Pro Gln
             35                 40                 45

Pro Glu Val Asp Gly Lys Gln Glu Val Thr Asp Cys Glu Val Asn Asp
             50                 55                 60

Val Glu Glu Glu Glu Leu Glu Glu Glu Glu Leu Glu Glu Glu Glu Glu
 65                 70                 75                 80

Glu Glu Glu Leu Gly Glu Asp Gly Val Glu Glu Ala Asp Met Pro Asn
                 85                 90                 95

Glu Ser Ser Ala Lys Glu Pro Glu Ile Arg Cys Glu Glu Lys Pro Glu
                100                105                110

Asp Leu Leu Glu Glu Pro Gln Ser Met Ser Asn Glu Ala Arg Glu Asp
             115                120                125

Ser Pro Asp Val Thr Pro Pro His Thr Pro Arg Ala Arg Glu Glu
             130                135                140

Ala Asn Gly Asp Val Leu Glu Thr Phe Met Phe Pro Cys Gln His Cys
145                150                155                160

Glu Arg Lys Phe Ala Thr Lys Gln Gly Leu Glu Arg His Met His Ile
                165                170                175

His Ile Ser Thr Ile Asn His Ala Phe Lys Cys Lys Tyr Cys Gly Lys
                180                185                190

Arg Phe Gly Thr Gln Ile Asn Arg Arg Arg His Glu Arg Arg His Glu
                195                200                205

Thr Gly Leu Lys Arg Arg Pro Ser Met Thr Leu Gln Ser Ser Glu Asp
                210                215                220

Pro Asp Asp Gly Lys Gly Glu Asn Val Thr Ser Lys Asp Glu Ser Ser
225                230                235                240

Pro Pro Gln Leu Gly Gln Asp Cys Leu Ile Leu Asn Ser Glu Lys Thr
                245                250                255

Ser Gln Glu Val Leu Asn Ser Ser Phe Val Glu Glu Asn Gly Glu Val
                260                265                270

Lys Glu Leu His Pro Cys Lys Tyr Cys Lys Lys Val Phe Gly Thr His
                275                280                285

Thr Asn Met Arg Arg His Gln Arg Arg Val His Glu Arg His Leu Ile
                290                295                300

Pro Lys Gly Val Arg Arg Lys Gly Gly Leu Leu Glu Glu Pro Gln Pro
305                310                315                320

Pro Ala Glu Gln Ala Pro Pro Ser Gln Asn Val Tyr Val Pro Ser Thr
                325                330                335

Glu Pro Glu Glu Glu Gly Glu Thr Asp Asp Val Tyr Ile Met Asp Ile
                340                345                350

Ser Ser Asn Ile Ser Glu Asn Leu Asn Tyr Tyr Ile Asp Gly Lys Ile
                355                360                365

Gln Thr Asn Ser Ser Thr Ser Asn Cys Asp Val Ile Glu Met Glu Ser
                370                375                380

Asn Ser Ala His Leu Tyr Gly Ile Asp Cys Leu Leu Thr Pro Val Thr
385                390                395                400

Val Glu Ile Thr Gln Asn Ile Lys Ser Thr Gln Val Ser Val Thr Asp
                405                410                415

Asp Leu Leu Lys Asp Ser Pro Ser Ser Thr Asn Cys Glu Ser Lys Lys
                420                425                430
```

-continued

```
Arg Arg Thr Ala Ser Pro Pro Val Leu Pro Lys Ile Lys Thr Glu Thr
        435                 440                 445
Glu Ser Asp Ser Thr Ala Pro Ser Cys Ser Leu Ser Leu Pro Leu Ser
        450                 455                 460
Ile Ser Thr Ala Glu Val Val Ser Phe His Lys Glu Lys Gly Val Tyr
465                 470                 475                 480
Leu Ser Ser Lys Leu Lys Gln Leu Leu Gln Thr Gln Asp Lys Leu Thr
                485                 490                 495
Leu Pro Ala Gly Phe Ser Ala Ala Glu Ile Pro Lys Leu Gly Pro Val
                500                 505                 510
Cys Ala Ser Ala Pro Ala Ser Met Leu Pro Val Thr Ser Ser Arg Phe
                515                 520                 525
Lys Arg Arg Thr Ser Ser Pro Pro Ser Ser Pro Gln His Ser Pro Ala
        530                 535                 540
Leu Arg Asp Phe Gly Lys Pro Asn Asp Gly Lys Ala Ala Trp Thr Asp
545                 550                 555                 560
Thr Val Leu Thr Ser Lys Lys Pro Lys Leu Glu Ser Arg Ser Asp Ser
                565                 570                 575
Pro Ala Trp Ser Leu Ser Gly Arg Asp Glu Arg Glu Thr Gly Ser Pro
                580                 585                 590
Pro Cys Phe Asp Glu Tyr Lys Ile Ser Lys Glu Trp Ala Ala Ser Ser
                595                 600                 605
Thr Phe Ser Ser Val Cys Asn Gln Gln Pro Leu Asp Leu Ser Ser Gly
        610                 615                 620
Val Lys Gln Lys Ser Glu Gly Thr Gly Lys Thr Pro Val Pro Trp Glu
625                 630                 635                 640
Ser Val Leu Asp Leu Ser Val His Lys Lys Pro Cys Asp Ser Glu Gly
                645                 650                 655
Lys Glu Phe Lys Glu Asn His Leu Ala Gln Pro Ala Ala Lys Lys Lys
                660                 665                 670
Lys Pro Thr Thr Cys Met Leu Gln Lys Val Leu Leu Asn Glu Tyr Asn
        675                 680                 685
Gly Val Ser Leu Pro Thr Glu Thr Thr Pro Glu Val Thr Arg Ser Pro
690                 695                 700
Ser Pro Cys Lys Ser Pro Asp Thr Gln Pro Asp Pro Glu Leu Gly Pro
705                 710                 715                 720
Asp Ser Ser Cys Ser Val Pro Thr Ala Glu Ser Pro Glu Val Val
                725                 730                 735
Gly Pro Ser Ser Pro Leu Gln Thr Ala Ser Leu Ser Ser Gly Gln
                740                 745                 750
Leu Pro Pro Leu Leu Thr Pro Thr Glu Pro Ser Ser Pro Pro Cys
        755                 760                 765
Pro Pro Val Leu Thr Val Ala Thr Pro Pro Leu Leu Pro Thr
        770                 775                 780
Val Pro Leu Ser His Pro Ser Ser Asp Ala Ser Pro Gln Gln Cys Pro
785                 790                 795                 800
Ser Pro Phe Ser Asn Thr Thr Ala Gln Ser Pro Leu Pro Ile Leu Ser
                805                 810                 815
Pro Thr Val Ser Pro Ser Pro Ser Ile Pro Pro Val Glu Pro Leu
                820                 825                 830
Met Ser Ala Ala Ser Pro Gly Pro Pro Thr Leu Ser Ser Ser Ser Ser
                835                 840                 845
```

```
Ser Ser Ser Ser Phe Pro Ser Ser Cys Ser Ser Thr Ser Pro Ser
    850                 855                 860

Pro Pro Pro Leu Ser Ala Val Ser Ser Val Val Ser Ser Gly Asp Asn
865                 870                 875                 880

Leu Glu Ala Ser Leu Pro Ala Val Thr Phe Lys Gln Glu Glu Ser Glu
                885                 890                 895

Ser Glu Gly Leu Lys Pro Lys Glu Glu Ala Pro Pro Ala Gly Gly Gln
            900                 905                 910

Ser Val Val Gln Glu Thr Phe Ser Lys Asn Phe Ile Cys Asn Val Cys
            915                 920                 925

Glu Ser Pro Phe Leu Ser Ile Lys Asp Leu Thr Lys His Leu Ser Val
    930                 935                 940

His Ala Glu Glu Trp Pro Phe Lys Cys Glu Phe Cys Val Gln Leu Phe
945                 950                 955                 960

Lys Val Lys Thr Asp Leu Ser Glu His Arg Phe Leu Leu His Gly Val
                965                 970                 975

Gly Asn Ile Phe Val Cys Ser Val Cys Lys Lys Glu Phe Ala Phe Leu
            980                 985                 990

Cys Asn Leu Gln Gln His Gln Arg Asp Leu His Pro Asp Glu Val Cys
            995                 1000                1005

Thr His His Glu Phe Glu Ser Gly Thr Leu Arg Pro Gln Asn Phe Thr
    1010                1015                1020

Asp Pro Ser Lys Ala Asn Val Glu His Met Pro Ser Leu Pro Glu Glu
1025                1030                1035                1040

Pro Leu Glu Thr Ser Arg Glu Glu Leu Asn Asp Ser Ser Glu Glu
                1045                1050                1055

Leu Tyr Thr Thr Ile Lys Ile Met Ala Ser Gly Ile Lys Thr Lys Asp
                1060                1065                1070

Pro Asp Val Arg Leu Gly Leu Asn Gln His Tyr Pro Ser Phe Lys Pro
                1075                1080                1085

Pro Pro Phe Gln Tyr His His Arg Asn Pro Met Gly Ile Gly Val Thr
    1090                1095                1100

Ala Thr Asn Phe Thr Thr His Asn Ile Pro Gln Thr Phe Thr Thr Ala
1105                1110                1115                1120

Ile Arg Cys Thr Lys Cys Gly Lys Gly Val Asp Asn Met Pro Glu Leu
                1125                1130                1135

His Lys His Ile Leu Ala Cys Ala Ser Ala Ser Asp Lys Lys Arg Tyr
                1140                1145                1150

Thr Pro Lys Lys Asn Pro Val Pro Leu Lys Gln Thr Val Gln Pro Lys
    1155                1160                1165

Asn Gly Val Val Leu Asp Asn Ser Gly Lys Asn Ala Phe Arg Arg
    1170                1175                1180

Met Gly Gln Pro Lys Arg Leu Ser Phe Asn Val Glu Leu Gly Lys Met
1185                1190                1195                1200

Ser Pro Asn Lys Leu Lys Leu Ser Ala Leu Lys Lys Lys Asn Gln Leu
                1205                1210                1215

Val Gln Lys Ala Ile Leu Gln Lys Asn Arg Ala Ala Lys Gln Lys Ala
                1220                1225                1230

Asp Leu Arg Asp Thr Ser Glu Ala Ser Ser His Ile Cys Pro Tyr Cys
                1235                1240                1245

Asp Arg Glu Phe Thr Tyr Ile Gly Ser Leu Asn Lys His Ala Ala Phe
    1250                1255                1260

Ser Cys Pro Lys Lys Pro Leu Ser Pro Ser Lys Arg Lys Val Ser His
```

```
                1265                1270                1275                1280
Ser Ser Lys Lys Gly Gly His Ala Ser Ser Ser Ser Asp Arg Asn
                1285                1290                1295

Ser Ser Cys His Pro Arg Arg Arg Thr Ala Asp Thr Glu Ile Lys Met
            1300                1305                1310

Gln Ser Thr Gln Ala Pro Leu Gly Lys Thr Arg Ala Arg Ser Thr Gly
        1315                1320                1325

Pro Ala Gln Ala Ser Leu Pro Ser Ser Ser Phe Arg Ser Arg Gln Asn
    1330                1335                1340

Val Lys Phe Ala Ala Ser Val Lys Ser Lys Ala Ser Ser Ser
1345                1350                1355                1360

Leu Arg Asn Ser Ser Pro Ile Arg Met Ala Lys Ile Thr His Val Glu
                1365                1370                1375

Gly Lys Lys Pro Lys Ala Val Ala Lys Ser His Ser Ala Gln Leu Ser
            1380                1385                1390

Ser Lys Ser Ser Arg Gly Leu His Val Arg Val Gln Lys Ser Lys Ala
        1395                1400                1405

Val Ile Gln Ser Lys Thr Ala Leu Ala Ser Lys Arg Arg Thr Asp Arg
1410                1415                1420

Phe Ile Val Lys Ser Arg Glu Arg Ser Gly Gly Pro Ile Thr Arg Ser
1425                1430                1435                1440

Leu Gln Leu Ala Ala Ala Ala Asp Leu Ser Glu Ser Arg Arg Glu Asp
                1445                1450                1455

Ser Ser Ala Arg His Glu Leu Lys Asp Phe Ser Tyr Ser Leu Arg Leu
            1460                1465                1470

Ala Ser Arg Cys Gly Ser Ser Thr Ala Ser Tyr Ile Thr Arg Gln Cys
        1475                1480                1485

Arg Lys Val Lys Ala Ala Ala Thr Pro Phe Gln Gly Pro Phe Leu
    1490                1495                1500

Lys Glu
1505

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
ggttgggtgg tggttattgg g                                                   21

<210> SEQ ID NO 6
<211> LENGTH: 28
<212> TYPE: DNA
<213> ORGANISM: Artificial Sequence
<220> FEATURE:
<223> OTHER INFORMATION: primer

<400> SEQUENCE: 6
caaaaaccgc cctgcgccac tccttacc                                            28

<210> SEQ ID NO 7
<211> LENGTH: 22
<212> TYPE: DNA
<213> ORGANISM: Artificial Sequence
<220> FEATURE:
<223> OTHER INFORMATION: primer
```

```
<400> SEQUENCE: 7
gtggtggtta ttgggcgacg gc                                        22

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
gctatttcgc cgaccccgac g                                         21

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
tggtggttat tgggtgatgg t                                         21

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
actatttcac caaccccaag a                                         21

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
aaaccatgga tcagaacact actgag                                    26

<210> SEQ ID NO 12
<211> LENGTH: 31
<212> TYPE: DNA
<213> ORGANISM: Artificial Sequence
<220> FEATURE:
<223> OTHER INFORMATION: primer

<400> SEQUENCE: 12
ccgtaagctt catgcagagg tgaaatctgg c                              31

<210> SEQ ID NO 13
<211> LENGTH: 39
<212> TYPE: DNA
<213> ORGANISM: Artificial Sequence
<220> FEATURE:
<223> OTHER INFORMATION: primer

<400> SEQUENCE: 13
cgagccagcg cccggagcta agcttaagcg gagctcccc                      39

<210> SEQ ID NO 14
<211> LENGTH: 34
```

```
<212> TYPE: DNA
<213> ORGANISM: Artificial Sequence
<220> FEATURE:
<223> OTHER INFORMATION: primer

<400> SEQUENCE: 14
gatttattag aggaatgaaa acaacttca gaag                              34

<210> SEQ ID NO 15
<211> LENGTH: 34
<212> TYPE: DNA
<213> ORGANISM: Artificial Sequence
<220> FEATURE:
<223> OTHER INFORMATION: primer

<400> SEQUENCE: 15
cttctgaagt tgtttttcat tcctctaata aatc                             34

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
ctcattcatc taagaaaggt gg                                          22

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
tgattccagg tcacttcagg                                             20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
gaagccaaag gcctctcatc                                             20

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
agactctggc tgaggtacc                                              19
```